US012673014B2

(12) United States Patent
Chatterjee

(10) Patent No.: US 12,673,014 B2
(45) Date of Patent: Jul. 7, 2026

(54) INHIBITORS OF GLYCOSPHINGOLIPID SYNTHESIS AND METHODS OF USE

(71) Applicant: Subroto B. Chatterjee, Columbia, MD (US)

(72) Inventor: Subroto B. Chatterjee, Columbia, MD (US)

(73) Assignee: Chatterjee Subroto, Columbia, MD (US)

( * ) Notice: Subject to any disclaimer, the term of this patent is extended or adjusted under 35 U.S.C. 154(b) by 0 days.

(21) Appl. No.: 16/972,575

(22) PCT Filed: Jun. 5, 2019

(86) PCT No.: PCT/US2019/035611
§ 371 (c)(1),
(2) Date: Dec. 4, 2020

(87) PCT Pub. No.: WO2019/236722
PCT Pub. Date: Dec. 12, 2019

(65) Prior Publication Data

US 2021/0244638 A1      Aug. 12, 2021

Related U.S. Application Data

(60) Provisional application No. 62/680,751, filed on Jun. 5, 2018.

(51) Int. Cl.
| *A61K 8/42* | (2006.01) |
| *A61K 8/362* | (2006.01) |
| *A61K 8/81* | (2006.01) |
| *A61K 45/06* | (2006.01) |
| *C07K 16/40* | (2006.01) |

(52) U.S. Cl.
CPC ............... *A61K 8/42* (2013.01); *A61K 8/362* (2013.01); *A61K 8/8111* (2013.01); *A61K 45/06* (2013.01); *C07K 16/40* (2013.01)

(58) Field of Classification Search
CPC ...... A61K 8/362; A61K 39/3955; A61K 8/42; A61K 9/5015; A61K 8/8111; A61K 45/06; A61K 9/0014; A61K 9/5031; A61K 31/5375; A61K 2300/00; A61P 17/02; A61P 17/14; A61P 17/00; C07K 16/40
See application file for complete search history.

(56) References Cited

U.S. PATENT DOCUMENTS

| 6,235,737 | B1 * | 5/2001 | Styczynski | ............ A61K 31/40 |
| | | | | 514/315 |
| 6,511,979 | B1 * | 1/2003 | Chatterjee | ............... A61P 17/02 |
| | | | | 514/237.8 |
| 6,824,785 | B1 * | 11/2004 | Kitson | ..................... A61K 8/68 |
| | | | | 424/400 |

| 2010/0028878 | A1 | 2/2010 | Labrie et al. |
| 2010/0062492 | A1 | 3/2010 | Park et al. |
| 2011/0059909 | A1 * | 3/2011 | Singh ..................... A61K 45/06 |
| | | | 514/25 |
| 2013/0040953 | A1 * | 2/2013 | Paller ..................... A61L 15/32 |
| | | | 514/237.8 |
| 2013/0041015 | A1 * | 2/2013 | Chatterjee ........ G01N 33/57438 |
| | | | 506/9 |
| 2016/0250221 | A1 | 9/2016 | La Montagna et al. |
| 2017/0119683 | A1 * | 5/2017 | Chatterjee ............. A61K 45/06 |

FOREIGN PATENT DOCUMENTS

| CN | 103284950 B | 12/2014 |
| KR | 20160066169 A | 6/2016 |
| WO | 2001054654 A2 | 8/2001 |
| WO | 2003082284 A1 | 10/2003 |
| WO | 2005/123055 A2 | 12/2005 |

OTHER PUBLICATIONS

"Prevent." Macmillandictionary.com. Macmillian, 2019. Web. Feb. 1, 2019 (Year: 2019).*
Cleveland Clinic. "Hair Loss in Women." Retrieved Dec. 9, 2021. Retrieved from internet <URL: https://my.clevelandclinic.org/health/diseases/16921-hair-loss-in-women >; pp. 1-13. (Year: 2021).*
Healthline. "What Causes White Hair." Retrieved Dec. 16, 2021. Retrieved from internet <URL: https://www.healthline.com/health/white-hair>; pp. 1-3. (Year: 2021).*
Shayman, J.A., Hinkovska-Galcheva, V., Shu, L. (2023). Inhibitors of Glucosylceramide Synthase. in: Kabayama, K., Inokuchi, Ji. (eds) Glycolipids. Methods in Molecular Biology, vol. 2613. Humana, New York, NY. https://doi.org/10.1007/978-1-0716-2910-9_20. (Year: 2023).*
Healthline. "Why Hair Can't Return to Its Original Color After Turning White or Gray." Retrieved online on Feb. 27, 2025, from <URL: https://www.healthline.com/health/can-white-hair-turn-black-again; 13 pages. (Year: 2025).*
Mishra et al., "Improved intervention of Atherosclerosis and Cardiac Hypertrophy through Biodegradable Polymer-Encapsulated Delivery of Glycosphingolipid Inhibitor," Biomaterials, 64:125-135, 2015.
Bedja et al., "Inhibition of Glycosphingolipid Synthesis Reverses Skin Infammation and Hair Loss in APOE-/- Mice Fed Western Diet," Scientific Reports, 8:1-11, 2018.
Mellor et al., "Cellular Effects of Deoxynojirimycin Analogues: Uptake, Retention and Inhibition of Glycosphingolipid Biosynthesis," Biochemistry Journal, 381:861-866, 2004.
International Search Report and the Written Opinion from Corresponding PCT Application No. PCT/US2019/035611 dated Oct. 7, 2019, 15 pages.

(Continued)

*Primary Examiner* — Doan T Phan
(74) *Attorney, Agent, or Firm* — Fox Rothschild LLP; Peter F. Corless

(57) ABSTRACT

Compositions in the prevention and treatment of skin diseases or associated disorders, inflammation or inflammatory diseases or disorders, include at least one inhibitor of glycosphingolipid synthesis.

8 Claims, 19 Drawing Sheets

Specification includes a Sequence Listing.

(56)                References Cited

OTHER PUBLICATIONS

Teng Yu et al. "1-Phenyl-2-decanoylamino-3-morpholino-1-propanol (PDMP) facilities curcumin-induced melanoma cell apoptosis by enhancing ceramide accumulation, JNK activation, and inhibiting PI3K/AKT activation," Molecular and Cellular Biochemistry, vol. 361, No. 1-2, pp. 47-57 (2011). Abstract only.

Bodas et al., "Lactosylceramide-accumulation in lipid-rafts mediate aberrate-autophagy, inflammation and apoptosis in cigarette induced emphysema," Apoptosis Lindon GB, vol. 20, No. 5, pp. 725-739 (2015). Abstract only.

Radin Norman et al., "Use of an Inhibitor of Glucosyceramide Synthesis, D-1-Phenyl-2-decanoylamino-3-morpholino-1-propanol," Neuroprotocols, vol. 3, No. 2, pp. 145-155, (1993). Abstract only.

European Search Report for EP19815504.6 dated Aug. 7, 2023.

* cited by examiner

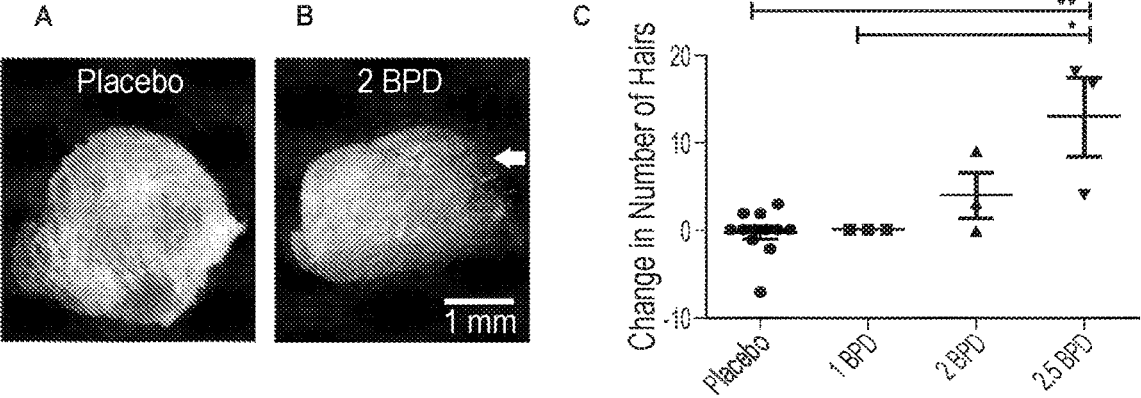
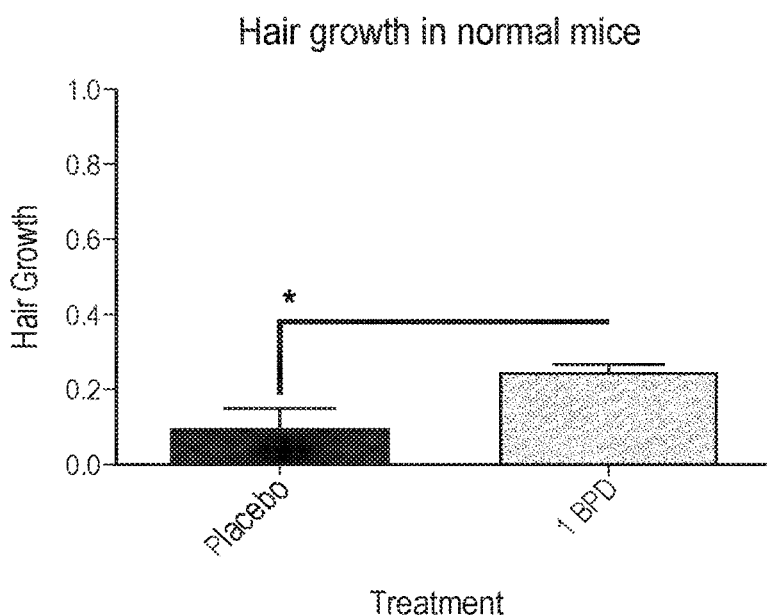
FIG. 20A-20D

Psoriasis patients have characteristically low circulating ceramide levels

Treatment with BPD increases ceramide level in lesional skin in psoriasis patients

INHIBITORS OF GLYCOSPHINGOLIPID SYNTHESIS AND METHODS OF USE

CROSS-REFERENCE TO RELATED APPLICATIONS

This application is a National Stage Application filed under 35 U.S.C. § 371, of International Patent Application No PCT/US2019/035611, filed on Jun. 5, 2019, which claims the benefit of and priority to U.S. Provisional Application No. 62/680,751, filed on Jun. 5, 2018. The entire contents of which are incorporated herein by reference in their entirety.

INCORPORATION BY REFERENCE OF SEQUENCE LISTING

The contents of the sequence listing text file named "048362-503001WO_Sequence_Listing_txt", which was created on Jul. 25, 2019 and is 2,445 bytes in size, are incorporated herein by reference in its entirety.

FIELD OF THE INVENTION

Embodiments are directed to compositions that inhibit glycosphingolipid synthesis and their use in the treatment of skin diseases, WOUND HEALING, hair loss and discoloration thereof.

BACKGROUND

Glycosphingolipids (GSLs) are integral components of all cell membranes, and affect numerous biological functions[1]. Glycosphingolipids are synthesized by the sequential transfer of monosaccharides such as glucose, from the nucleotide sugar, UDP-glucose, to ceramide to form glucosylceramide (GlcCer)[2]. Analogously, the subsequent transfer of galactose from UDP-Gal to GlcCer, via the activity of a galactosyltransferase, produces lactosylceramide (LacCer). Such GSLs are then assembled into very low-density lipoproteins (VLDLs), in the liver, and secreted into circulating blood. VLDL is modified to cholesterol and GSL-rich low-density lipoprotein (LDL) particles, for delivery to peripheral tissues, including the skin, the most predominant tissue in mammals. The uppermost layer of the skin, the stratum corneum, is made up of enucleate corneocytes, which are surrounded by extracellular lipids, to form multi-lamellar structures. These lipids thus impart an overwhelmingly impenetrable barrier function to the stratum corneum[3]. Thus, glycosphingolipids constitute a major species of lipids in human skin, skin fibroblasts, and keratinocytes[4-6].

Dermatitis is a common skin disorder effecting 1 to 21% of mouse population in research laboratories and facilities[16-18] Leading to unnecessary euthanasia[15] and thus loss of important data. Dermatitis was reported to occur in the face, head and neck area in the C57BL/6 mice and mice with the same genetic background[15-18]. Scratching, the affected area due pruritus and fights increases the severity of ulceration[15]. Others risk factors that may predispose mouse to this disorder including abnormal grooming behavior before the onset of lesion, high fat diet, gender differences as well as aging[16, 18-22, 23, 24]. However, the mechanism of this disorder/dermatitis is still unknown and treatment with triple anti-biotic ointment, sulfadiazine, and toes trimming as well as others methods may not be effective but are variable in effectiveness[15, 16, 18, 25].

SUMMARY

Embodiments of the invention are directed to compositions comprising inhibitors of glycosphingolipid synthesis and methods of use.

In a first aspect, a method of treating skin inflammation and associated disorders thereof, comprises administering to a subject in need thereof a composition comprising a therapeutically effective amount of one or more inhibitors of glycosphingolipid synthesis. In certain embodiments, the composition comprises one or more lipids. In certain embodiments, the composition comprises ceramides. In certain embodiments, the pharmaceutical composition comprises D-threo-1-phenyl-2-decanoylamino-3-morpholino-1-propanol (D-PDMP), (1R,2R)-nonanoic acid[2-(2',3'-dihydro-benzo [1, 4] dioxin-6'-yl)-2-hydroxy-1-pyrrolidin-1-ylmethyl-ethyl]-amide-L-tartaric acid salt (Genz-123346), biodegradable polymer (BPD), lipids, ceramides or combinations thereof. In certain embodiments, the D-PDMP, lipids, ceramides or combinations thereof are encapsulated by a biodegradable polymer. Examples of lipids include, without limitation fatty acids, free fatty acids, cholesterol, sterol esters, triglycerides, diglycerides, glycerides, wax esters, squalene, ceramides, lipids, phospholipids, glycolipids, linoleic acids or combinations thereof. In certain embodiments, an antibody which specifically binds to β1,4-Galactosyltransferase V (BGA), isoforms or peptides thereof, is administered to the subject. In certain embodiments, the antibody which specifically binds to β1,4-Galactosyltransferase V (BGA), isoforms or peptides thereof is administered prior to, in conjunction with or after application of the inhibitors of glycosphingolipid synthesis. In certain embodiments, the composition comprising inhibitors of glycosphingolipid synthesis includes a therapeutically effective amount of the antibody which specifically binds to β1,4-Galactosyltransferase V (BGA), isoforms or peptides thereof.

In a second aspect, a method of inhibiting neutrophil migration to skin wounds and lesions, comprises administering to a subject in need thereof a composition comprising a therapeutically effective amount of one or more inhibitors of glycosphingolipid synthesis. In certain embodiments, the composition comprises one or more lipids. In certain embodiments, the pharmaceutical composition comprises D-PDMP, (1R,2R)-nonanoic acid[2-(2',3'-dihydro-benzo [1, 4] dioxin-6'-yl)-2-hydroxy-1-pyrrolidin-1-ylmethyl-ethyl]-amide-L-tartaric acid salt (Genz-123346), BPD, lipids, ceramides or combinations thereof. In certain embodiments, the D-PDMP, (1R,2R)-nonanoic acid[2-(2',3'-dihydro-benzo [1, 4] dioxin-6'-yl)-2-hydroxy-1-pyrrolidin-1-ylmethyl-ethyl]-amide-L-tartaric acid salt (Genz-123346), lipids, ceramides or combinations thereof are encapsulated by a biodegradable polymer. In certain embodiments, an antibody which specifically binds to β1,4-Galactosyltransferase V (BGA), isoforms or peptides thereof, is administered to the subject. In certain embodiments, the antibody which specifically binds to β1,4-Galactosyltransferase V (BGA), isoforms or peptides thereof is administered prior to, in conjunction with or after application of the inhibitors of glycosphingolipid synthesis. In certain embodiments, the composition comprising inhibitors of glycosphingolipid synthesis includes a therapeutically effective amount of the antibody which specifically binds to β1,4-Galactosyltransferase V (BGA), isoforms or peptides thereof.

In a third aspect, a method of preventing and/or reversing hair loss comprises administering to a subject in need thereof a composition comprising a therapeutically effective amount of an inhibitor of glycosphingolipid synthesis. In certain embodiments, the composition comprises one or more lipids. In certain embodiments, the composition comprises ceramides. In certain embodiments, the pharmaceutical composition comprises D-PDMP, BPD, (1R,2R)-nonanoic acid[2-(2',3'-dihydro-benzo [1, 4] dioxin-6'-yl)-2-hydroxy-1-pyrrolidin-1-ylmethyl-ethyl]-amide-1-tartaric acid salt (Genz-123346), lipids, ceramides or combinations thereof. In certain embodiments, the D-PDMP, (1R,2R)-nonanoic acid[2-(2',3'-dihydro-benzo [1, 4] dioxin-6'-yl)-2-hydroxy-1-pyrrolidin-1-ylmethyl-ethyl]-amide-L-tartaric acid salt (Genz-123346), lipids, ceramides or combinations thereof are encapsulated by a biodegradable polymer. In certain embodiments, an antibody which specifically binds to β1,4-Galactosyltransferase V (BGA), isoforms or peptides thereof, is administered to the subject. In certain embodiments, the antibody which specifically binds to β1,4-Galactosyltransferase V (BGA), isoforms or peptides thereof is administered prior to, in conjunction with or after application of the inhibitors of glycosphingolipid synthesis. In certain embodiments, the composition comprising inhibitors of glycosphingolipid synthesis includes a therapeutically effective amount of the antibody which specifically binds to β1,4-Galactosyltransferase V (BGA), isoforms or peptides thereof.

In a fourth aspect, a method of preventing and/or reversing hair discoloration comprises administering to a subject in need thereof a composition comprising a therapeutically effective amount of an inhibitor of glycosphingolipid synthesis. In certain embodiments, the composition comprises one or more lipids. In certain embodiments, the composition comprises ceramides. In certain embodiments, the pharmaceutical composition comprises D-PDMP, BPD, (1R,2R)-nonanoic acid[2-(2',3'-dihydro-benzo [1, 4] dioxin-6'-yl)-2-hydroxy-1-pyrrolidin-1-ylmethyl-ethyl]-amide-L-tartaric acid salt (Genz-123346), lipids, ceramides or combinations thereof. In certain embodiments, the D-PDMP, (1R,2R)-nonanoic acid[2-(2',3'-dihydro-benzo [1, 4] dioxin-6'-yl)-2-hydroxy-1-pyrrolidin-1-ylmethyl-ethyl]-amide-L-tartaric acid salt (Genz-123346), lipids, ceramides or combinations thereof are encapsulated by a biodegradable polymer. In certain embodiments, an antibody which specifically binds to β1,4-Galactosyltransferase V (BGA), isoforms or peptides thereof, is administered to the subject. In certain embodiments, the antibody which specifically binds to β1,4-Galactosyltransferase V (BGA), isoforms or peptides thereof is administered prior to, in conjunction with or after application of the inhibitors of glycosphingolipid synthesis. In certain embodiments, the composition comprising inhibitors of glycosphingolipid synthesis includes a therapeutically effective amount of the antibody which specifically binds to β1,4-Galactosyltransferase V (BGA), isoforms or peptides thereof.

In a fifth aspect, a pharmaceutical composition formulated for oral or topical administration comprises a therapeutically effective amount of an inhibitor of glycosphingolipid synthesis. In certain embodiments, the compositions are formulated to be administered as a patch applied to the skin. In certain embodiments, the pharmaceutical composition increases or replenishes the amounts of skin lipids. In this and other embodiments, the inhibitor of glycosphingolipid synthesis is an imino sugar. In certain embodiments, the imide sugar is N-butyldeoxynojirimycin, N-butyldeoxygalactonojirimycin (NB-DGJ), or N-nonyldeoxynojirimycin. In certain embodiments, the pharmaceutical composition comprises D-PDMP, BPD, (1R,2R)-nonanoic acid[2-(2',3'-dihydro-benzo [1, 4] dioxin-6'-yl)-2-hydroxy-1-pyrrolidin-1-ylmethyl-ethyl]-amide-L-tartaric acid salt (Genz-123346), lipids, ceramides or combinations thereof. In certain embodiments, the D-PDMP, (1R,2R)-nonanoic acid[2-(2',3'-dihydro-benzo [1, 4] dioxin-6'-yl)-2-hydroxy-1-pyrrolidin-1-ylmethyl-ethyl]-amide-L-tartaric acid salt (Genz-123346), lipids, ceramides or combinations thereof are encapsulated by a biodegradable polymer. Examples of lipids include, without limitation fatty acids, free fatty acids, cholesterol, sterol esters, triglycerides, diglycerides, glycerides, wax esters, squalene, ceramides, lipids, phospholipids, glycolipids, linoleic acids or combinations thereof. In certain embodiments, an antibody which specifically binds to β1,4-Galactosyltransferase V (BGA), isoforms or peptides thereof, is administered to the subject. In certain embodiments, the antibody which specifically binds to β1,4-Galactosyltransferase V (BGA), isoforms or peptides thereof is administered prior to, in conjunction with or after application of the inhibitors of glycosphingolipid synthesis. In certain embodiments, the composition comprising inhibitors of glycosphingolipid synthesis includes a therapeutically effective amount of the antibody which specifically binds to β1,4-Galactosyltransferase V (BGA), isoforms or peptides thereof.

In a sixth aspect, a composition comprises an inhibitor of glycosphingolipid synthesis, an inhibitor of glucosylceramide synthase or a combination thereof. In certain embodiments, a compound that inhibits glucosylceramide synthesis is an imino sugar. In another embodiment, the imide sugar is N-butyldeoxynojirimycin, N-butyldeoxygalactonojirimycin (NB-DGJ), or N-nonyldeoxynojirimycin. In another embodiment, the inhibitor of glucosylceramide synthesis is 1-phenyl-2-decanoylamino-3-morpholino-1-propanol (DMP), D-threo-1-phenyl-2-decanoylamino-3-morpholino-1-propanol and structurally related analogues thereof. In another embodiment, the inhibitor of glucosylceramide synthesis is 1-phenyl-2-palmitoyl-amino-3-morpholino-1-propanol (PPMP) and structurally related analogues thereof. In certain embodiments, the composition comprises D-threo-1-phenyl-2-decanoylamino-3-morpholino-1-propanol (D-PDMP), (1R,2R)-nonanoic acid[2-(2',3'-dihydro-benzo [1, 4] dioxin-6'-yl)-2-hydroxy-1-pyrrolidin-1-ylmethyl-ethyl]-amide-L-tartaric acid salt (Genz-123346), an imide sugar, 1-phenyl-2-decanoylamino-3-morpholino-1-propanol (DMP), 1-phenyl-2-palmitoyl-amino-3-morpholino-1-propanol (PPMP), lipids, ceramides or combinations thereof are encapsulated by a biodegradable polymer. In certain embodiments, the composition comprising inhibitors of glycosphingolipid synthesis includes a therapeutically effective amount of the antibody which specifically binds to β1,4-Galactosyltransferase V (BGA), isoforms or peptides thereof.

In a seventh aspect, a method of preventing or treating an inflammatory disease or disorder in a subject, comprises administering a composition comprising a therapeutically effective amount of an inhibitor of glycosphingolipid synthesis. In certain embodiments, an antibody which specifically binds to β1,4-Galactosyltransferase V (BGA), isoforms or peptides thereof, is administered to the subject. In certain embodiments, the antibody which specifically binds to β1,4-Galactosyltransferase V (BGA), isoforms or peptides thereof is administered prior to, in conjunction with or after application of the inhibitors of glycosphingolipid synthesis. In certain embodiments, the composition comprising inhibitors of glycosphingolipid synthesis includes a therapeutically effective amount of the antibody which specifically binds to β1, 4-Galactosyltransferase V (BGA), isoforms or peptides thereof. In certain embodiments, the composition further comprises an agent which inhibits β1, 4-Galactosyltransferase V (BGA) expression or activity. Examples of agents include small molecule compounds, antisense reagents, siRNA reagents, antibodies, enzymes, peptides organic or inorganic molecules, natural or synthetic compounds and the like. In certain embodiments, the inhibitor of glycosphingolipid synthesis is formulated for oral or topical administration. In certain embodiments the formulation comprises one or more anti-inflammatory agents, steroidal drugs or non-steroidal anti-inflammatory drugs (NSAIDS), wound healing agents, cytokines, cannabinoids, antibodies, anti-viral agents, anti-fungal agents or combinations thereof.

Other aspects are described infra.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

The term "administering," as used herein, refers to any mode of transferring, delivering, introducing, or transporting a therapeutic agent to a subject in need of treatment with such an agent. Such modes include, but are not limited to, oral, topical, intravenous, intraperitoneal, intramuscular, intradermal, intranasal, and subcutaneous administration.

As used herein, the term "agent" is meant to encompass any molecule, chemical entity, composition, drug, therapeutic agent, chemotherapeutic agent, or biological agent capable of modulating β1,4-Galactosyltransferase V (BGA) expression or activity. The term includes small molecule compounds, antisense oligonucleotides, siRNA reagents, antibodies, antibody fragments bearing epitope recognition sites, such as Fab, Fab', $F(ab')_2$ fragments, Fv fragments, single chain antibodies, antibody mimetics (such as DARPins, affibody molecules, affilins, affitins, anticalins, avimers, fynomers, Kunitz domain peptides and monobodies), peptoids, aptamers; enzymes, peptides organic or inorganic molecules, natural or synthetic compounds and the like. An agent can be assayed in accordance with the methods of the invention at any stage during clinical trials, during pre-trial testing, or following FDA-approval.

As used herein, the term "antibody" is inclusive of all species, including human and humanized antibodies and the antigenic target, can be from any species. Thus, an antibody, for example, which binds to an antigen "X" can be mouse anti-human X, human anti-human X; humanized anti-human X, goat anti-human X; goat anti-mouse X; rat anti-human X; mouse anti-rat X and the like. The combinations of antibody generated in a certain species against an antigen target, e.g. "X", from another species, or in some instances the same species (for example, in autoimmune or inflammatory response) are limitless and all species are embodied in this invention. The term antibody is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab', $F(ab)_2$, Fv, single chain antibodies, diabodies), comprising complementarity determining regions (CDRs) of the foregoing as long as they exhibit the desired biological activity.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA. An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, short, hairpin RNA (shRNA), therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

As used in this specification and the appended claims, the term "or" is generally employed in its sense including "and/or" unless the content clearly dictates otherwise.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health. A disease or disorder is "alleviated" if the severity of a symptom of the disease or disorder, the frequency with which such a symptom is experienced by a patient, or both, is reduced.

As used herein, a "controlled release dosage formulation" refers to a formulation of a drug that offers prolonged release at a specific controllable rate.

By "effective amount" is meant the amount required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. Determination of a therapeutically effective amount, as well as other factors related to effective administration of a compound of the present invention to a subject of this invention, including dosage forms, routes of administration, and frequency of dosing, may depend upon the particulars of the condition that is encountered, including the subject and condition being treated or addressed, the severity of the condition in a particular subject, the particular compound being employed, the particular route of administration being employed, the frequency of dosing, and the particular formulation being employed. Determination of a therapeutically effective treatment regimen for a subject of this invention is within the level of ordinary skill in the medical or veterinarian arts. In clinical use, an effective amount may be the amount that is recommended by the U.S. Food and Drug Administration, or an equivalent foreign agency. The amount of active ingredient that can be combined with the carrier materials to produce a single dosage form varies depending upon the subject being treated and the particular mode of administration.

The term "high affinity" for an antibody refers to an antibody having a $K_D$ of $1\times10^{-7}$ M or less, more preferably $5\times10^{-8}$ M or less, even more preferably $1\times10^{-8}$ M or less, even more preferably $5\times10^{-9}$ M or less and even more preferably $1\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, $10^{-7}$ M or less, or $10^{-8}$ M or less.

The term "enhancement," "enhance," "enhances," or "enhancing" refers to an increase in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or an increase in the specified activity of at least about 5%, 10%, 25%, 35%, 40%, 50%, 60%, 75%, 80%, 90%, 95%, 97%, 98%, 99% or 100%.

As used herein, the term "in combination" in the context of the administration of a therapy to a subject refers to the use of more than one therapy for therapeutic benefit. The term "in combination" in the context of the administration can also refer to the prophylactic use of a therapy to a subject when used with at least one additional therapy. The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which had, has, or is susceptible to cancer. The therapies are administered to a subject in a sequence and within a time interval such that the therapies can act together. In a particular embodiment, the therapies are administered to a subject in a sequence and within a time interval such that they provide an increased benefit than if they were administered otherwise. Any additional therapy can be administered in any order with the other additional therapy.

As used herein, an "inhibitor" of glycosphingolipid synthesis or of glucosylceramide synthesis inhibits the synthesis of these molecules including those associated in the cycle of the synthesis. The inhibition of synthesis of these molecules can be measured by any standard assay. See, for example, the methods in the examples section which follows.

As used herein, "inhibition" or "decrease" of β1,4-Galactosyltransferase V reduces the amount of β1,4-Galactosyltransferase V in the cell by greater than about 20%, 40%, 60%, 80%, 85%, 90%, 95%, or 100%. The amount of β1,4-Galactosyltransferase V can be determined by well-known methods including, but are not limited to, densitometer, fluorometer, radiography, luminometer, antibody-based methods and activity measurements.

The term "inhibit," "diminish," "reduce" or "suppress" refers to a decrease in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or a decrease or reduction in the specified activity of at least about 5%, 10%, 25%, 35%, 40%, 50%, 60%, 75%, 80%, 90%, 95%, 97%, 98%, 99% or 100%. These terms are intended to be relative to a reference or control.

The term "$K_{assoc}$" or "$K_a$," as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, for example, using a biosensor system such as a BIACORE™ system.

As used herein, "modulate," "modulates" or "modulation" refers to enhancement (e.g., an increase) or inhibition (e.g., diminished, reduced or suppressed) of the specified activity.

As used herein, the terms "prevent," "preventing" and "prevention" in the context of the administration of a therapy to a subject refer to the prevention or inhibition of the recurrence, onset, and/or development of a disease or disorder or a symptom thereof in a subject resulting from the administration of a therapy (e.g., a prophylactic agent), or a combination of therapies (e.g., a combination of prophylactic agents).

By "reduces" is meant a negative alteration of at least 10%, 25%, 50%, 75%, or 100% as compared to a reference.

By "reference" is meant a standard or control condition.

As used herein, an antibody that "specifically binds" to a polypeptide or epitope is intended to refer to a an antibody that binds to a polypeptide or epitope with a $K_D$ of $1\times10^{-7}$ M or less, or $5\times10^{-8}$ M or less, or $3\times10^{-8}$ M or less, more preferably $1\times10^{-8}$ M or less, or $5\times10^{-9}$ M or less. Therefore, the terms "specific binding" or "specifically binding" when used in reference to the interaction of a protein and an antibody or alternative protein scaffold or peptoid or aptamers, means that the interaction is dependent upon the presence of a particular structure (i.e., the antigenic determinant or epitope) on the protein; in other words the antibody is recognizing and binding to a specific protein structure rather than to proteins in general. Thus, an antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

As used herein, a "sustained release dosage formulation" is a formulation of a drug designed to release the drug at a predetermined rate in order to maintain a constant drug concentration for a specific period of time with minimum side effects. Optionally, the period of time is 30 minutes or more, e.g., 2-4 hours or more, e.g., 3-8 hours or more, e.g., 4-24 hours or more, e.g., 1-3 days or more, e.g., 2-7 days or more, e.g., 4-14 days or more, e.g., 7 days or more, e.g., 14 days to a month or more.

As used herein, "wound" includes injuries to the skin wherein the skin is torn, cut or punctured. A wound is a break in the skin. In one embodiment, the wound is caused by skin contact with a foreign object. The break in the skin may cause external bleeding. Wounds include open wounds, for example, abrasions, lacerations, incisions, punctures, avulsions, or amputations. Wounds also include burn wounds. A burn is a type of injury to flesh caused by heat, electricity, chemicals, light, radiation or friction.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

BRIEF DESCRIPTION OF THE DRAWINGS

FIG. 1A represents mice fed normal chow diet. FIGS. 1B and 1H show ApoE-mice fed a western diet from 12-20 weeks with moderately increased hair whitening, loss of hair, skin inflammation and lesion formation. FIGS. 1D and 1I shows extensive loss of hair, skin lesion when the western diet was continued to 36 weeks of age, compared to ApoE-mice fed chow for 36 weeks (FIGS. 1C and 1I). FIGS. 1E and 1F show mice fed a combination of western diet and 1 mpk BPD (FIG. 1E) and 10 mpk BPD (FIG. 1F), from 20 weeks to 36 weeks, with ameliorated hair discoloration, hair loss, and skin inflammation. FIG. 1G shows mice treated with 10 mpk unbound D-PDMP and fed western diet. This treatment also reduced the occurrence of these pathologies (FIGS. 1G and 1I). Note treatment with 1 mpk BPD was as efficient as 10 mpk of native/un-encapsulated D-PDMP in regard to hair discoloration and hair loss (FIG. 1I). (N=5 p<0.05). Quantitative analysis shows 75% of skin area had hair loss, discoloration and inflammation (FIG. 1I) in placebo mice. Treatment with BPD or D-PDMP interfered with this phenotype in dose-dependent. And 1 mpk of BPD was as effective (87%) as 10 mpk of D-PDMP (83%) in wound healing (FIGS. 1I, 1J). A nonparametric one-way ANOVA using the Kruskal-Wallis test and Dunn's multiple comparison post-test was performed. *p<0.05, p<, 001, *p<0.001; n=3-5.

(FIG. 6A-6G) MS/MS analysis of control mice skin ceramides showed that d18:/24:0, d18:/26:1, d18:/16:1, d18:1/24:1, d18:1/22:1, d18:1/18:0, and d18:1/20:0 were the predominant fatty acid molecular species (in the hydrophobic "tails" of ceramides), in a descending order. Western diet decreased, by ~3-fold, the levels of almost all fatty acid molecular species of ceramide, except for C18:1/24:0, which did not change significantly (FIG. 6E). Treatment with 1 mpk BPD, or 10 mpk D-PDMP, on the other hand, increased them to normal levels. Neither the 10 mpk D-PDMP reverse the loss of d18:1/26:1 ceramide, nor did increasing the dose of BPD from 1 to 5 mpk, affect levels of skin ceramides, demonstrating the negative consequences of aging, including pigmentation and hair loss.

(FIG. 9B) or 5 mpk of BPD (FIG. 9C) Wounds, skin, and hair phenotypes of the mice were photographed. (FIG. 9D) shows the decrease in the wound area from day 1 to day 9. Wounded mice treated with 5 mpk BPD was the first group to heal completely. Hair growth was earlier and greater in mice treated with 5 mpk BPD (FIG. 9C) as compared to mice treated with 1 mpk BPD (FIG. 9B) and mice treated with placebo (FIG. 9A). Mice treated with 1 mpk BPD also showed greater hair growth than mice treated with placebo (FIG. 9E). In the placebo-treated mice, the skin darkened evenly by day 15, but hair growth was not as noticeable as in BPD-treated mice (FIGS. 9A, 9B, 9C). An unpaired t test was performed. **p<0.005 for wound healing experiment; *p<0.05 for hair growth experiment; n=3-5.

(FIG. 11A) Represents mice on the fourth day of topical application of IMQ and (FIG. 11B) represents a mouse treated with BPD on the 5$^{th}$ day of treatment. The red arrows point at specific erythema (red areas) and the black arrows point at specific scaling (whitish-yellow areas) over time. Note the significant accumulation of IMQ-induced plaque in (FIG. 11A). Compared with mice treated with placebo for 5 days, ApoE$^{-/-}$ treated with 5 mpk BPD for 5 days showed a greater decrease in erythema area (FIG. 11C), a greater decrease in scaling area (FIG. 11D), and a slightly greater increase in hair growth (FIG. 11E). Thus, treatment with BPD reduced inflammation, erythema, scaling and modestly increased hair growth. An unpaired t test was performed. *p<0.05 for erythema experiment; *p<0.05 for scaling experiment; p<0.2895 for hair growth experiment; n=3-5.

13A; p<0.0839) without significantly altering the level of glucosylceramide (FIG. 13C; p<0.7728) and lactosylceramide (FIG. 13B; p<0.2495) in the skin tissue of ApoE-mice fed a high fat and high cholesterol diet. An unpaired t test was used.

Figure 14:
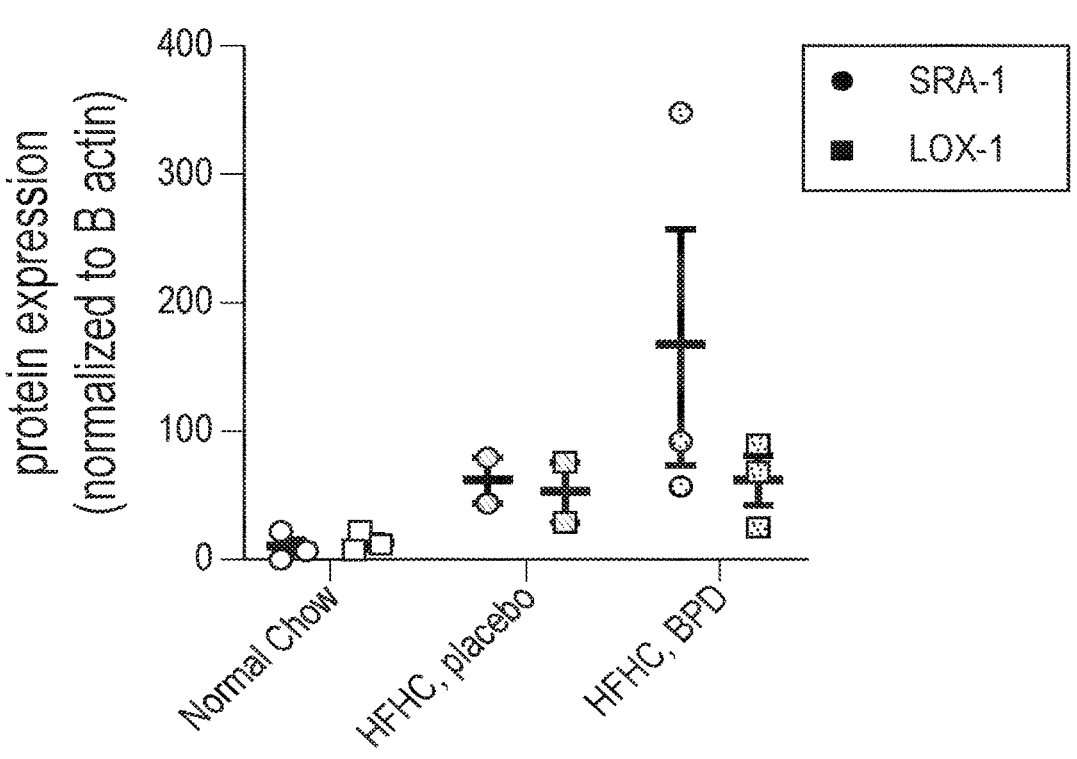

FIG. 14 is a graph showing the expression of scavenger receptor proteins in ApoE$^{-/-}$ mice skin. Western immunoblot assays revealed that feeding a HFHC diet increased the expression of SRA-1 and LOX-1 protein expression in ApoE$^{-/-}$ mice. Treatment with BPD further increased SRA-1 protein expression (N=3, p<0.108).

Figures 15A, 15B, 15C, 15D, 15E, 15F, 15G:
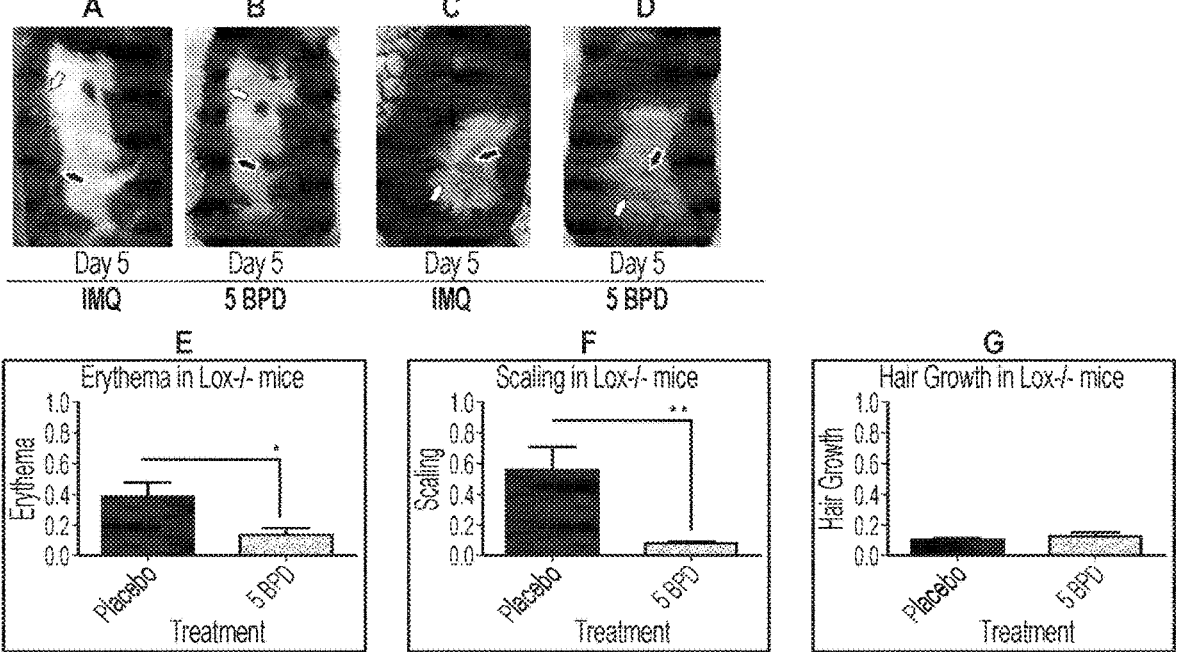

FIGS. 15A-15G are a series of photographs and graphs demonstrating that LOX$^{-/-}$ mice are sensitive to IMQ-induced psoriasis-like pathology which is reversed by treatment with BPD. LOX$^{-/-}$ male (FIGS. 15A, 15B) and female (FIGS. 15C, 15D) mice were fed with normal chow. The dorsal area of mice was shaved using NAIR™. Next, imiquimod (IMQ) was applied topically on to the shaven area daily for 5 days and then treated with 5 mpk BPD daily for 5 days by oral gavage. (FIG. 15A, 15C) represent the mice skin on day 5 of IMQ treatment. (FIGS. 15B, 15D) represent the mice skin on day 5 of BPD treatment. The red arrows point at specific scaling (whitish-yellow areas) and the black arrows point at specific erythema (red areas) over time. Note that BPD treatment significantly diminished both erythema and scaling areas in mice (FIGS. 15E, 15F). However, in mice having topical application of IMQ, BPD did not significantly affect hair growth (FIG. 15G). On the final day of BPD treatment, mice skin showed some blueness, indicating the presence of hair shafts and increased hair pigmentation (FIG. 15B, 15D). An unpaired t test was performed. *p<0.05 for erythema experiment; **p<0.0059 for scaling experiment; p<0.2747 for hair growth experiment; n=3-5.

Figures 16A, 16B:
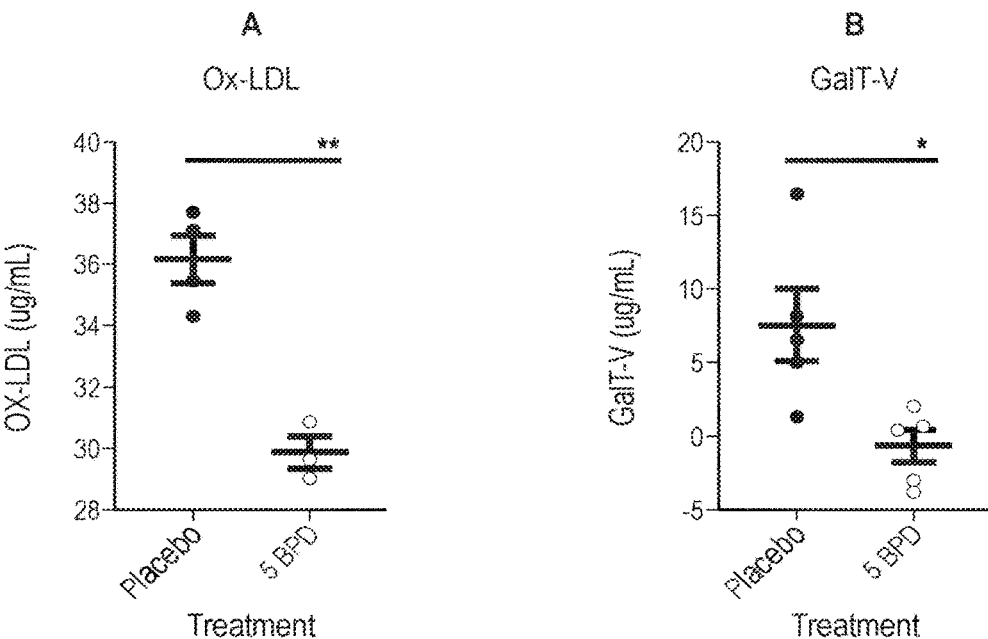

FIGS. 16A and 16B are graphs demonstrating that increased serum levels of Ox-LDL and GalT-V in LOX$^{-/-}$ mice are ameliorated by treatment with BPD. The shaved dorsal areas of male and female LOX$^{-/-}$ mice were subject to 5 consecutive days of IMQ and then 5 days of either placebo or 5 mpk BPD. BPD-treated mice had lower serum levels of Ox-LDL and GalT-V. A parametric two-tailed unpaired t test was performed for each. *p<0.05, **p<0.005.

Figures 17A, 17B, 17C:
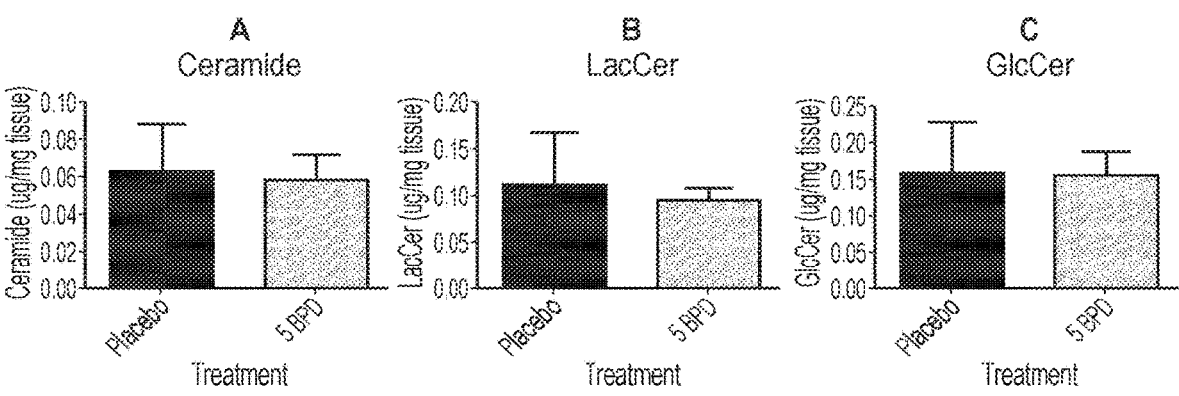

FIGS. 17A-17C are a series of graphs demonstrating that BPD did not significantly affect skin tissue levels of ceramide, lactosylceramide, and GalT-V in LOX-1$^{-/-}$ mice. BPD did not significantly alter the levels of ceramide (FIG. 17A; p<0.9006), lactosylceramide (FIG. 17B; p<0.7542), and glucosylceramide (FIG. 17C; p<0.9749). An unpaired t test was used.

Figure 18:
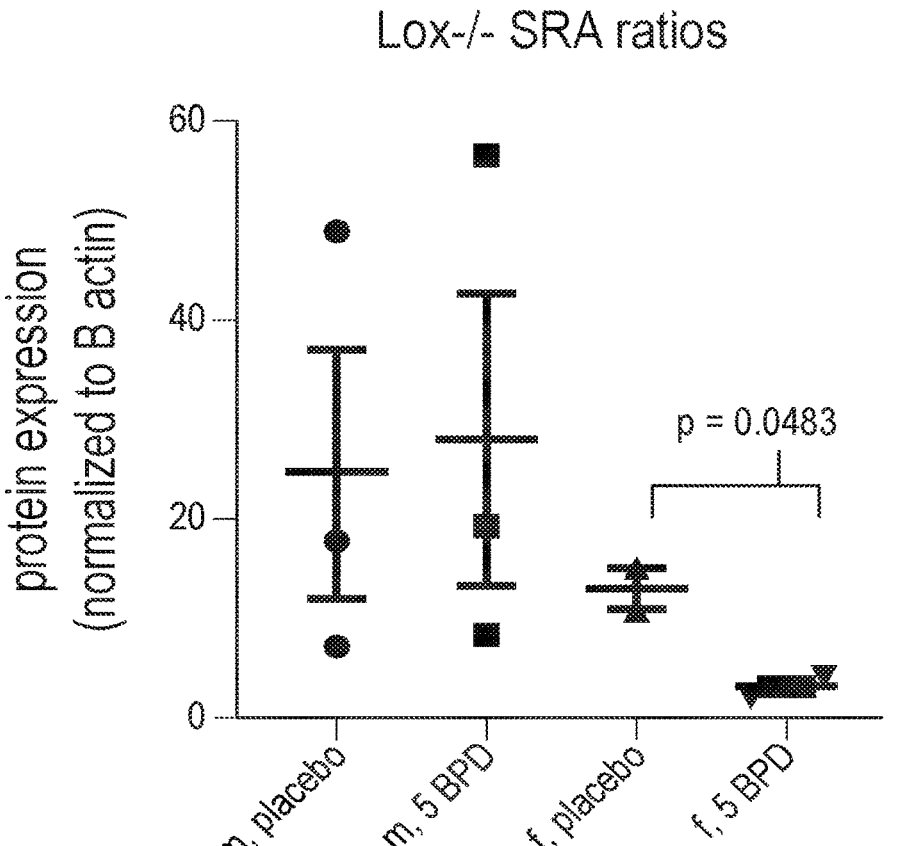

FIG. 18 is a graph demonstrating the expression of scavenger receptor proteins in LOX-1$^{-/-}$ mice skin. This figure shows expression of SRA-1 compared to actin based on Western blot analysis. The effect of BPD seems only significant in the female mice, as the data for the male mice seem independent seem independent of the group, while the average for the female placebo is 4 times higher than the female treatment group, with a statistically significant difference with p-value of 0.0483.

Figures 19A, 19B, 19C, 19D, 19E, 19F, 19G:
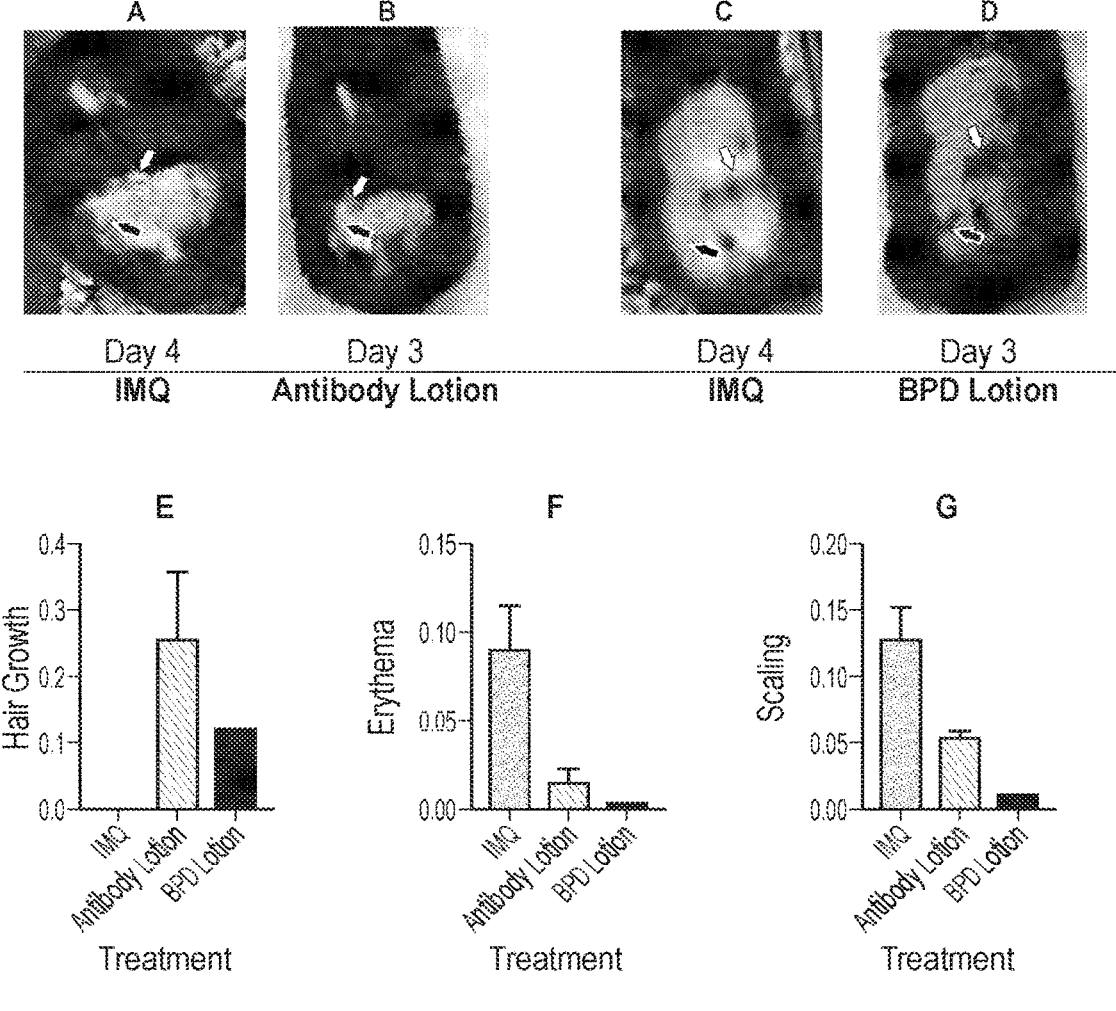

FIGS. 19A-19G are a series of photographs and graphs demonstrating that treatment with GalT-V antibody lotion or BPD lotion (topical application) inhibits erythema and scaling and promotes hair growth in IMQ-treated normal mice. Normal mice were shaved with NAIR™ and treated with IMQ daily for 4 consecutive days. Then, mice were treated with either GalT-V antibody lotion (n=3) or BPD lotion (n=2; however, 1 mice was excluded due to excessively damaged skin). (FIG. 19A) shows the skin of a representative mouse on the fourth day of IMQ application. The black arrows point at a specific erythema area (indicated by redness) and the red arrows point at a specific scaling area (indicated by whiteness/yellowness). By day 3 of treatment, antibody lotion noticeably decreased erythema and scaling areas (FIG. 19B). (FIG. 19C) shows the skin of another mouse on the fourth day of IMQ application. Likewise, by day 3 of treatment, BPD lotion decreased erythema and scaling areas (FIG. 19D). As shown in graph (FIG. 19E), by day 3 of treatment, antibody lotion and BPD lotion resulted in an increase in hair growth when compared to the total bald area of the mice on day 4 of IMQ treatment. Treatment with antibody lotion or BPD lotion also decreased the erythema area and the scaling area compared to the erythema area and the scaling area present on day 4 of IMQ treatment (FIGS. 19F, 19G).

FIGS. 20A-20D is a series of photographs and graphs demonstrating that treatment with BPD increases hair growth in normal mice. FIGS. 20A-20B. Photos of 3 mm mouse skin biopsies after 7 days of continuous treatment with placebo (FIG. 20A) or 2 BPD (FIG. 20B). White arrow denotes hair growth area. FIG. 20C. Change in the number of hairs in normal mice biopsies with and without BPD treatment. *p<0.05, **p<0.01; one-way ANOVA with Tukey post-test. FIG. 20D. Hair growth in live mice with and without BPD treatment over 9 days, measured by the proportion of shaved skin repopulated with hair. *p<0.05.

Figures 21A, 21B, 21C, 21D:
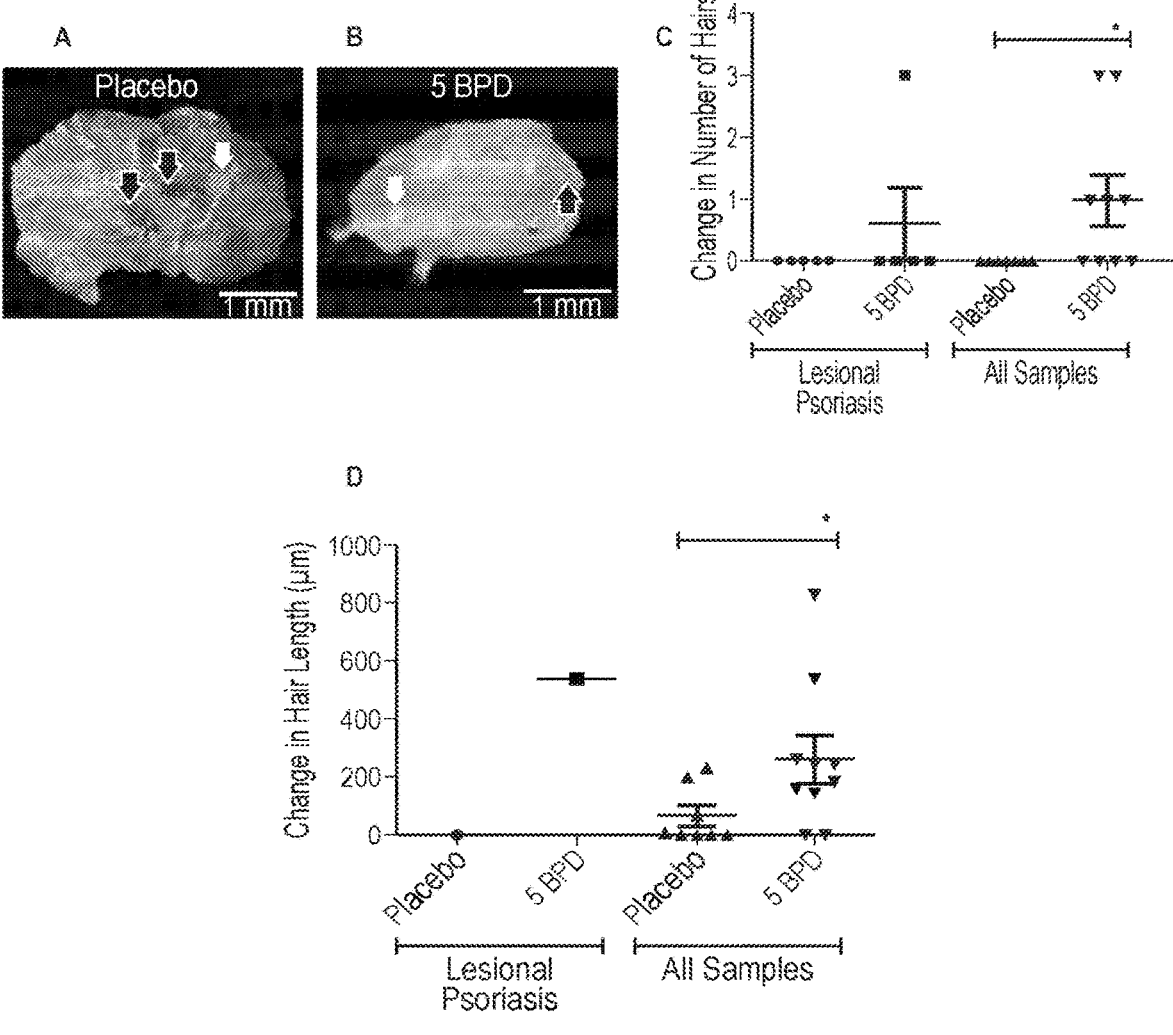

FIGS. 21A-21D is a series of photographs and graphs demonstrating that treatment with BPD increases hair growth in human skin biopsies and may reverse scaling and erythema in lesional areas of skin in patients with psoriasis. FIGS. 21A-21B. Photos of lesional 4 mm skin psoriasis biopsy cut in half and treated with placebo (FIG. 21A) or 5 mpk of BPD (FIG. 21B) for 9 days. Scaling marked with white arrows. Erythema marked with black arrows. FIG. 21C. Scatterplot showing the change in the number of observable hairs of each biopsy after 5-9 days treatment with placebo or 5 BPD, split into lesional psoriasis group and group containing normal and non-lesional psoriasis biopsies. Lesional Psoriasis n=5. All Samples: placebo n=7, 5 BPD n=9. *p<0.05. FIG. 21D. Scatterplot showing the change in the average length of hairs of each biopsy after 5-9 days treatment with placebo or 5 BPD, split into groups as in above. Lesional Psoriasis n=1. All Samples: placebo n=7, 5 BPD n=10. *p<0.05.

Figures 22A, 22B:
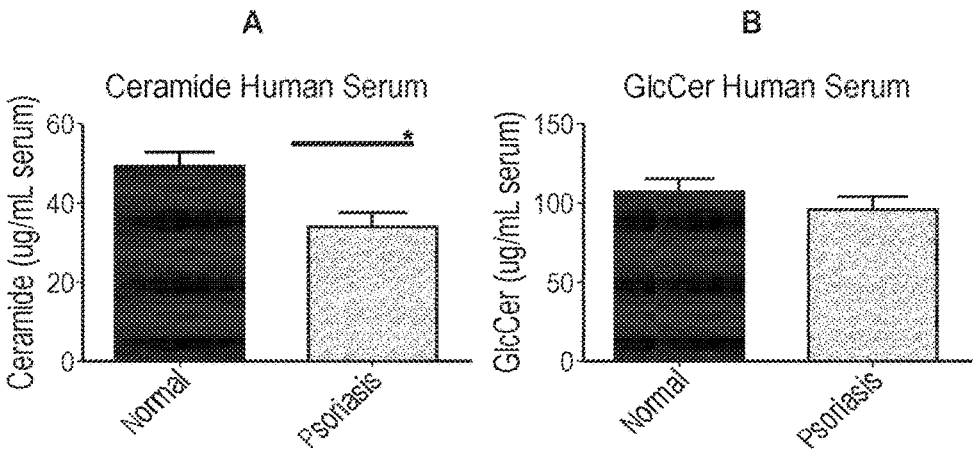

FIGS. 22A, 22B are graphs demonstrating the serum level of ceramide and glucosylceramide in normal human subjects and psoriasis patients. One mL of serum was extracted with organic solvents and the level of ceramide (FIG. 22A) and GlcCer (FIG. 22B) quantified following HPTLC separation and densitometry.

Figures 23A, 23B, 23C:
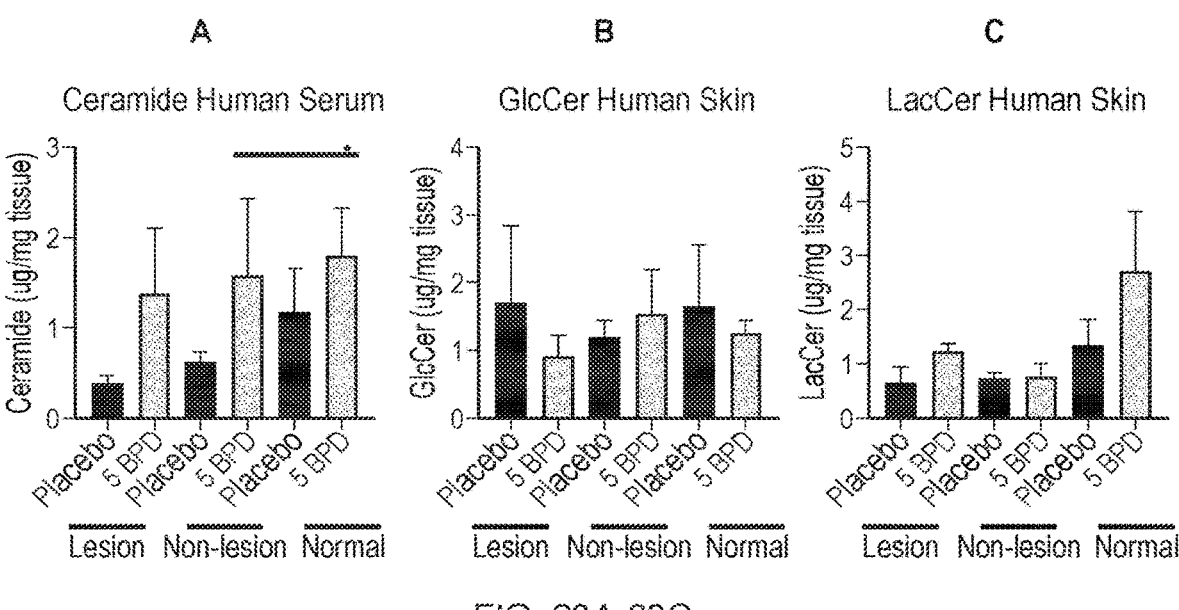

FIGS. 23A-23C are graphs showing the human skin level of ceramides in normal human subjects and psoriasis patients. Frozen skin biopsy tissues were extracted with organic solvents and the level of ceramide (FIG. 23A), glucosylceramide (FIG. 23B), and Lactosylceramide (FIG. 23C) were quantified following HPTLC separation and densitometry. N=5 each for lesional and non-lesional skin biopsies from psoriasis patients and normal subjects.

Figure 24:
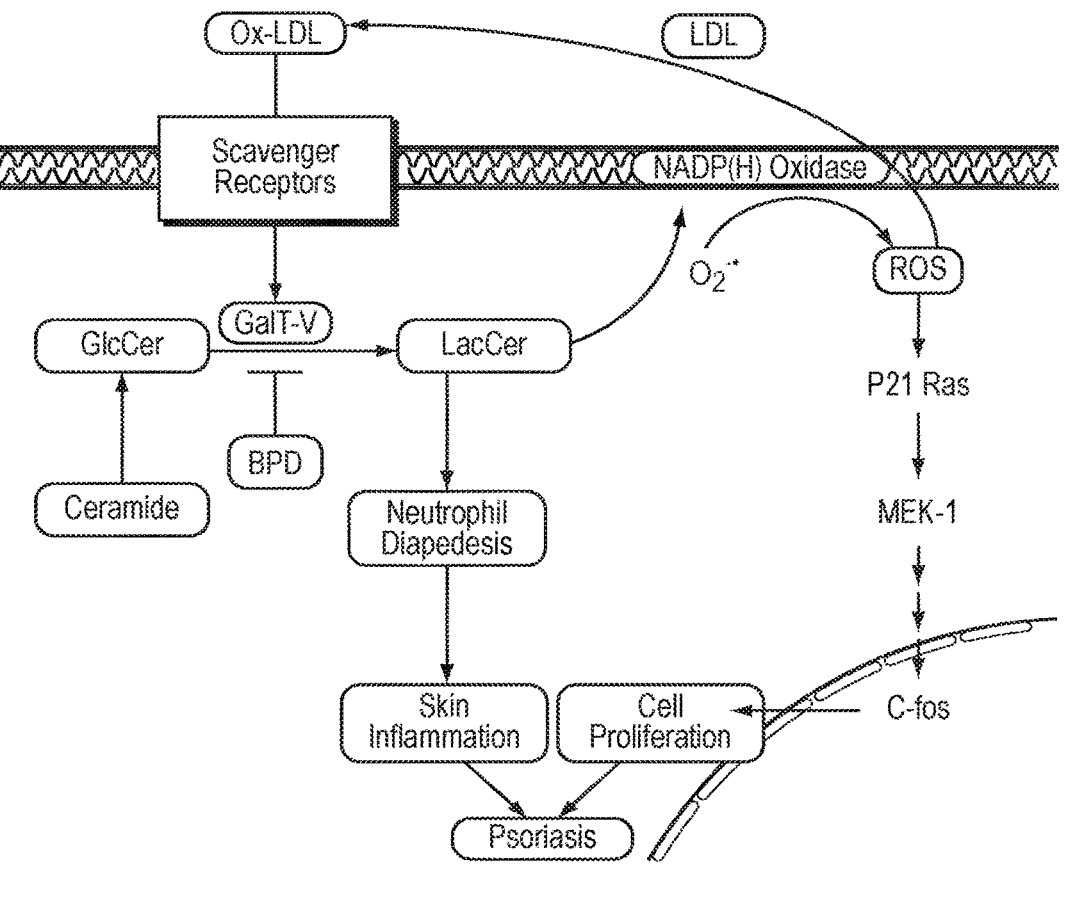

FIG. 24 is a schematic illustration depicting a proposed biochemical pathway by which glycosphingolipids may be involved in psoriasis and its amelioration by treatment with BPD.

DETAILED DESCRIPTION

Normal human skin fibroblasts can not only synthesize GSLs, but also take up GSLs from LDLs, via an LDR receptor-dependent pathway[7]. LDL receptor expression has also been correlated with keratinocyte differentiation[8,9] and barrier function[3]. Keratinocytes also regulate the activity of melanocytes cells responsible for pigmentation of the eye, skin, and hair, thus providing protection from the external environment, including ultraviolet rays[10-14].

The invention is based, in part, on the finding that alterations in skin glycosphingolipid homeostasis affects dermal biology. Applications include compositions for use in treating skin diseases or disorders, inflammatory diseases or disorders and the like.

Skin Diseases, Disorders: Accordingly, in certain embodiments, a method of treating skin inflammation and associated disorders thereof, comprises administering to a subject in need thereof a pharmaceutical composition comprises a therapeutically effective amount of an inhibitor of glycosphingolipid synthesis. In certain embodiments, the pharmaceutical composition increases or replenishes the amounts of skin lipids. Accordingly, in certain embodiments, the pharmaceutical composition comprises D-PDMP, BPD, lipids, ceramides or combinations thereof. In certain embodiments, the pharmaceutical composition comprises D-threo-1-phenyl-2-decanoylamino-3-morpholino-1-propanol (D-PDMP), unencapsulated, unbound or encapsulated in a biodegradable polymer (BPD). In certain embodiments, a composition comprises an inhibitor of glycosphingolipid synthesis, an inhibitor of glucosylceramide synthase or a combination thereof. In certain embodiments, a compound that inhibits glucosylceramide synthesis is an imino sugar. In another embodiment, the imide sugar is N-butyldeoxynojirimycin, N-butyldeoxygalactonojirimycin (NB-DGJ), or N-nonyldeoxynojirimycin. In another embodiment, the inhibitor of glucosylceramide synthesis is 1-phenyl-2-decanoylamino-3-morpholino-1-propanol (DMP), D-threo-1-phenyl-2-decanoylamino-3-morpholino-1-propanol and structurally related analogues thereof. In another embodiment, the inhibitor of glucosylceramide synthesis is 1-phenyl-2-palmitoyl-amino-3-morpholino-1-propanol (PPMP) and structurally related analogues thereof. In certain embodiments, the composition comprises D-threo-1-phenyl-2-decanoylamino-3-morpholino-1-propanol (D-PDMP), (1R,2R)-nonanoic acid[2-(2',3'-dihydro-benzo [1, 4] dioxin-6'-yl)-2-hydroxy-1-pyrrolidin-1-ylmethyl-ethyl]-amide-L-tartaric acid salt (Genz-123346), an imide sugar, 1-phenyl-2-decanoylamino-3-morpholino-1-propanol (DMP), 1-phenyl-2-palmitoyl-amino-3-morpholino-1-propanol (PPMP), lipids, ceramides or combinations thereof are encapsulated by a biodegradable polymer.

In certain embodiments, the composition comprises a therapeutically effective amount of at least one inhibitor of glycosphingolipid synthesis and/or a therapeutically effective amount of the antibody which specifically binds to β1,4-Galactosyltransferase V (BGA), isoforms or peptides thereof.

In certain embodiments, the composition comprises a therapeutically effective amount of at least one inhibitor of glycosphingolipid synthesis and/or a therapeutically effective amount of an agent which modulates the expression or activity of β1,4-Galactosyltransferase V (BGA), isoforms or peptides thereof. In certain embodiments, the agent inhibits the expression or activity of β1,4-Galactosyltransferase V (BGA), isoforms or peptides thereof.

Examples of lipids include, without limitation fatty acids, free fatty acids, cholesterol, sterol esters, triglycerides, diglycerides, glycerides, wax esters, squalene, ceramides, lipids, phospholipids, glycolipids, linoleic acids or combinations thereof.

In other embodiments, a method of inhibiting neutrophil migration to skin wounds and lesions, comprising administering to a subject in need thereof a therapeutically effective amount of an inhibitor of glycosphingolipid synthesis, lipids or combinations thereof.

In certain embodiments, the inhibitor of glycosphingolipid synthesis is D-threo-1-phenyl-2-decanoylamino-3-morpholino-1-propanol (D-PDMP), unencapsulated, unbound or encapsulated in a biodegradable polymer (BPD).

In certain embodiments, the biodegradable polymer consists of polyethylene glycol and sebacic acid.

In certain embodiments, the skin disease or skin associated disorders comprise inflammatory skin diseases, burns, scars, wounds, lesions, autoimmune diseases, Verucca vulgaris, fungal infections, bacterial infections, virus infections, rosacea or combinations thereof. The scars can be from an injury or as a result of surgery, including cosmetic surgery. In certain embodiments, the inflammatory skin disease, condition or lesion is selected from a group comprising eczema, psoriasis, atopic dermatitis, lichen planus, bullous pemphigoid, vasculitis, granuloma annulare, acne, keloid formation, abnormalities in skin pigmentation, solar keratosis, solar elastosis, wound healing, epithelial inflammation, dermatitis, skin cancer and cosmetic indications, or any combination thereof.

In certain embodiments, the compositions are used to treat burns whether localized or whether the burns cover most of the subject's body.

In certain embodiments, the compositions embodied herein are used to treat disorders associated with skin diseases comprising: psoriasis, erythema, redness, induration, thickness, desquamation, scaling, red patches of skin covered with silvery scales, small scaling spots, dry skin, cracked skin that may bleed, itching, burning, soreness, or combinations thereof.

Psoriasis is a long-lasting autoimmune disease which is characterized by patches of abnormal, inflamed skin. These skin patches are typically red, itchy, and scaly. They may vary in severity from small and localized to complete body coverage. Injury to the skin can trigger psoriatic skin changes at that spot, which is known as the Koebner phenomenon. Psoriasis is generally thought to be a genetic disease which is triggered by environmental factors. The disease affects 2-4% of the population and may begin at any age but usually starts in adulthood. There is no cure for psoriasis.

Two major immune system genes under investigation for psoriasis linkage are interleukin-12 subunit beta (IL12β) on chromosome 5q, which expresses interleukin-12β; and IL23R on chromosome 1p, which expresses the interleukin-23 receptor, and is involved in T cell differentiation. Interleukin-23 receptor and IL12β have both been strongly linked with psoriasis. T cells are involved in the inflammatory process that leads to psoriasis. These genes are on the pathway that upregulate tumor necrosis factor-α and nuclear factor κB; two genes involved in inflammation. Recently, the first gene directly linked to psoriasis has been identified. A rare mutation in the gene encoding for the CARD14 protein plus an environmental trigger was sufficient to cause plaque psoriasis (the most common form of psoriasis). Psoriasis is known to be associated with an up-regulation of $T_H1$ and $T_H17$ cytokines and a relative down-regulation of $T_H2$ and T-regulatory (T-reg) cytokines.

In certain embodiments, one or more anti-inflammatory agents, steroidal drugs or non-steroidal anti-inflammatory drugs (NSAIDS), antibiotics, antibodies, wound healing agents, cytokines, cannabinoids, or combinations thereof are administered to the subject.

In certain embodiments, the inhibitor of glycosphingolipid synthesis is formulated for oral or topical administration. In certain embodiments the formulation comprises one or more anti-inflammatory agents, steroidal drugs or non-steroidal anti-inflammatory drugs (NSAIDS), wound healing agents, cytokines, cannabinoids, antibodies, anti-viral agents, anti-fungal agents or combinations thereof. In certain embodiments, the topical administration comprises use of a cream, gel, ointment, spray, lip-balm, balm, emulsion, liposome, liquid crystal preparation or lotion, or any combination thereof. In certain embodiments, a pharmaceutical composition comprises D-PDMP, BPD, lipids, ceramides or combinations thereof. In certain embodiments, the pharmaceutical composition comprises D-threo-1-phenyl-2-decanoylamino-3-morpholino-1-propanol (D-PDMP), unencapsulated, unbound or encapsulated in a biodegradable polymer (BPD). In certain embodiments, a composition comprises an inhibitor of glycosphingolipid synthesis, an inhibitor of glucosylceramide synthase or a combination thereof. In certain embodiments, a compound that inhibits glucosylceramide synthesis is an imino sugar. In another embodiment, the imide sugar is N-butyldeoxynojirimycin, N-butyldeoxygalactonojirimycin (NB-DGJ), or N-nonyldeoxynojirimycin. In another embodiment, the inhibitor of glucosylceramide synthesis is 1-phenyl-2-decanoylamino-3-morpholino-1-propanol (DMP), D-threo-1-phenyl-2-decanoylamino-3-morpholino-1-propanol and structurally related analogues thereof. In another embodiment, the inhibitor of glucosylceramide synthesis is 1-phenyl-2-palmitoyl-amino-3-morpholino-1-propanol (PPMP) and structurally related analogues thereof. In certain embodiments, the composition comprises D-threo-1-phenyl-2-decanoylamino-3-morpholino-1-propanol (D-PDMP), (1R,2R)-nonanoic acid[2-(2',3'-dihydro-benzo [1, 4] dioxin-6'-yl)-2-hydroxy-1-pyrrolidin-1-ylmethyl-ethyl]-amide-L-tartaric acid salt (Genz-123346), an imide sugar, 1-phenyl-2-decanoylamino-3-morpholino-1-propanol (DMP), 1-phenyl-2-palmitoyl-amino-3-morpholino-1-propanol (PPMP), lipids, ceramides or combinations thereof are encapsulated by a biodegradable polymer. Examples of lipids include, without limitation fatty acids, free fatty acids, cholesterol, sterol esters, triglycerides, diglycerides, glycerides, wax esters, squalene, ceramides, lipids, phospholipids, glycolipids, linoleic acids or combinations thereof.

The compositions of the present invention may also include an anti-inflammatory drug, a topical anesthetic or a combination thereof. Typical topical anesthetics include, but are not limited to, lidocaine, xylocaine, buprenorphine and fentanyl. Suitable topical anesthetics are known to those of skill in the art and are disclosed, e.g., in Goodman Gilman, Alfred; Goodman, Louis S.; Gilman, Alfred; Goodman and Gilman's The Pharmacological Basis of Therapeutics, Ninth Edition, pp. 331-347.

Any suitable topical corticosteroid can be employed as an anti-inflammatory drug. Suitable corticosteroids are known to those of skill in the art and are disclosed in, e.g., Goodman Gilman, Alfred; Goodman, Louis S.; Gilman, Alfred; Goodman and Gilman's The Pharmacological Basis of Therapeutics, Ninth Edition, pp. 1459-1483. Suitable exemplary corticosteroids include cortisol (hydrocortisone); tetrahydrocortisol; prednisone (cortisone); prednisolone (cortisol); 6α-methylprednisolone; fludrocortisone (9α-fluorocortisol); 11-desoxycortisol; cortisone (11-dehydrocortisol); corticosterone; triamcinolone (9α-fluoro-16α-hydroxyprednisolone); paramethasone (6α-fluoro-16α-methylprednisolone); betamethasone (9α-fluoro-16β-methylprednisolone); dexamethasone (9α-fluoro-16α-methylprednisolone); desoxycorticosterone acetate (doca acetate, percorten acetate); desoxycorticosterone pivalate (percorten pivalate); fludrocortisone acetate (florine acetate); cortisol (hydrocortisone) (cortef, hydrocortone); cortisol acetate (cortef acetate, hydrocortone acetate); cortisol cypionate (cortef); cortisol sodium phosphate (hydrocortone phosphate); cortisol sodium succinate (solu-cortef); beclopmethasone dipropionate (vanceril); betamethasone (celestone); betamethasone sodium phosphate and acetate (celestone soluspan); betamethasone dipropionate (diprosone); betamethasone valerate (valisone); betamethasone benzoate (benisone, flurodate); cortisone acetate (cortone acetate); dexamethasone (decadron, gammacorten); dexamethasone sodium phosphate (decadron phosphate, hexadrol phosphate); dexamethasone acetate (decadron-L.A.); fuprednisolone (alphadrol); meprednisone (betapar); methylprednisolone (medrol); methylprednisolone acetate (depo-medrol, medrol acetate); methylprednisolone sodium succinate (solu-medrol); paramethasone acetate (haldrone); prednisolone (delta-cortef); prednisolone acetate (meticortelone acetate); prednisolone sodium phosphate (hydeltrasol); prednisolone sodium succinate (meticortelone soluble); prednisolone tebutate (hydelta-T.B.A.); prednisone (deltasone, paracort); triamcinolone (aristocort, kenacort); triamcinolone acetonide (aristoderm, kenalog); triamcinolone diacetate (aristocort diacetate, kienacort diacetate); triamcinolone hexacotonide (aristospan); desonide (tridesilon); desoximetasone (topicort); flumethasone pivalate (locorten); fluocinolone acetonide (fluonid, synalar); fluocinonide (lidex, topsyn); fluorometholone (oxylone); flurandrenolide (cordran); halcinonide (halog); and medrysone (HMS liquifilm, medrocort).

The amount of a suitable topical anti-inflammatory or topical anesthetic can be present in about 0.1 wt % to about 99.9 wt % of the composition. Typically, the amount of anesthetic and/or anti-inflammatory present will depend upon the specific anesthetic and anti-inflammatory employed in the composition. In some embodiments of the present invention, the anesthetic and/or anti-inflammatory can be up to about 10 wt %, up to about 5 wt %, up to about 2 wt %, up to about 1 wt % or up to about 0.1 wt % of the composition. Additionally, the nature and amount of the anesthetic and/or anti-inflammatory present in the composition should comply with any State and/or Federal guidelines that regulate the use of such compounds (e.g., FDA regulations).

The compositions of the present invention may also include known psoriasis treatment agents such as anthralin, also known as dithranol, vitamin D such as calcipotriene or calcitriol, and vitamin A such as tazarotene. Some of the known psoriasis treatment agents are described in greater detail in Goodman Gilman, Alfred; Goodman, Louis S.; Gilman, Alfred; Goodman and Gilman's The Pharmacological Basis of Therapeutics, Ninth Edition, pp. 1591-1613.

Hair Loss, Discoloration: Disturbance of the Notch pathway[26-32] by inactivating of Notch1, Notch2, or RBP-Jk in melanocyte lineage using Tyr::Cre transgenic mice resulted in gene dosage-dependent hair graying, with pronounced effect in mice deficient in both Notch 1 and Notch 2[33-35].

Most recent studies on mice deficient in stem cell factor in the transcription factor called krox20 lineage that exhibit hair graying exposed the identities of hair matrix progenitors which regulate hair growth and pigmentation[36] and creating a stem cell factor-dependent niche for follicular melanocytes[36].

In certain embodiments, a method of preventing and/or reversing hair discoloration comprising administering to a subject in need thereof a therapeutically effective amount of an inhibitor of glycosphingolipid synthesis, lipids and combinations thereof. Accordingly, in certain embodiments, a pharmaceutical composition comprises D-PDMP, BPD, lipids, ceramides or combinations thereof. In certain embodiments, the pharmaceutical composition comprises D-threo-1-phenyl-2-decanoylamino-3-morpholino-1-propanol (D-PDMP), unencapsulated, unbound or encapsulated in a biodegradable polymer (BPD). In certain embodiments, a composition comprises an inhibitor of glycosphingolipid synthesis, an inhibitor of glucosylceramide synthase or a combination thereof. In certain embodiments, a compound that inhibits glucosylceramide synthesis is an imino sugar. In another embodiment, the imide sugar is N-butyldeoxynojirimycin, N-butyldeoxygalactonojirimycin (NB-DGJ), or N-nonyldeoxynojirimycin. In another embodiment, the inhibitor of glucosylceramide synthesis is 1-phenyl-2-decanoylamino-3-morpholino-1-propanol (DMP), D-threo-1-phenyl-2-decanoylamino-3-morpholino-1-propanol and structurally related analogues thereof. In another embodiment, the inhibitor of glucosylceramide synthesis is 1-phenyl-2-palmitoyl-amino-3-morpholino-1-propanol (PPMP) and structurally related analogues thereof. In certain embodiments, the composition comprises D-threo-1-phenyl-2-decanoylamino-3-morpholino-1-propanol (D-PDMP), (1R,2R)-nonanoic acid[2-(2',3'-dihydro-benzo [1, 4] dioxin-6'-yl)-2-hydroxy-1-pyrrolidin-1-ylmethyl-ethyl]-amide-L-tartaric acid salt (Genz-123346), an imide sugar, 1-phenyl-2-decanoylamino-3-morpholino-1-propanol (DMP), 1-phenyl-2-palmitoyl-amino-3-morpholino-1-propanol (PPMP), lipids, ceramides or combinations thereof are encapsulated by a biodegradable polymer. Examples of lipids include, without limitation fatty acids, free fatty acids, cholesterol, sterol esters, triglycerides, diglycerides, glycerides, wax esters, squalene, ceramides, lipids, phospholipids, glycolipids, linoleic acids or combinations thereof.

In certain embodiments, a method of preventing and/or reversing hair loss comprising administering to a subject in need thereof a therapeutically effective amount of one or more inhibitors of glycosphingolipid synthesis, one or more lipids, ceramides, an agent inhibits the expression or activity of β1,4-Galactosyltransferase V (BGA) or combinations thereof. In certain embodiments, the hair loss is Alopecia aerata.

Inflammatory Diseases or Disorders: In certain embodiments, the compositions are administered to subjects having an inflammatory disease. These include, systemic and/or chronic inflammatory diseases including autoimmune diseases. Inflammatory and autoimmune pathologies, in particular antibody-mediated diseases, can be severe and chronic. Chronic inflammatory diseases are for example autoimmune inflammatory diseases, rheumatology diseases like inflammation of connective and vascular tissues. For example, diseases that can be treated with MVs according to the present invention are the following: systemic vasculitis, polyarteritis nodosa, giant cell arteritis, Wegener's granulomatosis, Henoch-Schonlein purpura, cryoglobulinaemia, central nervous system vasculitis, multiplex mononeuritis, Takayasu's arteritis, Behcet's disease, Buerger's disease, intestinal chronic inflammatory diseases, as for example Crohn's disease, inflammatory bowel disease and ulcerative colitis, Hashimoto's thyroiditis, autoimmune hemolytic anemia, Addison's disease, diabetes mellitus Type I, adult late-onset autoimmune diabetes (LADA), recurrent autoimmune diabetes in long-standing diabetes patients after receiving pancreas or islet transplantation, rheumatoid arthritis, systemic lupus erythematosus, dermatomyositis, scleroderma, Sjogren's syndrome, multiple sclerosis, chronic autoimmune hepatitis, primary biliary cirrhosis, psoriasis, alopecia areata, vitiligo, Goodpasture's syndrome, Guillame-Barre's syndrome, chronic glomerulonephritis, dermatitis and eczema, Reiter's syndrome, reactive arthritis, cystic fibrosis, sinusitis, chronic bronchitis, periodontal disease, diverticulosis/diverticulitis.

In certain embodiments, a method of preventing and/or treating inflammatory diseases or disorders thereof, comprises administering to a subject in need thereof a pharmaceutical composition comprising a therapeutically effective amount of an inhibitor of glycosphingolipid synthesis. In certain embodiments, the composition comprises a therapeutically effective amount of at least one inhibitor of glycosphingolipid synthesis and/or a therapeutically effective amount of an agent which modulates the expression or activity of β1,4-Galactosyltransferase V (BGA), isoforms or peptides thereof. In certain embodiments, the agent inhibits the expression or activity of β1,4-Galactosyltransferase V (BGA), isoforms or peptides thereof. In certain embodiments, the agent is an antibody.

Pharmaceutical Formulations

In some embodiments, a topical composition of the present invention comprises a therapeutically effective amount of inhibitor of glycosphingolipid synthesis, such as, for example, D-threo-1-phenyl-2-decanoylamino-3-morpholino-1-propanol (D-PDMP), unencapsulated, unbound or encapsulated in a biodegradable polymer (BPD); an oil phase comprising at least one penetration enhancing agent, a non-polymeric thickening agent; and an aqueous phase. In certain embodiments, the pharmaceutical composition comprises D-threo-1-phenyl-2-decanoylamino-3-morpholino-1-propanol (D-PDMP), unencapsulated, unbound or encapsulated in a biodegradable polymer (BPD). In certain embodiments, a composition comprises an inhibitor of glycosphingolipid synthesis, an inhibitor of glucosylceramide synthase or a combination thereof. In certain embodiments, a compound that inhibits glucosylceramide synthesis is an imino sugar. In another embodiment, the imide sugar is N-butyldeoxynojirimycin, N-butyldeoxygalactonojirimycin (NB-DGJ), or N-nonyldeoxynojirimycin. In another embodiment, the inhibitor of glucosylceramide synthesis is 1-phenyl-2-decanoylamino-3-morpholino-1-propanol (DMP), D-threo-1-phenyl-2-decanoylamino-3-morpholino-1-propanol and structurally related analogues thereof. In another embodiment, the inhibitor of glucosylceramide synthesis is 1-phenyl-2-palmitoyl-amino-3-morpholino-1-propanol (PPMP) and structurally related analogues thereof. In certain embodiments, the composition comprises D-threo-1-phenyl-2-decanoylamino-3-morpholino-1-propanol (D-PDMP), (1R,2R)-nonanoic acid[2-(2',3'-dihydro-benzo [1, 4] dioxin-6'-yl)-2-hydroxy-1-pyrrolidin-1-ylmethyl-ethyl]-amide-L-tartaric acid salt (Genz-123346), an imide sugar, 1-phenyl-2-decanoylamino-3-morpholino-1-propanol (DMP), 1-phenyl-2-palmitoyl-amino-3-morpholino-1-propanol (PPMP), lipids, ceramides or combinations thereof are encapsulated by a biodegradable polymer. Examples of penetration enhancing agent include, without limitation, polyols, glycols (except propylene glycol), ethers, glycol ethers, esters, sulfoxides, fatty acids, fatty acid esters, essential oils, terpenes, terpenoids, PEGylated fatty acids, PEGylated fatty acid esters and mixtures thereof nitrogenous compounds, alkanones, organic acids, and combinations thereof.

In certain embodiments, the composition comprises a therapeutically effective amount of at least one inhibitor of glycosphingolipid synthesis and/or a therapeutically effective amount of an agent which modulates the expression or activity of β1,4-Galactosyltransferase V (BGA), isoforms or peptides thereof. In certain embodiments, the agent inhibits the expression or activity of β1,4-Galactosyltransferase V (BGA), isoforms or peptides thereof. In certain embodiments, the agent is an antibody.

In certain embodiments, the method of treating skin inflammation or diseases thereof, comprises increasing the or supplementing the amount of ceramides. Accordingly, in certain embodiments, a pharmaceutical composition comprises D-PDMP, BPD, lipids or combinations thereof. Examples of lipids include, without limitation fatty acids, free fatty acids, cholesterol, sterol esters, triglycerides, diglycerides, glycerides, wax esters, squalene, ceramides, lipids, phospholipids, glycolipids, linoleic acids or combinations thereof.

In certain embodiments, the pharmaceutical compositions comprise ceramide to lipid ratios from about 1:1 to at least about 10:1. In one embodiment, the composition comprises cholesterol:free fatty acids:ceramide:BPD 1 mpk-10 mpk (3:1:1: 1 mpk-10 mpk).

In certain embodiments, a pharmaceutical composition for systemic administration, e.g. oral, i.v., i.m, etc., comprises a therapeutically effective amount of inhibitor of glycosphingolipid synthesis, such as, for example, D-threo-1-phenyl-2-decanoylamino-3-morpholino-1-propanol (D-PDMP), unencapsulated, unbound or encapsulated in a biodegradable polymer (BPD, or combinations thereof.

The pharmaceutical compositions may include a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, olive oil, gel (e.g., hydrogel), and the like. Saline is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin, the contents of which are hereby incorporated by reference in its entirety. Such compositions will generally contain a therapeutically effective amount of the pharmaceutical agents and/or therapeutic compounds (e.g., biopolymer encapsulated D-PDMP), in purified form, together with a suitable amount of carrier so as to provide the form for proper administration to the patient. The formulation should suit the mode of administration.

In embodiments, the pharmaceutical agents and/or therapeutic compounds are administered locally as an immediate release or controlled release composition, for example by controlled dissolution and/or the diffusion of the active substance. Dissolution or diffusion controlled release can be achieved by incorporating the active substance into an appropriate matrix. A controlled release matrix may include one or more of a biopolymer, shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols and/or sebacic acid. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon. In certain embodiments, the controlled release composition is achieved via a transdermal patch.

The controlled release matrix may also be a hydrogel: a three-dimensional, hydrophilic or amphiphilic polymeric network capable of taking up large quantities of water. The networks may be composed of homopolymers or copolymers, which are insoluble due to the presence of covalent chemical or physical (e.g., ionic, hydrophobic interactions, entanglements) crosslinks. The crosslinks provide the network structure and physical integrity. Hydrogels exhibit a thermodynamic compatibility with water that allows them to swell in aqueous media. The chains of the network are connected in such a fashion that pores exist and that a substantial fraction of these pores are of dimensions between 1 nm and 1000 nm.

The hydrogels can be prepared by crosslinking hydrophilic biopolymers or synthetic polymers. Examples of the hydrogels formed from physical or chemical crosslinking of hydrophilic biopolymers, include but are not limited to, hyaluronans, chitosans, alginates, collagen, dextran, pectin, carrageenan, polylysine, gelatin, agarose, (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly (methacrylates), poly(N-vinylpyrrolidone), PL(G)A-PEO-PL(G)A copolymers, poly(ethylene imine), and the like. See Hennink and van Nostrum, *Adv. Drug Del. Rev.* 54:13-36 (2002); Hoffman, *Adv. Drug Del. Rev.* 43:3-12 (2002); Cadee et al., *J Control. Release* 78:1-13 (2002); Surini et al., *J. Control. Release* 90:291-301 (2003); and U.S. Pat. No. 7,968,085, each of which is incorporated by reference in its entirety. These materials consist of high-molecular weight backbone chains made of linear or branched polysaccharides or polypeptides.

In certain embodiments, the compositions embodied herein are administered via a transdermal patch. Transdermal patch delivery is an alternate method of delivering potent medicines. Patch delivery circumvents the gastric system and therefore the medical substance is not subject to the digestive system of the liver first-pass effect. Children, the elderly, and those with compromised immune systems or those who are taking multiple medications who are most vulnerable to organ damage from ingested substances, would benefit from using transdermal patch delivery that provides a safe, controlled and sustained delivery of the compositions for at least 24 hours and up to 72 hours.

The amount of the pharmaceutical composition of the invention which will be effective in the treatment or prevention of atherosclerotic heart disease can be determined by standard clinical techniques. In addition, in vitro assays may optionally be employed to help identify optimal dosage ranges. The precise dose to be employed in the formulation may also depend on the route of administration, and the seriousness of the disease, and should be decided according to the judgment of the practitioner and each patient's circumstances. Effective doses may be extrapolated from dose-response curves derived from the in vitro or animal model test systems described herein or known to one of skill in the art.

Dosages and Administration Regimens

The pharmaceutical agents and/or therapeutic compounds or compositions containing these agents/compounds may be administered in a manner compatible with the dosage formulation, and in such amount as may be therapeutically affective, protective and immunogenic.

The agents and/or compositions may be administered through different routes, including, but not limited to, oral, oral gavage, parenteral, buccal and sublingual, rectal, aerosol, nasal, intramuscular, subcutaneous, intradermal, intraosseous, dermal, and topical. The term parenteral as used herein includes, for example, intraocular, subcutaneous, intraperitoneal, intracutaneous, intravenous, intramuscular, intraarticular, intraarterial, intrasynovial, intrasternal, intrathecal, intralesional, and intracranial injection, or other infusion techniques.

In embodiments, the pharmaceutical agents and/or therapeutic compounds formulated according to the present invention are formulated and delivered in a manner to evoke a systemic response. Thus, in embodiments, the formulations are prepared by uniformly and intimately bringing into association the active ingredient with liquid carriers. Formulations suitable for administration include aqueous and non-aqueous sterile solutions, which may contain anti-oxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water, immediately prior to use. Extemporaneous solutions and suspensions may be prepared from sterile powders, granules and tablets commonly used by one of ordinary skill in the art.

The agents and/or compositions may be administered in different forms, including, but not limited to, solutions, emulsions and suspensions, microspheres, particles, microparticles, nanoparticles, liposomes, and the like.

The pharmaceutical agents and/or therapeutic compounds may be administered in a manner compatible with the dosage formulation, and in such amount as may be therapeutically effective, immunogenic and protective. The quantity to be administered depends on the subject to be treated, including, for example, the stage of the disease. Precise amounts of active ingredients required to be administered depend on the judgment of the practitioner. However, suitable dosage ranges are readily determinable by one skilled in the art and may be of the order of micrograms to milligrams of the active ingredient(s) per dose. The dosage may also depend on the route of administration and may vary according to the size of the host.

The pharmaceutical agents and/or therapeutic compounds should be administered to a subject in an amount effective to ameliorate, treat, and/or prevent the disease. Specific dosage and treatment regimens for any particular subject may depend upon a variety of factors, including the activity of the specific compound employed, the age, body weight, general health status, sex, diet, time of administration, rate of excretion, drug combination, the severity and course of the disease (including tumor size), condition or symptoms, the subject's disposition to the disease, condition or symptoms, method of administration, and the judgment of the treating physician. Actual dosages can be readily determined by one of ordinary skill in the art.

Exemplary unit dosage formulations are those containing a dose or unit, or an appropriate fraction thereof, of the administered ingredient. It should be understood that in addition to the ingredients mentioned herein, the formulations of the present invention may include other agents commonly used by one of ordinary skill in the art.

In certain embodiments, the antibody which specifically binds to $\beta$1,4-Galactosyltransferase V (BGA), isoforms or peptides thereof is administered systemically or topically.

In certain embodiments, a composition comprising D-threo-1-phenyl-2-decanoylamino-3-morpholino-1-propanol (D-PDMP), (1R,2R)-nonanoic acid[2-(2',3'-dihydrobenzo [1, 4] dioxin-6'-yl)-2-hydroxy-1-pyrrolidin-1-ylmethyl-ethyl]-amide-L-tartaric acid salt (Genz-123346), an imide sugar, 1-phenyl-2-decanoylamino-3-morpholino-1-propanol (DMP), 1-phenyl-2-palmitoyl-amino-3-morpholino-1-propanol (PPMP), lipids, ceramides or combinations thereof are unencapsulated or encapsulated by a biodegradable polymer is administered systemically or topically.

In certain embodiments, the composition comprising a therapeutically effective amount of at least one inhibitor of glycosphingolipid synthesis and/or a therapeutically effective amount of an agent which modulates the expression or activity of $\beta$1,4-Galactosyltransferase V (BGA), isoforms or peptides thereof is administered systemically or topically.

In certain embodiments, the composition comprising a therapeutically effective amount of at least one inhibitor of glycosphingolipid synthesis and/or a therapeutically effective amount of an agent which modulates the expression or activity of $\beta$1,4-Galactosyltransferase V (BGA), isoforms or peptides thereof is co-administered to the subject. The term "co-administer" refers to the simultaneous presence of two active agents in the blood of an individual. Active agents that are co-administered can be concurrently or sequentially delivered.

Typically in conventional systemically administered treatments, a therapeutically effective dosage should produce a serum concentration of compound of from about 0.1 ng/ml to about 50-100 µg/ml. The pharmaceutical compositions typically provide a dosage of from about 0.001 mg to about 2000 mg of compound per kilogram of body weight per day. For example, dosages for systemic administration to a human patient can range from 1-10 µg/kg, 20-80 µg/kg, 5-50 µg/kg, 75-150 µg/kg, 100-500 µg/kg, 250-750 µg/kg, 500-1000 µg/kg, 1-10 mg/kg, 5-50 mg/kg, 25-75 mg/kg, 50-100 mg/kg, 100-250 mg/kg, 50-100 mg/kg, 250-500 mg/kg, 500-750 mg/kg, 750-1000 mg/kg, 1000-1500 mg/kg, 1500-2000 mg/kg, 5 mg/kg, 20 mg/kg, 50 mg/kg, 100 mg/kg, 500 mg/kg, 1000 mg/kg, 1500 mg/kg, or 2000 mg/kg. In an exemplary embodiment, an oral dosage for a human weighing 200 kg would be about 200 mg/day. Pharmaceutical dosage unit forms are prepared to provide from about 1 mg to about 5000 mg, for example from about 100 to about 2500 mg of the compound or a combination of essential ingredients per dosage unit form.

In general, a therapeutically effective amount of the present compounds in dosage form usually ranges from slightly less than about 0.025 mg/kg/day to about 2.5 g/kg/day, preferably about 0.1 mg/kg/day to about 100 mg/kg/day of the patient or considerably more, depending upon the compound used, the condition or infection treated and the route of administration, although exceptions to this dosage range may be contemplated by the present invention. It is to be understood that the present invention has application for both human and veterinary use.

The agents and/or compositions are administered in one or more doses as required to achieve the desired effect. Thus, the agents and/or compositions may be administered in 1, 2, to 3, 4, 5, or more doses. Further, the doses may be separated by any period of time, for example hours, days, weeks, months, and years.

The agents and/or compositions can be formulated as liquids or dry powders, or in the form of microspheres.

The agents and/or compositions may be stored at temperatures of from about −100° C. to about 25° C. depending on the duration of storage. The agents and/or compositions may also be stored in a lyophilized state at different temperatures including room temperature. The agents and/or compositions may be sterilized through conventional means known to one of ordinary skill in the art. Such means include, but are not limited to, filtration. The composition may also be combined with other anti-atherosclerotic therapeutic agents.

The amount of active ingredient that may be combined with carrier materials to produce a single dosage form may vary depending upon the host treated and the particular mode of administration. In embodiments, a preparation may contain from about 0.1% to about 95% active compound (w/w), from about 20% to about 80% active compound, or from any percentage therebetween.

In embodiments, the pH of the formulation may be adjusted with pharmaceutically acceptable acids, bases, or buffers to enhance the stability of the formulated compound or its delivery form.

In embodiments, the pharmaceutical carriers may be in the form of a sterile liquid preparation, for example, as a sterile aqueous or oleaginous suspension. Among the acceptable vehicles and solvents that may be employed are mannitol, water, Ringer's solution and isotonic sodium chloride solution.

In addition, sterile, fixed oils are conventionally employed as a solvent or suspending medium. For this purpose, any bland fixed oil may be employed including synthetic mono- or to diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions.

Other commonly used surfactants such as TWEEN™ or SPAN™ and/or other similar emulsifying agents or bioavailability enhancers which are commonly used in the manufacture of pharmaceutically acceptable solid, liquid, or other dosage forms may also be used for the purposes of formulation.

In embodiments, the agents and/or compositions can be delivered in an exosomal delivery system. Exosomes are small membrane vesicles that are released into the extracellular environment during fusion of multivesicular bodies with plasma membrane. Exosomes are secreted by various cell types including hematopoietic cells, normal epithelial cells and even some tumor cells.

In certain embodiments, the biopolymer encapsulating the D-PDMP comprises polyethelene glycol (PEG) and sebacic acid (SA). Both PEG and SA are FDA approved. The polyethylene glycol-sebacic acid (PEG-SA) copolymer can be prepared as previously described (Fu J, et al. *Biomaterials.* 2002; 23:4425-4433), Microparticles of D-PDMP encapsulated by the PEG-SA copolymer are prepared by modifying the single emulsion solvent evaporation method. For scintigraphic tracking of the biopolymer, the PEG polymer is radio-iodinated with 45 mCi (810 kBq) of [$^{125}$I]NaI. The radiolabeled PEG was then incorporated into the PEG-SA biopolymer. The PEG-SA co-polymer can be prepared following the published literature procedure by Fu and coworkers (Id.). Briefly, sebacic acid prepolymer is made by refluxing sebacic acid (SA) in acetic anhydride followed by drying under high vacuum (evaporation), crystallized from dry toluene, washed with 1:1 anhydrous ethyl ether-petroleum ether and finally air dried. PEG prepolymer is made by refluxing of polyoxyethylene dicarboxylic acid in acetic anhydride, volatile solvents are removed under vacuum. The solid mass is extracted with anhydrous ether and air dried. The poly(PEG-SA) co-block polymer is then synthesized by the melt polycondensation method and characterized by proton NMR. Note that this copolymer has been extensively characterized for the composition and structural identity (Aich U, et al. *Glycoconjugate journal.* 2010; 27:445-459).

Encapsulation of D-PDMP in poly(PEG-SA) (to prepare polymer-encapsulated drug subsequently referred to as BPD) followed by the melt polycondensation method described above for SA and PEG prepolymers but with the inclusion of D-PDMP at starting ratios of poly(PEG-SA) to D-PDMP of 70:30 by weight. Subsequently, microparticles are prepared using a single emulsion solvent evaporation method. Briefly, D-PDMP and PEG-SA are dissolved in chloroform (50 mg/mL) and emulsified into a 1.0% w/w poly(vinyl alcohol) aqueous solution under sonication condition keeping the temperature below 25° C. Particles are hardened by allowing chloroform to evaporate at room temperature while stirring for 12 h. Particles are collected and washed three times with double distilled water via centrifugation at 2,600.times.g (30 min) and lyophilized for 48 h before it was ready to use.

In certain embodiments, the D-PDMP is encapsulated in a multilamellar lipid vesicle comprising covalent crosslinks between lipid bilayers, wherein at least two lipid bilayers in the multilamellar lipid vesicle are covalently crosslinked to each other by a thiolated biopolymer. In certain embodiments, the lipid bilayers are crosslinked via functionalized lipids. In certain embodiments, the one or more lipids comprise DOTAP, DOPE, DOBAQ, DOPC or combinations thereof. In certain embodiments, the lipid is maleimide-functionalized or modified with dibenzocyclooctyne (DBCO). In certain embodiments, the thiolated biopolymer is selected from the group consisting of chitosan, polyglutamic acid, polyphosphazene, polyethyleneimine, polyalky acrylic acids (e.g. polymethylmethacrylate, poly(ethyl-acrylic acid), poly(propylacrylic acid), or poly(butylacrylic acid), HA, pegylated azide-modified polyethylenimine, branched polyethylenimine, and diazide. In certain embodiments, the thiolated biopolymer comprises multiple sulfhydryl moieties.

Also contemplated by the invention is delivery of the pharmaceutical agents and/or therapeutic compounds using nanoparticles. For example, the agents and/or compositions provided herein can contain nanoparticles having at least one or more agents linked thereto, e.g., linked to the surface of the nanoparticle. A composition typically includes many nanoparticles with each nanoparticle having at least one or more agents linked thereto. Nanoparticles can be colloidal metals. A colloidal metal includes any water-insoluble metal particle or metallic compound dispersed in liquid water. Typically, a colloid metal is a suspension of metal particles in aqueous solution. Any metal that can be made in colloidal form can be used, including gold, silver, copper, nickel, aluminum, zinc, calcium, platinum, palladium, and iron. In some cases, gold nanoparticles are used, e.g., prepared from $HAuCl_4$. Nanoparticles can be any shape and can range in size from about 1 nm to about 10 nm in size, e.g., about 2 nm to about 8 nm, about 4 to about 6 nm, or about 5 nm in size. Methods for making colloidal metal nanoparticles, including gold colloidal nanoparticles from $HAuCl_4$, are known to those having ordinary skill in the art. For example, the methods described herein as well as those described elsewhere (e.g., US Pat. Publication Nos. 2001/005581; 2003/0118657; and 2003/0053983, which are hereby incorporated by reference) are useful guidance to make nanoparticles.

In certain cases, a nanoparticle can have two, three, four, five, six, or more active agents linked to its surface. Typically, many molecules of active agents are linked to the surface of the nanoparticle at many locations. Accordingly, when a nanoparticle is described as having, for example, two active agents linked to it, the nanoparticle has two active agents, each having its own unique molecular structure, linked to its surface. In some cases, one molecule of an active agent can be linked to the nanoparticle via a single attachment site or via multiple attachment sites.

An active agent can be linked directly or indirectly to a nanoparticle surface. For example, the active agent can be linked directly to the surface of a nanoparticle or indirectly through an intervening linker.

Any type of molecule can be used as a linker. For example, a linker can be an aliphatic chain including at least two carbon atoms (e.g., 3, 4, 5, 6, 7, 8, 9, 10 or more carbon atoms), and can be substituted with one or more functional groups including ketone, ether, ester, amide, alcohol, amine, urea, thiourea, sulfoxide, sulfone, sulfonamide, and disulfide to functionalities. In cases where the nanoparticle includes gold, a linker can be any thiol-containing molecule. Reaction of a thiol group with the gold results in a covalent sulfide (—S—) bond. Linker design and synthesis are well known in the art.

In embodiments, the nanoparticle is linked to a targeting agent/moiety. A targeting functionality can allow nanoparticles to accumulate at the target at higher concentrations than in other tissues. In general, a targeting molecule can be one member of a binding pair that exhibits affinity and specificity for a second member of a binding pair. For example, an antibody or antibody fragment therapeutic agent can target a nanoparticle to a particular region or molecule of the body (e.g., the region or molecule for which the antibody is specific) while also performing a therapeutic function. In some cases, a receptor or receptor fragment can target a nanoparticle to a particular region of the body, e.g., the location of its binding pair member. Other therapeutic agents such as small molecules can similarly target a nanoparticle to a receptor, protein, or other binding site having affinity for the therapeutic agent.

When the compositions of this invention comprise one or more additional therapeutic or prophylactic agents, the therapeutic agent and the additional agent should be present at dosage levels of between about 0.1 to 100%, or between about 5 to 95% of the dosage normally administered in a monotherapy regimen. The additional agents may be administered separately, as part of a multiple dose regimen, from the agents of this invention. Alternatively, those additional agents may be part of a single dosage form, mixed together with the agents of this invention in a single composition.

The administration of the pharmaceutical agents and/or therapeutic compounds of the invention elicits, for example, an anti-atherosclerosis response. Typically, the dose can be adjusted within this range based on, e.g., the subject's age, the subject's health and physical condition, the capacity of the subject's immune system to produce an immune response, the subject's body weight, the subject's sex, diet, time of administration, the degree of protection desired, and other clinical factors. Those in the art can also readily address parameters such as biological half-life, bioavailability, route of administration, and toxicity when formulating the agents and/or compositions of the invention.

EXAMPLES

Example 1: Inhibition of Glycosphingolipid Synthesis Reverses Skin Inflammation and Hair Loss in ApoE$^{-/-}$ Mice Fed Western Diet A mouse model of atherosclerosis, ApoE$^{-/-}$, was used to determine the effects of consumption of a high fat and high cholesterol diet on skin GSL composition, and skin inflammation, involving inflammatory cells (e.g., neutrophils), and tumor necrosis factor-alpha (TNF-alpha)-stimulated gene-6 (TSG-6). As TSG-6 binds to the extracellular matrix component hyaluronan (37), and is associated with wounding and inflammatory conditions, including neutrophil migration (38), it was hypothesized that inhibition of GSL synthesis could interfere with inflammation of the skin, with subsequent effects on hair coloration and hair loss, in ApoE$^{-/-}$ atherosclerotic mice fed a western diet.

Materials and Methods

Animal Study Approval and Protocol: All experiments were approved and followed the guideline set by the Johns Hopkins School of Medicine Animal Care and Use Committee Male, 11-week-old apolipoprotein E-deficient (ApoE−/−) mice were purchased from Jackson Labs (Bar Harbor, Maine), and fed a western diet from the age of 12 to 20 weeks. Next, they were divided into the following diet/treatment groups. (A) Normal chow; (B) western diet (4.5 kcal/g, 20% fat, and 1.25% cholesterol (D12108C, Research Diet Inc, New Brunswick, NJ; (C) Western diet plus 1 mpk of biopolymer encapsulated D-PDMP (BPD); (D) western diet plus 5 mpk BPD; (E) western diet plus 10 BPD and (F) 10 mpk D-PDMP (Matreya, LLC (State College, PA)). At 20- and 36-weeks of age, mice were photographed, euthanized, and skin tissue surgically removed and store for immune-histopathological and molecular studies.

Measurement of the distribution of neutrophils and TSG-6 in skin tissue: Skin tissue was formalin-fixed, embedded, cut into thin sections (5-μm), and subjected to staining with hematoxylin-eosin, antibodies against a neutrophil marker (CD166), and tumor necrosis factor-alpha-induced protein (TSG-6). After staining, the skin tissue was photographed (20×). Immunochemically stained and scanned digitally, using an Asperio CS Scanscope (Vista, CA). For neutrophil- and TSG-6-positive cells, the rare event and nuclear Aperio (University of Chicago) algorithms Tool Box Kit was used. Detection was further confirmed by hand curation. Values were divided by the total cell counts of the area determined by the nuclear algorithm. TSG-6-positive mask areas were identified by dividing a TSG-6-positive mask area in (A) placebo; (B) by the area in mice treated with 5 mpk of BPD (B) and control mice skin (C).

Quantification of Skin Glycosphingolipids:

Sample preparation: Glycosphingolipid molecular species were extracted according to a modified Bligh and Dyer procedure[55] Briefly, about 50-mg of each tissue sample was homogenized with 10 volumes of HPLC water at room temperature, followed by addition of 30 volumes methanol solution containing ammonium formate and d18:1/$C_{12:0}$ ceramide as an internal standard (Avanti Polar Lipids, Alabaster, Alabama). The mixture was vortexed (Vortex-Genie, Model G560, Scientific Industries, Bohemia, NY), and 40 volumes of chloroform added. The mixture was vortexed again and centrifuged (Eppendorf centrifuge #5424) at 1,000 g for 10 minutes. The chloroform (bottom layer) was separated and dried using a Savant™ SPD131 SpeedVac (Thermo Scientific, Pittsburgh, PA, USA). Dried extracts were resuspended in pure methanol and sealed and stored at −80° C. until analysis by LC-ESI/MS/MS, as described previously[30-40].

Measurement of skin discoloration: An oval shape was drawn on the photographs taken from mice at the age of 36 weeks. This oval space covered the back area of mice from the neck to the tail (~75,000 mm²). Using the free drawing pen and measure/analyze tool, the white area was measured for each mouse. The ratio of white area to the total area was then calculated, and the standard deviations for all the animals in each cage (N=5) was calculated and plotted.

Measurement of wounds and wound healing: For mouse skin wound analysis, the number of visible wounds in placebo-vs. BPD-treated mice (N=5 in each group), were counted manually. Then, averages of the wounds for each group were determined, as were the ratios of wounds in BPD-vs placebo-treated mice. Those ratios were then converted to percentages, expressed as "% wound healing."

Measurement of B1-4GalT-V mass in skin tissue: Here, about 10-mg skin tissue was homogenized in RIPA buffer and centrifuged at 10,000 rpm. The mass of GalT-V was measured in the supernatant fraction using an ELISA assay. About 100-μg of each protein sample (in triplicate) was loaded in 96-well, medium-binding, clear flat bottom polystyrene ELISA plates (Immulux, Chantilly VA)-total volume adjusted to 100 μL with bicarbonate buffer (50 mM $Na_2CO_3$—$NaHCO_3$). A synthetic GalT-V peptide having the sequence (IGAQVYEQVLRSAYAKRNSSVNDc (SEQ ID NO: 1)) served as a reference standard. This antibody has been used in western immunoblot assays, ELISA assays and immunohistochemistry. This antibody specifically recognizes human, mouse and rat tissue B4GalT-V. Moreover, this interaction can be inhibited by large volumes of the GalT-V peptide but not other proteins or scrambled peptide. After overnight incubation at 4 C, 200 μL of blocking buffer (1% bovine serum albumin/phosphate buffered saline) was added and incubation continued overnight. Primary rabbit polyclonal antibody against GalT-V peptide was then added, and the plates incubated for 1-hr at 37 deg. C., followed by incubation for 1-hr at 37 deg. C. with a horseradish peroxidase-conjugated IgG (Sigma) secondary antibody. Finally, 100-μL of TMB solution was added, and after 10 min incubation at 37° C., absorbance was measured at 450 nm.

Analysis of gene expression by quantitative Real-Time PCR: A ~50-mg piece of skin tissue was homogenized from each mice and total RNA was isolated using TRIsol reagent according to the manufacturer's instructions (Invitrogen, Camarillo, CA). Two microgram of RNA were reverse transcribed with SuperScript II using random primers. The primer sequence for GalT-V were as follows:

```
LacCerS
                              (SEQ ID NO: 2)
CATGAACACCTCCCGATCTT, (SEQ ID NO: 3)
TTCATGGCCTCTTTGAAACCCCT, (SEQ ID NO: 4)
GCCAGCTCCTTTTTCTGATG, (SEQ ID NO: 5)
CCTGCAGGCTTCTTCCATAG.

GlcCerS
                              (SEQ ID NO: 6)
AGTGTGTGACGGGGATGTCT, (SEQ ID NO: 7)
CTTCCGCAATGTACTGAGCA.

GAPDH
                              (SEQ ID NO: 8)
GGATCCACCACAGTCCATGCCATCAC, (SEQ ID NO: 9)
AAGCTTTCCACCACCCTGTTGCTGTA.
```

The primers were synthesized by Integrated DNA Technologies (Coralville, USA). Real time PCR were performed using SYBR Green PCR Master Mix PCR Master Mix (applied Biosystems, Foster City, CA, USA) in an Applied Biosystems Step one Real time PCR system as described previously[52]. Data were normalized to GAPDH mRNA levels. Expression suite software (Applied Biosystems) was used to analyze the data.

Results

Figures 1A, 1B, 1C, 1D, 1E, 1F, 1G, 1H, 1I, 1J:
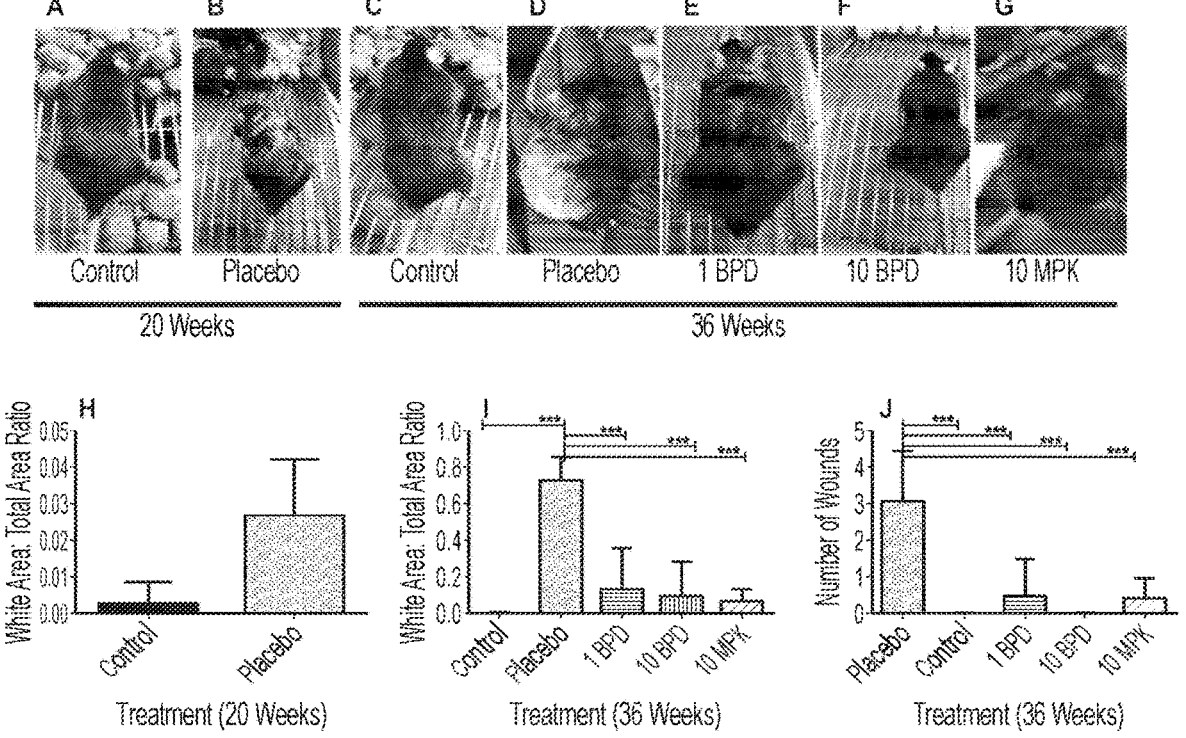
FIGS. 1A-1J show the phenotypes of Apo E$^{-/-}$ mice skin and hair fed with and without western diet.

Feeding a western diet leads to skin dys-homeostasis, preventable by the glycosphingolipid inhibitor BPD: ApoE⁻/⁻ mice were fed normal chow or a western diet, continuously from the age of 12 to 20 weeks. Next, mice were fed 1 mg/kg (mpk) 5, 10 mpk of BPD (encapsulated form of the GSL synthesis inhibitor, PDMP), and 10 mpk (unbound) D-PDMP, daily, by oral gavage, from the age of 20 to 36 weeks (time of atherosclerosis onset), with continuation of the same diet. It was observed that compared to mice fed normal chow (FIG. 1A), ApoE⁻/⁻ mice fed a western diet from 12-20 weeks of age had modestly increased hair whitening, loss of hair, and skin lesion formation (FIGS. 1B and 1H), compared to Apo-mice fed a normal chow diet. When the western diet was continued to 36 weeks of age, a marked loss of hair, extensive whitening of the skin (FIGS. 1D and 1I), was noted as compared to ApoE⁻/⁻ mice fed normal mice chow for 36 weeks (FIG. 1C and FIG. 1I). Moreover, feeding 1 mpk BPD (FIG. 1E) and 10 mpk BPD (FIG. 1F), concurrent with the western diet, from 20 weeks to 36 weeks, ameliorated hair discoloration, hair loss, and skin inflammation (FIGS. 1E, IF and 1G). Analogously, treatment with 10 mpk unbound D-PDMP also interfered with these pathologies (FIGS. 1G and 1I). In addition, ApoE$^{-/-}$ mice fed a western diet for 36 weeks had numerous small and large inflammatory wounds/skin lesions (FIG. 1D and FIG. 1J), compared to ApoE-mice fed normal chow (FIG. 1C). However, treatment with 1 mpk and 10 mpk of BPD markedly promoted wound healing. Treatment during 20-36 weeks of age with 1 mpk BPD was as efficient as 10 mpk of native/un-encapsulated D-PDMP (FIG. 1K) (N=5 p<0.05).

Quantitative analysis of whitening of skin was done by scanning the area from the neck to the back of mice (FIG. 1I). It was observed that placebo mice had ~75% whitening of hair/hair loss, and treatment with BPD or D-PDMP interfered with this phenotype. It was also observed that feeding a high fat and cholesterol caused wounding of the skin (FIG. 1J). Treatment with BPD dose-dependently interfered with wounding of the skin. And treatment with 1 mpk of BPD was as effective (87%) as 10 mpk of D-PDMP (83%) in wound healing.

Figures 2A, 2B, 2C, 2D, 2E, 2F:
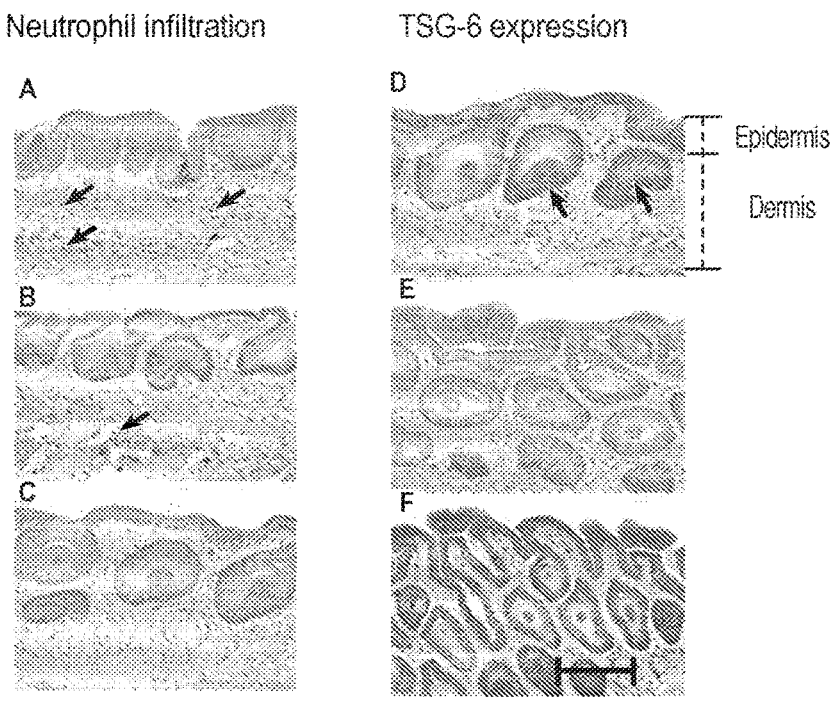
FIGS. 2A-2F show the neutrophil infiltration and TSG-6 expression. Representative thin sections of skin stained with an antibody against neutrophils (CD166), and counterstained with hematoxylin-eosin. Feeding western diet resulted in the infiltration of neutrophils, into various skin dermal areas (FIG. 2A, see arrows) as compared to controls (FIG. 2C). In contrast, BPD treatment significantly reduced the number of infiltrating neutrophils (FIG. 2B). Immunostained skin section (FIG. 2D), with an antibody against the TSG-6 protein, finding that show positive reaction in mice were fed a western diet (FIG. 2D), vs. control mice on normal chow diet (FIG. 2F). In contrast, mouse skin sections did not react positively to this antibody, following treatment with BPD (FIG. 2E). Demonstrating BPD's high efficacy, in reversing skin neutrophil migration, via TSG-6 down-regulation and inhibition of skin lesion formation/inflammation. (Magnification 20×).

Neutrophil infiltration and TSG-6 expression in skin is ameliorated by Treatment with BPD. When representative thin sections of skin were stained with an antibody against neutrophils (CD166), and counterstained with hematoxylin-eosin, it was observed that feeding a western diet resulted in the infiltration of neutrophils, into various skin dermal areas (FIG. 2A, see arrows) as compared to controls (FIG. 2C). In contrast, BPD treatment significantly reduced the number of infiltrating neutrophils (FIG. 2B). Since tumor necrosis factor, a pro-inflammatory cytokine, is known to stimulate several genes, including tumor necrosis factor-stimulated gene-6 (TSG6), skin sections were also immunostained with an antibody against the TSG-6 protein, finding that skin sections reacted positively when mice were fed a western diet (FIG. 2D), vs. control mice (i.e., normal chow) (FIG. 2F). In contrast, mouse skin sections did not react positively to this antibody, following treatment with BPD (FIG. 2E) The neutrophil count in placebo, 5BP treated and control mice were (329, 223 and 246, respectively suggesting that treatment normalized the neutrophil count in the skin. The TSG-6 values for placebo, 5BP and control mice were, 312,189 and 254, showing a significant decrease in TSG-6 expression upon treatment. These values were derived by counting the immunoreactive cells (brown spots) from four different areas of thin skin tissue sections from two separate mice skin specimens. These results demonstrate BPD's high efficacy, in reversing skin neutrophil migration, via TSG-6 down-regulation and inhibition of skin lesion formation/inflammation.

Figures 3A, 3B, 3C:
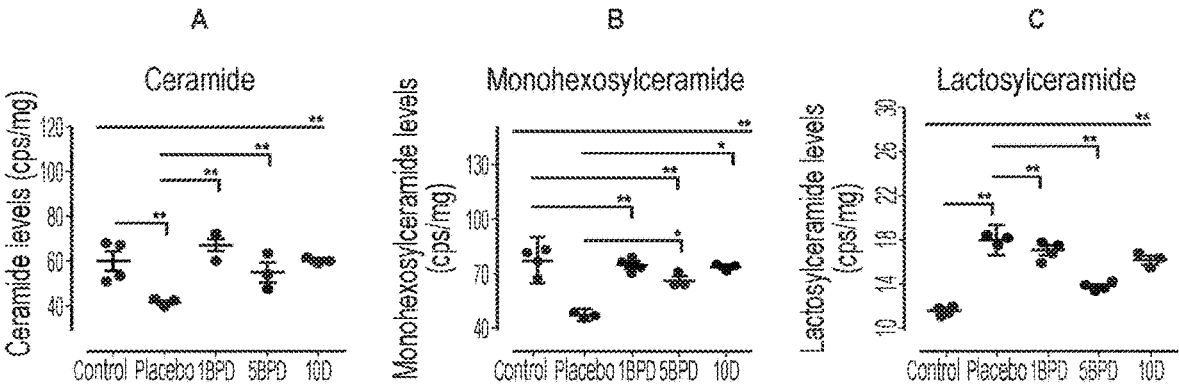
FIGS. 3A-3C show the total ceramide, monohexosylceramide and lactosylceramide levels in skin samples. Skin tissue were subject to total lipid extraction and MS-MS analysis in mice fed chow (blue/control) a western diet (red/placebo), western diet+1 mpk of biopolymer-encapsulated D-PDMP (green/1BPD) daily by oral gavage from age 20 weeks to 36 weeks, western diet+10 mpk-BPD (10BPD/pink) and western diet+10 mpk of D-PDMP (10D/). As compared to normal chow, mice fed western diet alone (red) decreased the total ceramide and monoglycosylceramide mass, whereas the level of lactosylceramide increased. Treatment with the un-encapsulated (D-PDMP) and biopolymer-encapsulated D-PDMP (BPD) increased total ceramide and glucosylceramide levels, in a dose-dependent, to near-normal levels. Both BPD and D-PDMP treatment decreased total lactosylceramide levels in the skin (FIG. 3C). A nonparametric one-way ANOA using the Kruskal-Wallis test and Dunn's multiple comparison post-test was performed.*p<0.05, p<, 001, *p<0.001; n=3-5.

Biopolymer-encapsulated D-PDMP is superior to unbound D-PDMP, in restoring hair homeostasis. MS-MS analysis revealed that mice fed a western diet had relatively low levels of total ceramides (FIG. 3A), compared to mice fed regular chow (FIG. 3A). Similarly, glucosylceramide levels were lower in mice fed a western diet (FIG. 3B). In contrast, lactosylceramide levels were significantly increased in mice fed a western diet, compared to controls (FIG. 3C). Upon feeding BPD, it was observed that total ceramide and glucosylceramide levels increased, in a dose-dependent manner, to near-normal levels. Similarly, treatment with the un-encapsulated inhibitor, D-PDMP, albeit at a significantly higher dose than the biopolymer-encapsulated D-PDMP, also increased ceramide and glucosylceramide levels. Conversely, treatment with either BPD or D-PDMP decreased total lactosylceramide levels in the skin (FIG. 3C).

Figures 6A, 6B, 6C, 6D, 6E, 6F, 6G:
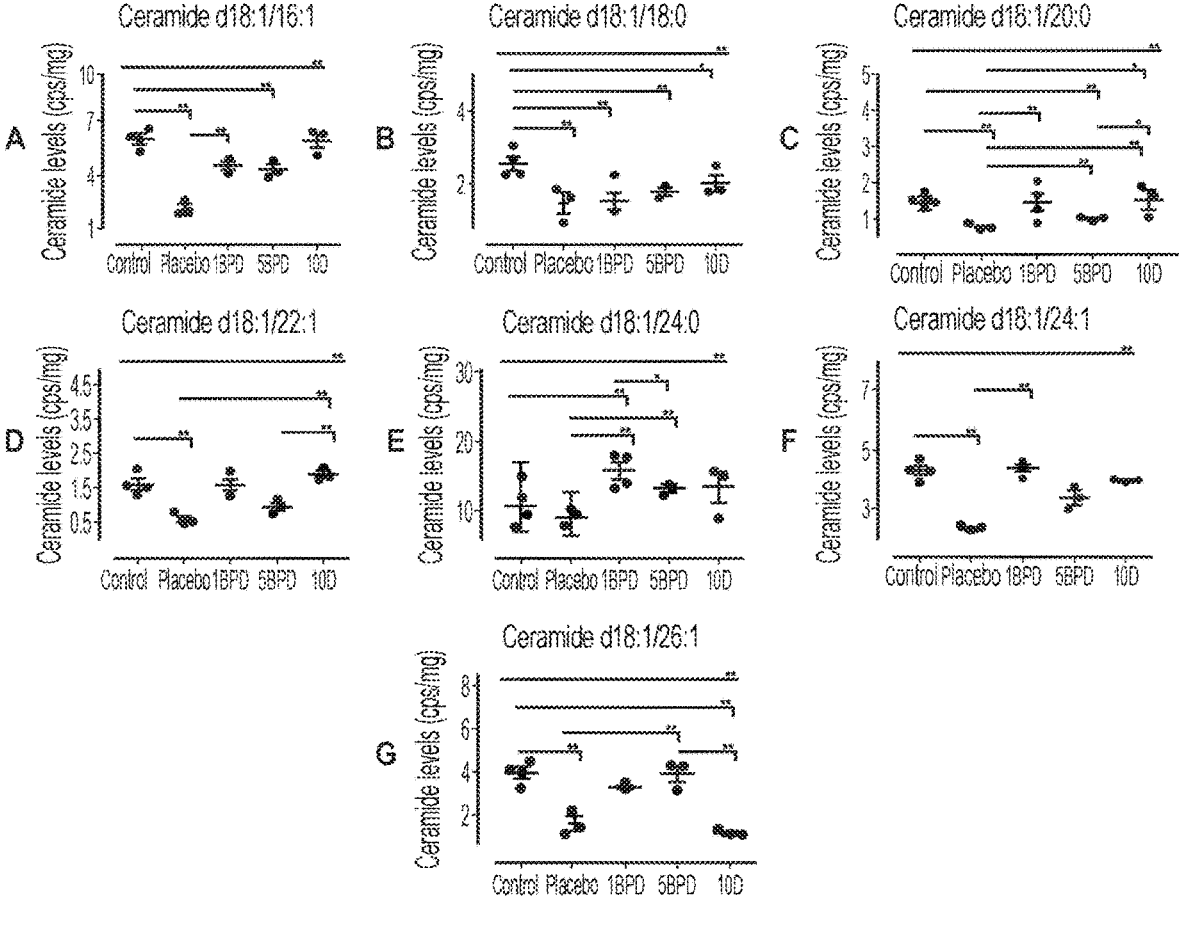
FIGS. 6A-6G show the level of various molecular species of ceramide in skin samples.

Detailed mass spectrometric analysis of control mice skin ceramides showed that d18:/24:0, d18:/26:1, d18:/16:1, d18:1/24:1, d18:1/22:1, d18:1/18:0, and d18:1/20:0 were the predominant fatty acid molecular species (in the hydrophobic "tails" of ceramides), in a descending order (FIGS. 6A-6G). Feeding a western diet decreased, by ~3-fold, the levels of almost all fatty acid molecular species of ceramide, except for C18:1/24:0, which did not change significantly (FIG. 6E). Treatment with 1 mpk BPD, or 10 mpk D-PDMP, however, increased them to normal levels. However, treatment with 10 mpk D-PDMP did not reverse the loss of d18:1/26:1 ceramide, nor did increasing the dose of BPD from 1 to 5 mpk, affect levels of skin ceramides, and thus, the negative consequences of aging, including pigmentation and hair loss.

Figures 7A, 7B, 7C, 7D, 7E, 7F, 7G:
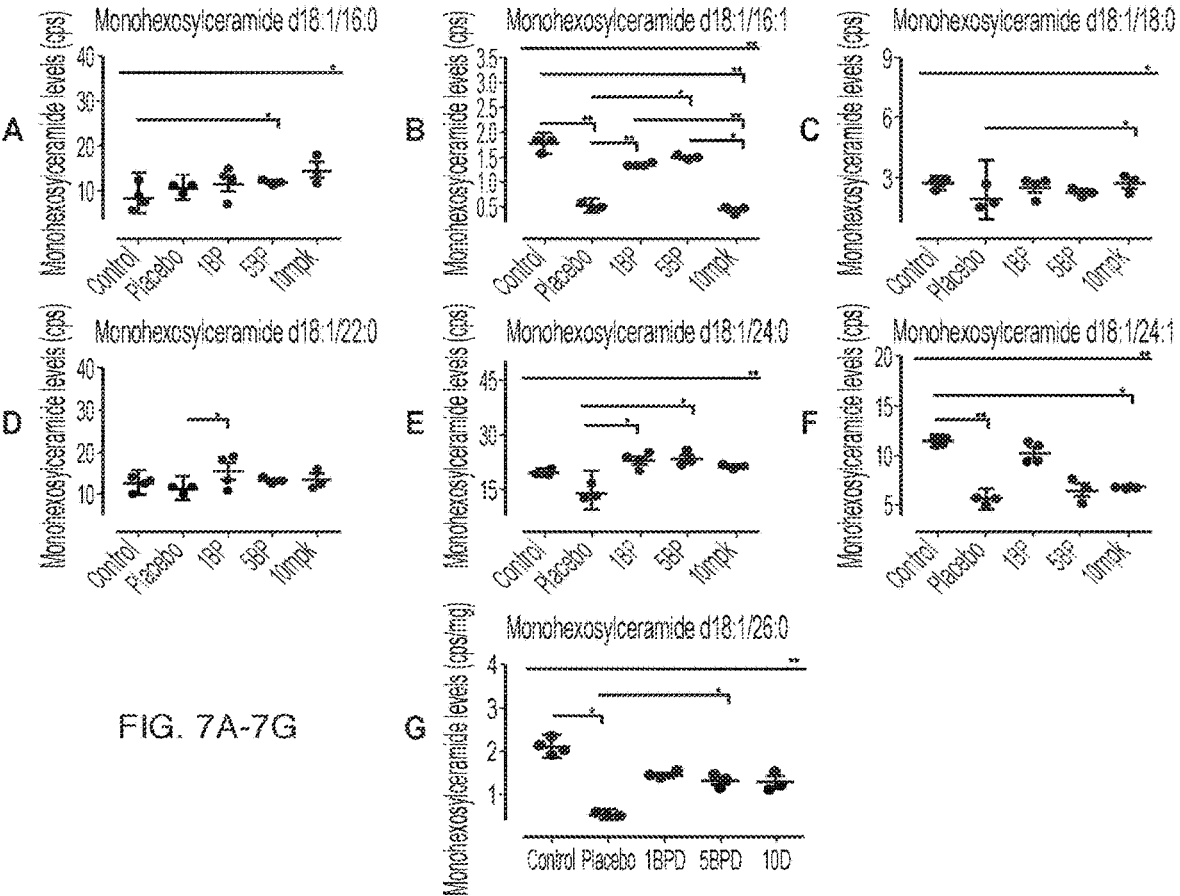
FIGS. 7A-7G show the level of various molecular species of monohexosyl ceramide in skin samples. MS/MS analysis of skin monoheoxosylceramides in Apo E$^{-/-}$ mice fed normal chow, western diet with and without treatment with D-PDMP and BPD. A distinct, difference in the fatty acid molecular composition of skin ceramides, and their glycosylated derivatives was observed with D-PDMP treatment. The level of d18:1/16:0 monohexosylceramide was modestly increased in mice fed the western diet, but remained unchanged with BPD treatment. The level of monohexosylceramide containing d18:1/18:0 and d18:1/22:0 remained unchanged, with or without a western diet, or following treatment. Levels of skin monohexosylceramide, having 18:1/24:0 tails, decreased by ~1.5-fold, upon western diet feeding. This level was reversed, however, upon treatment (FIG. 7E), and 1 mpk D-PDMP was as efficacious as treatment with 10 mpk BPD. This treatment increased the level of d18:1/24:1, and 1 mpk BPD was superior to treatment with 10 mpk D-PDMP. The levels of skin monohexosylceramide containing d18:1/24:1 (FIG. 7F) and d18:1/26:0, decreased by ~ 3-fold, in mice fed a western diet. Treatment with 1 mpk BPD, but not 10 mpk D-PDMP, restored skin monohexosylceramide levels containing d18;1/24; 1 (FIG. 8F) fatty acids, which were similar to monohexosylceramides containing the d18:1/26:0 fatty acid (FIG. 8G).

Following D-PDMP treatment, distinct differences were noted in the fatty acid molecular composition of skin ceramides, and their glycosylated derivatives. For example, whereas fatty acid molecular species d18:1/16:0, d18:1/22:0, and d18:1/26:0 were absent from skin ceramides, these three species were present in skin monohexosylceramide. Moreover, the level of d18:1/16:0 monohexosylceramide was modestly increased in mice fed the western diet (FIGS. 7A-7G), but remained unchanged with BPD treatment. Also the level of monohexosylceramide containing d18:1/18:0 and d18:1/22:0 remained unchanged, with or without a western diet, or following treatment (FIGS. 7A-7G). Levels of skin monohexosylceramide, having 18:1/24:0 tails, decreased by ~1.5-fold, upon western diet feeding. This level was reversed, however, upon treatment (FIG. 7E), and 1 mpk D-PDMP was as efficacious as treatment with 10 mpk BPD. However, such treatment raised the level of d18:1/24:1, and 1 mpk BPD was superior to treatment with 10 mpk D-PDMP. Without treatment, the levels of skin monohexosylceramide containing d18:1/24:1 (FIG. 7F) and d18:1/26:0, decreased by ~ 3-fold, in mice fed a western diet. Treatment with 1 mpk BPD, but not 10 mpk D-PDMP, completely restored skin monohexosylceramide levels containing d18;1/24;1 (FIG. 7F) fatty acids, which were similar to monohexosylceramides containing the d18:1/26:0 fatty acid (FIG. 7G).

Figures 8A, 8B, 8C, 8D:
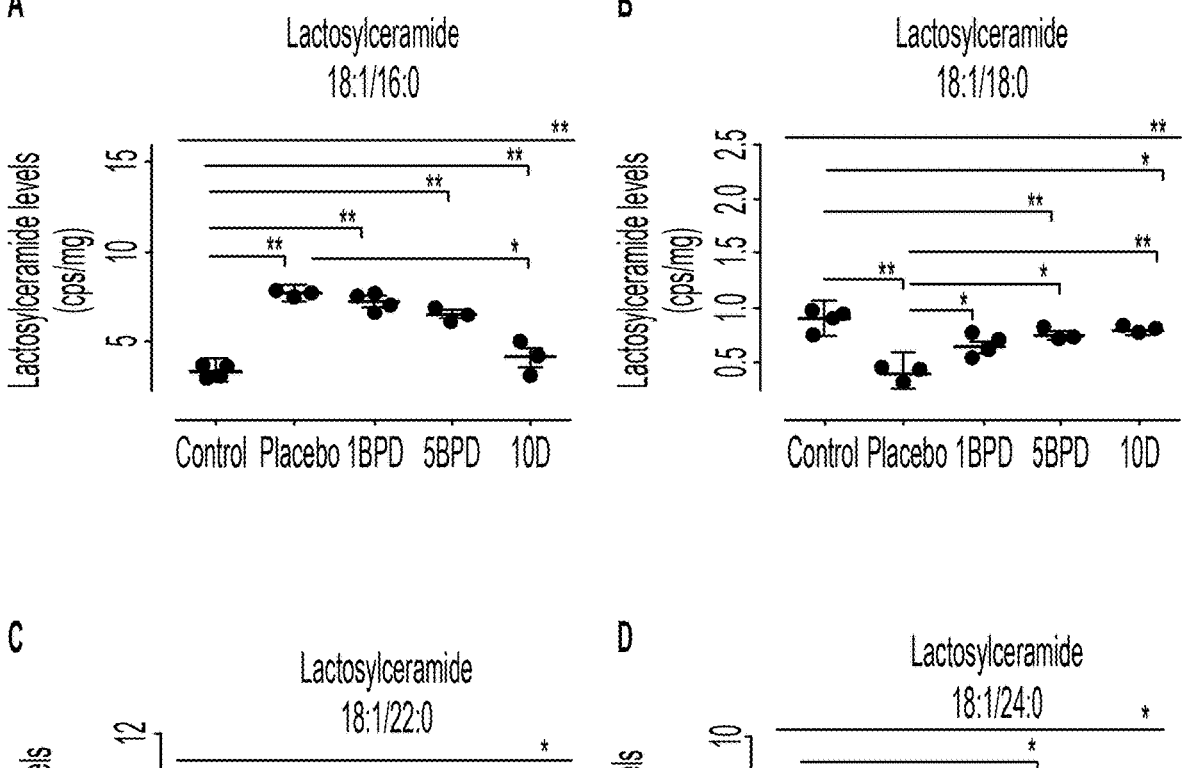
FIGS. 8A-8D show the level of various molecular species of lactosylceramide in skin samples. At 36 weeks, the skin of western diet fed mice, show a 3-fold increase in lactosylceramide having a d18:1/16:0 fatty acid, compared to control mice on a normal diet (FIG. 8A). D-PDMP treatment (FIG. 8A) moderately decreased it. Contrarily, levels of lactosylceramide having d18:1/18:0 decreased ~2-fold in mice fed a western diet, compared to controls, and this was also reversed upon drug treatment (FIG. 8B). Analogously, levels of lactosylceramide having d18:1/22:0 (FIG. 8C) and d18:1/24:1 (FIG. 8D) molecular species were also increased 1.5-fold and 2-fold, respectively, in the skin of mice fed a western diet. These levels were also restored to normal, upon treatment with 1 mpk BPD or 10 mpk D-PDMP (FIGS. 8C, 8D).

The most dramatic observation in the skin of 36 weeks old mice, fed a western diet, was a 3-fold increase in lactosylceramide having a d18:1/16:0 fatty acid, compared to control mice on a normal diet (FIG. 8A). Moreover, this effect was modestly decreased upon BPD or D-PDMP treatment (FIG. 8A). Conversely, levels of lactosylceramide having d18:1/18:0 decreased ~2-fold in mice fed a western diet, compared to controls, and this was also reversed upon drug treatment (FIG. 8B). Analogously, levels of lactosylceramide having d18:1/22:0 (FIG. 8C) and d18:1/24:1 (FIGS. 8B, 8D) molecular species were also increased 1.5-fold and 2-fold, respectively, in the skin of mice fed a western diet. These levels were also restored to normal, upon treatment with 1 mpk BPD or 10 mpk D-PDMP (FIGS. 8C, 8D).

Figure 4:
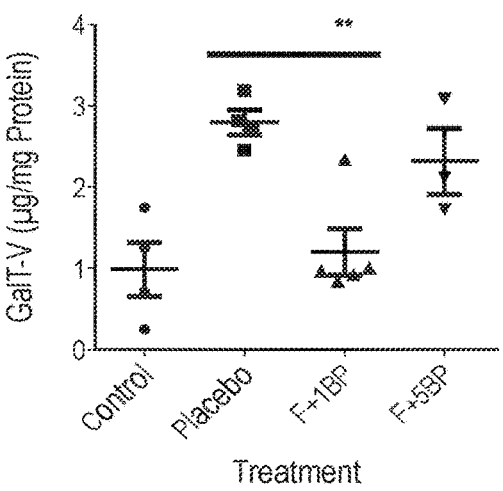
FIG. 4 shows increased lactosylceramide synthase (GalT-V) level in APOE$^{-/-}$ mice is reversed upon treatment with D-PDMP/BPD. Skin tissue from ApoE$^{-/-}$ mice fed normal chow or western diet with and without treatment with D-PDMP and BPD were homogenized in RIPA buffer, centrifuged and the supernatant used as a source of lactosylceramide synthase (GalT-V). The mass of GalT-V was measured using an ELISA assay and antibody raised against this antigen. An increased mass of GalT-V was observed in placebo mice compared to control mice. Conversely, treatment with BPD decreased the mass of GalT-V, with 1BPD being more effective than 5BPD in skin tissue. A nonparametric one-way ANOVA using the Kruskal-Wallis test and Dunn's multiple comparison post-test was performed.*p<0.05, p<, 001, *p<0.001; n=3-5.

Treatment with BPD decreases the mass of B1, 4-Galactosyltransferase (GalT-V). ELISA assays in skin tissue revealed increased mass of GalT-V, upon feeding a western diet to ApoE−/− mice (FIG. 4), as compared to controls. However, treatment with BPD dose-dependently decreased the mass of GalT-V, with 1 mpk of BPD being as effective as 5-mpk D-PDMP, in decreasing GalT-V levels in skin tissue.

Additional q-RT-PCR studies were conducted to determine the mRNA mass of these two glycosyltransferases, namely glucosylceramide synthase (UCGC) and LacCer synthase (GalT-V) in skin tissue. No statistical difference in the mRNA mass (data not shown) between placebo ApoE$^{-/-}$ mice and ApoE$^{-/-}$ mice fed D-PDMP. Thus, D-PDMP treatment did not alter transcriptional regulation of LacCer synthase and GlcCer synthase in skin tissue in this report as well as in liver and brain tissue in these mice and other mouse models of human disease. However, the protein mass of GalT-V determined using an ELISA assay (FIG. 4) showed a decrease upon feeding D-PDMP. It was speculated that this could be due to an increase in the catabolism of GalT-V in D-PDMP fed mice compared to placebo mice.

In ApoE$^{-/-}$ mice fed a high fat and cholesterol diet, treatment with D-PMDP dose-dependently decreased the activity of glucosylceramide synthase and lactosylceramide synthase in liver tissue from the same group of mice which provided us the skin tissue used in the present study (52-53). Since treatment with D-PDMP did not decrease sphingomyelin levels, it is unlikely that increased ceramide levels in mice fed D-PDMP or BPD was due to enhanced catabolism of this phospholipid, via activation of one or more sphingomyelinases (36).

Discussion

In this study, the effects of the glycosphingolipid synthesis inhibitor D-threo-1-phenyl-2-decanoylamino-3-morpholino-1-propanol (D-PDMP), were examined with ("BPD") and without encapsulation in a biodegradable polymer. D-PDMP inhibits the activity of glucosylceramide synthase as well as lactosylceramide synthase (39). Both free and encapsulated D-PDMP affected three adverse consequences of aging on hair biology, hair loss, skin inflammation, and pigment loss. The key observations emerging from this study were: (1) feeding a western diet to ApoE$^{-/-}$ atherosclerotic mice exerts a time-dependent loss in hair color, loss of hair, and skin inflammation/lesion formation, accompanied by neutrophil infiltration and TSG-6 expression; (2) these phenotypic changes were accompanied by significantly decreased skin ceramides and monoglycosylceramides, and increased levels of lactosylceramide; (3) treatment, with either unconjugated/native D-PDMP or biopolymer-encapsulated D-PDMP (BPD), not only prevented loss of hair coloration and skin inflammation, but also reversed these phenotypes to near-normal; and (4) BPD, compared to free D-PDMP, is the superior, more potent, and effective mode of drug delivery. A hypothetical model explaining biochemical/molecular mechanisms, by which lactosylceramide plays a role in skin inflammation, and its restoration by the use of D-PDMP/BPD, is presented in FIG. 5.

Although pioneering studies by Elias et al., have shown an important role for long-chain fatty acid-containing ceramides in maintaining skin hydration, the effects of feeding a western diet, has not been previously investigated (3, 4). The ApoE$^{-/-}$ mouse is a transgenic model of atherosclerosis, having significant defects in the homeostasis of cholesterol and other lipids (40, 41). These mice have thick black hair when fed a normal mouse chow diet. However, upon feeding a high fat and high cholesterol diet, the hair color turns from black to gray to white and finally, is shed-nearly completely lost by 36 weeks of age. It was noted that such progression is identical to that which occurs in normal human aging. This was also accompanied by the appearance of numerous hematosed skin lesions. Our data suggest (FIG. 2A) that inflammation of the skin is accompanied by the enrichment of the tumor necrosis factor-inducible factor, TSG-6, as well as infiltration of neutrophils (FIG. 2B); these events were inhibited by BPD treatment. TSG-6 gene expression is induced by TNF-α and IL-1 (42, 43). Studies show that TSG-6 has a hyaluronan-binding domain, qualifying this protein to be member of the hyaluronan-binding family of proteins associated with matrix stability, cell migration, and inflammation. Thus, increased expression of TSG-6 in the skin of western diet-fed mice may well associate with inflammation and migration of circulatory neutrophils into the skin (FIGS. 2A-2F), being similar to levels expressed in a human male in his late 50s (44, 45).

Figure 5:
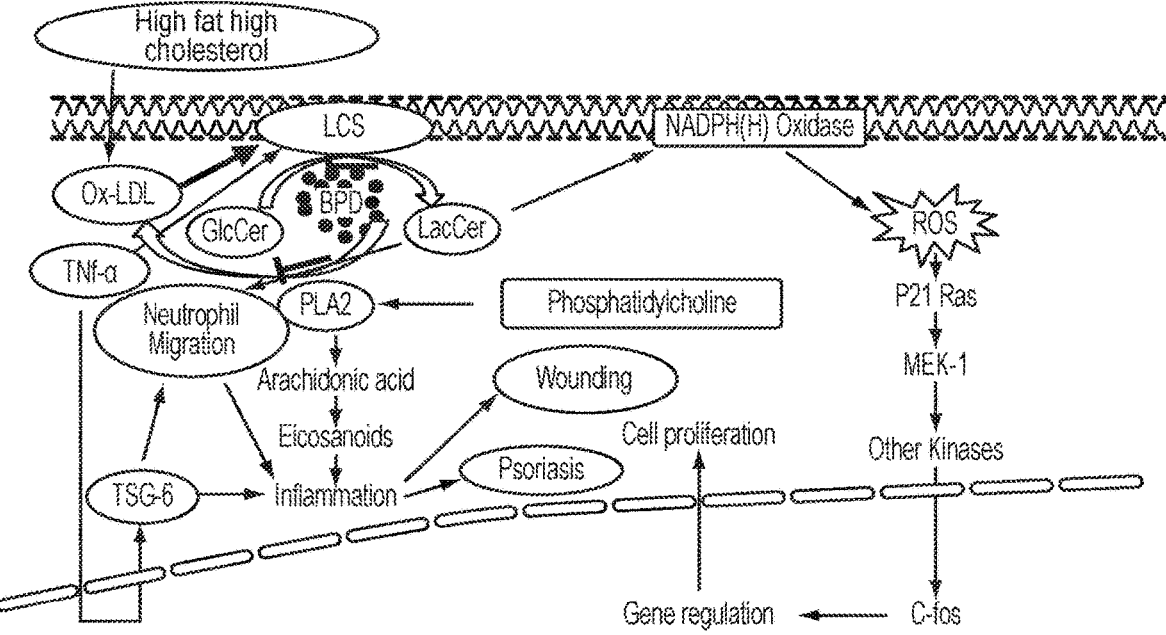
FIG. 5 is a schematic illustration depicting a hypothetical mechanism of how inflammation contributes to psoriasis and the blockage of this pathway with BPD. Feeding a western diet raises the level of oxidized phospholipid which activates lactosylceramide synthase (GalT-V) to generate lactosylceramide which produces reactive oxygen species—a pro-oxidant environment. Lactosylceramide also reacts with infiltrating neutrophils to activate phospholipase A-2, thus releasing arachidonic acid, eicosanoids and contributing to inflammation. Inflammation contributes to wounding and to psoriasis. This cycle of events can be broken by the judicious use of BPD.

Previous studies have shown that neutrophils are highly enriched in lactosylceramide (46) and treatment of these cells with lactosylceramide recruited PKC-alpha/E (47-49) and activated phospholipase A-2, releasing arachidonic acid from phosphatidylcholine (FIG. 5). This release activated a signaling pathway stimulating human neutrophils to upregulate Mac-(CD11b), and generated reactive oxygen metabolites that adhere to the endothelium, via increased expression of the cell adhesion molecule platelet-endothelial cell adhesion molecule (PECAM-1) (26, 47). The role of Src kinase, a member of the large family of tyrosine kinases mediating LacCer-induced superoxide generation of human neutrophils, has been documented as well (27). In vitro studies in human arterial endothelial cells and monocytes showed that LacCer could not only serve as a surrogate to TNF-α and VEGF-meditated ICAM-1, PECAM-1 expression respectively, but also independently stimulates the expression of those cell adhesion proteins. These findings implicate these cell adhesion proteins in trans-endothelial migration of monocytes and neutrophils, considered a "hallmark" of the pathogenesis of inflammation (24, 28). Conversely, treatment with D-PDMP or use of siRNA to ablate β-1,4 galactosyltransferase-V (βGalT-V) gene expression in human arterial endothelial cells blunted the adverse effects of TNF-α and VEGF signaling (28-29). These findings were also corroborated using rat primary astrocytes, wherein LacCer was also implicated in the regulation of TNF-α-induced proliferation (30). In vivo studies, using a rat model of spinal cord injury, which increased TNF-α and IL-1 mRNA expression in the lesion epicenter, associated with white matter vacuolization and loss of myelin and locomotor function suggestive of relevance to neurodegenerative disorders. These processes were obstructed by inhibition of LacCer synthesis via D-PDMP treatment (30). Moreover, increased levels of GlcCer and LacCer have been previously reported in human plaques[31-32] and more recently, plaque inflammation[33]. The latter studies showed that GlcCer and LacCer levels correlated well with several pro-inflammatory cytokines (e.g. interleukin-6, macrophage inflammatory protein (MIP-1B), and monocyte chemoattractant protein-1 (MCP-1) (33). Taken together, these in vitro and in vivo studies may suggest a central role for LacCer, and LacCer synthase, in inflammation, by way of neutrophil infiltration and via TSG-6 expression. Consequently, feeding a western diet to ApoE$^{-/-}$ mice dramatically affects lost hair coloration, hair loss, and skin inflammation, processes reversible by inhibiting LacCer synthesis, further bolster this tenet, offering a novel therapeutic application for LacCer synthase inhibitors, in hair pigmentation and mitigating skin inflammation.

Previous studies of LacCer fatty acid molecular species in human atherosclerotic plaques, as well as calcified plaques, suggest a marked enrichment of d18:1/24:0, d18:1/24:1 LacCer34. When human proximal tubular cells were fed LacCer, derived from human atherosclerotic plaques, a marked increase in cell proliferation was observed, as compared to cells fed LacCer containing d16:0/16:1 or d18:0/d18:1 fatty acid molecular species (34). Subsequent studies revealed that, mole per mole, the longer chain fatty acid "tails" of LacCer generate more reactive oxygen species than shorter chain ones (48, 50-51,27). In the present study, the presence of LacCer was also observed, having d18:1/16:0, 18:1/24:0 and d18:1/24:1 fatty acid molecular species in ApoE-mouse skin. Further, feeding those mice a western diet markedly increased the level of these specific LacCer molecular species. Conversely, feeding a western diet plus D-PDMP/BPD decreased the levels of d18:1/24:0 ceramide and d18:1/26:1 ceramide. A previous study with aortic tissue from ApoE-mice revealed that feeding a western diet increased the activity of GlcCer synthase and LacCer synthase, significantly increasing levels of both GSL endproducts (35). In comparison, in mouse skin, the level of GlcCer did not change significantly upon feeding a western diet or D-PDMP or BPD (FIGS. 3A-3C). Thus, one plausible mechanistic explanation for increased LacCer levels in skin, from western diet-fed mice, could be increased synthesis of LacCer, at the expense of depleting the pool of ceramide. Conversely, treatment with D-PDMP or BPD inhibited LacCer synthase mass accumulation in skin, similar to the effects of these inhibitors in aortic tissue[35], thus restoring ceramide to near-normal levels.

Previously it was found that the encapsulation of D-PDMP within a biopolymer, consisting of polyethylene glycol and sebacic acid, increased gastrointestinal absorption of D-PDMP, and increased its longevity in ApoE[-/-] mice from less than 1 hr, for the unconjugated D-PDMP, to ~48 hours (52, 53). Consequently, 1 mpk of BPD was equally efficacious as 10 mpk of free D-PDMP in decreasing LacCer levels in aortic tissue in ApoE[-/-] mice (37). The preparation of polymer, nano particle formulation and encapsulation of D-PDMP to yield BPD has been described previously (52, 53). Studies on the fate of orally fed BPD has been monitored by planar Gamma scintigraphy as well its pharmaco-kinetics in several tissues in normal mice (C57Bl/6) has been described previously (51, 54). The present study extends this previous observation to the skin tissue. Thus, the important findings from this study were that biopolymer encapsulation is a superior mode of D-PDMP delivery than the unconjugated or native D-PDMP, in mitigating skin inflammation. Although there is ample evidence that D-PDMP can decrease the activity of GlcCer synthase and LacCer synthase it was observed herein, that treatment with BPD or D-PDMP did not markedly decrease the mass of GlcCer (FIG. 3B). This could be explained on the basis that in skin BPD/D-PDMP is relatively more effective inhibitor of LacCer synthase as compared to other tissues. It is also possible that D-PDMP may be converted to its keto amine derivative or other derivatives, which may increase GlcCer synthesis. Alternatively, GlcCer is not catabolized properly in D-PDMP/BPD fed mice. Little is known about the functionality of proteins and enzymes when exposed to biopolymers (BP). At present it can be speculated that feeding 1 mg/Kg body weight of BP-encapsulated D-PDMP provides proteins such as glucosylceramide synthase and LC synthase in a sol-gel trapping environment relatively more stable (compared to 5BP). Thus allowing these enzymes to fold into specific conformations and improved functionality.

In conclusion, this study shows that feeding a western diet to ApoE[-/-] mice could have profound effects on the diet and age-related pathologies of skin inflammation, hair coloration, and hair loss. Moreover, these deleterious events could be inhibited by the judicious use of a biopolymer-encapsulated inhibitor of glycosphingolipid synthesis, BPD that is relatively more efficacious than the native/unconjugated D-PMDP. Since treatment with D-PDMP also lowers the serum levels of cholesterol, oxidized LDL and triglycerides in addition to decreasing the level of GSL, the reversal in skin and hair pathology reported here may well be due to a combined effect on these lipids. It is expected that the observations described herein will bolster further research to elaborate the biology of skin, hair coloration, and hair health, in relevance to diet and inflammation, aging and focused on the role of glycosphingolipids. Taken together, these results demonstrate that biopolymer-encapsulated D-PDMP could be a promising agent for therapeutic use for multiple skin and hair disorders via topical use and/or by oral delivery.

REFERENCES

1. Chatterjee S and Pandey A. The Yin and Yang of lactosylceramide metabolism: implications in cell function. *Biochimica et biophysica acta.* 2008; 1780:370-82.
2. Basu M, De T, Das K K, Kyle J W, Chon H C, Schaeper R J and Basu S. Glycolipids. *Methods in enzymology.* 1987; 138:575-607.
3. Elias P M and Menon G K. Structural and lipid biochemical correlates of the epidermal permeability barrier. *Advances in lipid research.* 1991; 24:1-26.
4. Feingold K R. The regulation and role of epidermal lipid synthesis. *Advances in lipid research.* 1991; 24:57-82.
5. Chatterjee S, Sekerke C S and Kwiterovich P O, Jr. Alterations in cell surface glycosphingolipids and other lipid classes of fibroblasts in familial hypercholesterolemia. *Proc Natl Acad Sci USA.* 1976; 73:4339-43.
6. Schurer N Y and Elias P M. The biochemistry and function of stratum corneum lipids. *Adv Lipid Res.* 1991; 24:27-56.
7. Chatterjee S, Clarke K S and Kwiterovich P O, Jr. Regulation of synthesis of lactosylceramide and long chain bases in normal and familial hypercholesterolemic cultured proximal tubular cells. *The Journal of biological chemistry.* 1986; 261:13474-9.
8. Chatterjee S and Kwiterovich P O, Jr. Glycosphingolipids and plasma lipoproteins: a review. *Can J Biochem Cell Biol.* 1984; 62:385-97.
9. Mommaas-Kienhuis A M, Grayson S, Wijsman M C, Vermeer B J and Elias P M. Low density lipoprotein receptor expression on keratinocytes in normal and psoriatic epidermis. *J Invest Dermatol.* 1987; 89:513-7.
10. Hirobe T, Furuya R, Akiu S, Ifuku O and Fukuda M. Keratinocytes control the proliferation and differentiation of cultured epidermal melanocytes from ultraviolet radiation B-induced pigmented spots in the dorsal skin of hairless mice. *Pigment Cell Res.* 2002; 15:391-9.
11. Hirobe T. Keratinocytes are involved in regulating the developmental changes in the proliferative activity of mouse epidermal melanoblasts in serum-free culture. *Dev Biol.* 1994; 161:59-69.
12. Hirobe T. Structure and function of melanocytes: microscopic morphology and cell biology of mouse melanocytes in the epidermis and hair follicle. *Histol Histopathol.* 1995; 10:223-37.
13. Ito S and Ifpcs. The IFPCS presidential lecture: a chemist's view of melanogenesis. *Pigment Cell Res.* 2003; 16:230-6.

14. Hearing V J. The melanosome: the perfect model for cellular responses to the environment. *Pigment Cell Res.* 2000; 13 Suppl 8:23-34.

15. Adams S C, Garner J P, Felt S A, Geronimo J T and Chu D K. A "Pedi" Cures All: Toenail Trimming and the Treatment of Ulcerative Dermatitis in Mice. *PLOS One.* 2016; 11:e0144871.

16. Kastenmayer R J, Fain M A and Perdue K A. A retrospective study of idiopathic ulcerative dermatitis in mice with a C57BL/6 background. *Journal of the American Association for Laboratory Animal Science: JAALAS.* 2006; 45:8-12.

17. Marx J O, Brice A K, Boston R C and Smith A L. Incidence rates of spontaneous disease in laboratory mice used at a large biomedical research institution. *Journal of the American Association for Laboratory Animal Science: JAALAS.* 2013; 52:782-91.

18. Hampton A L, Hish G A, Aslam M N, Rothman E D, Bergin I L, Patterson K A, Naik M, Paruchuri T, Varani J and Rush H G. Progression of ulcerative dermatitis lesions in C57BL/6Crl mice and the development of a scoring system for dermatitis lesions. *Journal of the American Association for Laboratory Animal Science: JAALAS.* 2012; 51:586-93.

19. Andrews A G, Dysko R C, Spilman S C, Kunkel R G, Brammer D W and Johnson K J. Immune complex vasculitis with secondary ulcerative dermatitis in aged C57BL/6NNia mice. *Vet Pathol.* 1994; 31:293-300.

20. Turturro A, Duffy P, Hass B, Kodell R and Hart R. Survival characteristics and age-adjusted disease incidences in C57BL/6 mice fed a commonly used cereal-based diet modulated by dietary restriction. *J Gerontol A Biol Sci Med Sci.* 2002; 57: B379-89.

21. Blackwell B N, Bucci T J, Hart R W and Turturro A. Longevity, body weight, and neoplasia in ad libitum-fed and diet-restricted C57BL6 mice fed NIH-31 open formula diet. *Toxicol Pathol.* 1995; 23:570-82.

22. Dufour B D, Adeola O, Cheng H W, Donkin S S, Klein J D, Pajor E A and Garner J P. Nutritional up-regulation of serotonin paradoxically induces compulsive behavior. *Nutr Neurosci.* 2010; 13:256-64.

23. Kwan K Y and Wang J C. Mice lacking DNA topoisomerase IIIbeta develop to maturity but show a reduced mean lifespan. *Proc Natl Acad Sci USA.* 2001; 98:5717-21.

24. MacDonald M L, van Eck M, Hildebrand R B, Wong B W, Bissada N, Ruddle P, Kontush A, Hussein H, Pouladi M A, Chapman M J, Fievet C, van Berkel T J, Staels B, McManus B M and Hayden M R. Despite antiatherogenic metabolic characteristics, SCD1-deficient mice have increased inflammation and atherosclerosis. *Arterioscler Thromb Vasc Biol.* 2009; 29:341-7.

25. Ezell P C, Papa L and Lawson G W. Palatability and treatment efficacy of various ibuprofen formulations in C57BL/6 mice with ulcerative dermatitis. *Journal of the American Association for Laboratory Animal Science: JAALAS.* 2012; 51:609-15.

26. Greenwald I. LIN-12/Notch signaling: lessons from worms and flies. *Genes Dev.* 1998; 12:1751-62.

27. Radtke F, Schweisguth F and Pear W. The Notch 'gospel'. *EMBO Rep.* 2005; 6:1120-5.

28. Bray S J. Notch signalling: a simple pathway becomes complex. *Nat Rev Mol Cell Biol.* 2006; 7:678-89.

29. Artavanis-Tsakonas S, Rand M D and Lake R J. Notch signaling: cell fate control and signal integration in development. *Science (New York, NY).* 1999; 284:770-6.

30. Wilson A and Radtke F. Multiple functions of Notch signaling in self-renewing organs and cancer. *FEBS Lett.* 2006; 580:2860-8.

31. Hansson E M, Lendahl U and Chapman G. Notch signaling in development and disease. *Semin Cancer Biol.* 2004; 14:320-8.

32. Krebs L T, Xue Y, Norton C R, Shutter J R, Maguire M, Sundberg J P, Gallahan D, Closson V, Kitajewski J, Callahan R, Smith G H, Stark K L and Gridley T. Notch signaling is essential for vascular morphogenesis in mice. *Genes Dev.* 2000; 14:1343-52.

33. Schouwey K, Delmas V, Larue L, Zimber-Strobl U, Strobl L J, Radtke F and Beermann F. Notch1 and Notch2 receptors influence progressive hair graying in a dose-dependent manner. *Dev Dyn.* 2007; 236:282-9.

34. Pan Y, Lin M H, Tian X, Cheng H T, Gridley T, Shen J and Kopan R. gamma-secretase functions through Notch signaling to maintain skin appendages but is not required for their patterning or initial morphogenesis. *Dev Cell.* 2004; 7:731-43.

35. Schouwey K and Beermann F. The Notch pathway: hair graying and pigment cell homeostasis. *Histol Histopathol.* 2008; 23:609-19.

36. Liao C P, Booker R C, Morrison S J and Le L Q. Identification of hair shaft progenitors that create a niche for hair pigmentation. *Genes Dev.* 2017; 31:744-756.

37. Balazs E A. Interaction between Cells, Hyaluronic-Acid and Collagen. *Upsala J Med Sci.* 1977; 82:94-94.

38. Dyer D P, Thomson J M, Hermant A, Jowitt T A, Handel T M, Proudfoot A E, Day A J and Milner C M. TSG-6 inhibits neutrophil migration via direct interaction with the chemokine CXCL8. *J Immunol.* 2014; 192:2177-85.

39. Chatterjee S, Cleveland T, Shi W Y, Inokuchi J and Radin N S. Studies of the action of ceramide-like substances (D- and L-PDMP) on sphingolipid glycosyltransferases and purified lactosylceramide synthase. *Glycoconjugate journal.* 1996; 13:481-6.

40. Xie X, Zhang L, Lin Y, Wang Y, Liu W, Li X and Li P. Imiquimod induced ApoE-deficient mice might be a composite animal model for the study of psoriasis and dyslipideamia comorbidity. *J Dermatol Sci.* 2017; 88:20-28.

41. Bagchi S, He Y, Zhang H, Cao L, Van Rhijn I, Moody D B, Gudjonsson J E and Wang C R. CD1b-autoreactive T cells contribute to hyperlipidemia-induced skin inflammation in mice. *J Clin Invest.* 2017; 127:2339-2352.

42. Lee T H, Wisniewski H G and Vilcek J. A novel secretory tumor necrosis factor-inducible protein (TSG-6) is a member of the family of hyaluronate binding proteins, closely related to the adhesion receptor CD44. *J Cell Biol.* 1992; 116:545-57.

43. Lee T H, Klampfer L, Shows T B and Vilcek J. Transcriptional regulation of TSG6, a tumor necrosis factor- and interleukin-1-inducible primary response gene coding for a secreted hyaluronan-binding protein. *The Journal of biological chemistry.* 1993; 268:6154-60.

44. Porter R M. Mouse models for human hair loss disorders. *Journal of anatomy.* 2003; 202:125-31.

45. Porter R, Jahoda C, Lunny D, Henderson G, Ross J, McLean W, Whittock N, Wilson N, Reichelt J, Magin T and Lane E. 26 Mouse models for human hair loss disorders. *Journal of anatomy.* 2002; 201:424.

46. Macher B A and Klock J C. Isolation and chemical characterization of neutral glycosphingolipids of human neutrophils. *J Biol Chem.* 1980; 255:2092-6.

47. Arai T, Bhunia A K, Chatterjee S and Bulkley G B. Lactosylceramide stimulates human neutrophils to upregulate Mac-1, adhere to endothelium, and generate reactive oxygen metabolites in vitro. *Circ Res.* 1998; 82:540-7.

48. Gong N, Wei H, Chowdhury S H and Chatterjee S. Lactosylceramide recruits PKCalpha/epsilon and phospholipase A2 to stimulate PECAM-1 expression in human monocytes and adhesion to endothelial cells. *Proceedings of the National Academy of Sciences of the United States of America.* 2004; 101:6490-5.

49. Nakamura H, Moriyama Y, Makiyama T, Emori S, Yamashita H, Yamazaki R and Murayama T. Lactosylceramide interacts with and activates cytosolic phospholipase A2alpha. *J Biol Chem.* 2013; 288:23264-72.

50. Iwabuchi K and Nagaoka I. Lactosylceramide-enriched glycosphingolipid signaling domain mediates superoxide generation from human neutrophils. *Blood.* 2002; 100:1454-64.

52. Chatterjee S, Bedja D, Mishra S, Amuzie C, Avolio A, Kass D A, Berkowitz D and Renehan M. Inhibition of glycosphingolipid synthesis ameliorates atherosclerosis and arterial stiffness in apolipoprotein E–/– mice and rabbits fed a high-fat and -cholesterol diet. *Circulation.* 2014; 129:2403-13.

53. Mishra S, Bedja D, Amuzie C, Foss C A, Pomper M G, Bhattacharya R, Yarema K J and Chatterjee S. Improved intervention of atherosclerosis and cardiac hypertrophy through biodegradable polymer-encapsulated delivery of glycosphingolipid inhibitor. *Biomaterials.* 2015; 64:125-35.

54. Fu Y and Kao W J. Drug release kinetics and transport mechanisms of non-degradable and degradable polymeric delivery systems. *Expert Opin Drug Deliv.* 2010; 7:429-44.

55. Bligh E G and Dyer W J. A rapid method of total lipid extraction and purification. *Can J Biochem Physiol.* 1959; 37:911-7.

Example 2: Intervention of Psoriasis, Wound Healing, and Hair Growth is Enhanced by Blocking Glycosphingolipid Synthesis in ApoE$^{-/-}$ Mice and LOX$^{-/-}$ Mice Oxidized low-density lipoproteins (Ox-LDL) is derived from low-density lipoproteins (LDL), the major carrier of cholesterol in the blood. Epidemiological studies reveal that an increased level of circulating Ox-LDL was significantly associated with the risk of atherosclerosis and cardiovascular events (Gao S. et al., *Chronic Dis Transl Med.* 25; 3(2): 89-94, 2017. doi:10.1016/j.cdtm.2017.02.008). Ox-LDL is taken up by cells via several "scavenger receptors"—major ones are scavenger receptor type A (SRA-1), CD-36, and lectin-like oxidized LDL receptor-1 (LOX-1). Studies show that inhibition of the SRA-1 and CD-36 receptors affects the progression of atherosclerosis by decreasing foam cell formation. Similarly, the LOX-1 receptor is engaged in affecting the progression of atherosclerosis at multiple stages (Chen, M., et al. (2002) *Pharmacology & Therapeutics,* 95 (1), 89-100. doi:10.1016/s0163-7258 (02) 00236-x; Mehta, J., et al. (2006). *Cardiovascular Research,* 69 (1), 36-45. doi:10.1016/j.cardiores.2005.09.006; Mehta, J. et al. (2007). *Circulation Research,* 100 (11), 1634-1642. doi:10.1161/ circresaha.107.149724-5). Exogenous Ox-LDL is produced via the interaction of LDL with endothelial cells and hemoglobin under hypoxic conditions in vivo (Quinn M T, et al. *Proc. Natl. Acad. Sci USA.* 1985, 82:5949-5953; Berliner J. et al. 1997. Thromb and Hemostatis 78, 195-199; Balagopalakrishna C, Bhunia A K, Rifkind J M, Chatterjee S. *Mol Cell Biochem* 170, 85-9 (1997)6-8), and is taken up by cells via these receptors. Ox-LDL can also be produced endogenously, due to vitamin E depletion (a pro-oxidant status), and LDL trapped in the vascular matrix (Steinberg D. J. 1977. [Minireview], *J Biol Chem* 272, 20963-20974). Ox-LDL can be found in various tissues and human atherosclerotic plaques in coronary artery disease (CAD) patients as well as in animal models of atherosclerosis (Chatterjee, S. Pathophysiology and vascular Biology of atherosclerosis 2010 in The Johns Hopkins textbook of dyslipidemia (Kwiterovich, P O Jr. Ed), Walters Kuver, Baltimore. Pp 48-57). In contrast, LDL is taken up by LDL receptors located within "coated pits" on the cell surface (Brown M S, Goldstein J L. 1983 Lipoprotein metabolism in the macrophage; implications for cholesterol deposition in atherosclerosis. *Annu. Rev. Biochem* 52:223-261). The lack of LDL receptors or the destruction of LDL receptors by an enzyme-pro-protein convertase subtilsin/kexin type-9 (PCSK-9) can contribute to CAD. PCSK-9 is a member of the pro-protein convertase family of proteins that activate other proteins.

Without wishing to be bound by theory it is hypothesized that there may be a correlation between dyslipidemia and skin inflammatory diseases like psoriasis. This therefore provides a novel target for therapeutic intervention. Dyslipidemia may include high levels of blood LDL cholesterol and triglycerides, and low levels of HDL cholesterol (Raychaudhuri S K, Chatterjee S et al., *Metab. Syndr. Related. Disorder* 2010, 8:331-334)—a typical manifestation of "metabolic syndrome" contributing to obesity, atherosclerosis, stroke, and myocardial infarction.

Psoriasis, wound healing, and hair growth are closely associated with skin health. Herein, the lipid composition of skin may play an important role as well. The inventor has recently shown that in a mouse model of atherosclerosis, ApoE$^{-/-}$ mice fed a high fat and cholesterol (HFHC) or western diet, the skin ceramide level is decreased and the lactosylceramide (LC) level is increased (Bedja, D et al., *Nature-Sci. Reports* (2018) 8:11463-11473) accompanied with hair loss, discoloration and skin inflammation/wounding. Conversely, treatment with a GSL synthesis inhibitor, biopolymer-encapsulated D-Threo-1-phenyl-2-decanoylamino-3-morpholino-1-propanol (BPD), reversed the skin ceramide level to normal levels, reversed hair loss, and alleviated skin inflammation.

In the present study, two models were used: a mouse model of psoriasis, induced by the topical application of imiquimod (IMQ) on the skin of ApoE$^{-/-}$ mice fed a western diet and LOX-1$^{-/-}$ mice fed normal chow to examine the role of dyslipidemia and inhibition of glycosphingolipid synthesis on psoriasis-like pathology. The effects of inhibiting GSL synthesis on wound healing and hair growth was also examined in normal (C57BL-6) mice.

It was observed that topical application of IMQ induced typical symptoms in psoriasis in these mice e.g. scaling of the skin, loss of hair, and erythema formation. A HFHC diet accelerated such phenotypes in ApoE$^{-/-}$ mice. This was accompanied with an increase in the expression of multiple "scavenger receptors" for oxidized low-density lipoproteins (Ox-LDL) such as LOX-1, SRA-1, and CD36. Resulting in an increase in the level of skin and serum Ox-LDL and β-1, 4-galactosyltransferase (GalT-V); the latter an enzyme responsible for the synthesis of LC and consequently LC mass. In turn, the level of ceramide was decreased.

In LOX-1$^{-/-}$ mice, inhibition of GSL synthesis by using BPD decreased psoriasis-like symptoms. Furthermore, it led to a decrease in levels of Ox-LDL, GalT-V, and LC, but an increase in the skin level of ceramide in these mutant mice. In normal (C57BL-6) mice, wounding raised the skin level of wounding biomarkers, TNF-$\alpha$, and MMP-9. As well as GalT-V level. Treatment with BPD accelerated wound healing in a time and concentration-dependent fashion and decreased the level of these biomarkers of wounding. Treatment with BPD also increased hair growth in a time- and dose-dependent manner.

In sum, Ox-LDL may be one of the culprits that induce psoriasis-like symptoms/pathology. Further, the entry of ox-LDL into the skin is facilitated due to increased expression of multiple "scavenger receptors". However, psoriasis-like symptoms can be induced in the absence of LOX-1 receptor. Ox-LDL and TNF-$\alpha$ activate and increase the mass of GalT-V, which produces LC and thus depletes the level of ceramides. In turn, LC contributes to inflammation and consequently psoriasis-like symptoms. Upon blocking GSL synthesis, these phenotypes are reversed and improved wound healing occurs. Thus, blocking GSL synthesis is a new paradigm not only to help with wound healing and hair growth but also useful in reversing psoriasis-like symptoms and probably other skin inflammatory diseases.

Materials and Methods

Animals and Treatment: All experiments were approved and followed the guidelines set by the Johns Hopkins School of Medicine Animal Care and Use Committee. Animals were purchased from the Jackson laboratory (Bar harbor, Maine) or were obtained as a gift from Dr. Dan Berkowitz (Department of Anesthesiology at Johns Hopkins University School of Medicine). Normal (C57BL-6) mice and LOX$^{-/-}$ mice were fed normal chow. ApoE-mice were fed a high fat (21% milk fat) and high cholesterol (1.25%) diet TD96121 (Teklad Custom Diet, New Brunswick, NJ) for 10 weeks prior to use in experiments. The ear lobes of the mice were harvested and used in the confirmation of the genotype of each mice used in our study.

The dorsal or back area of LOX$^{-/-}$ and ApoE$^{-/-}$ mice were shaven by topical application of a hair-removing lotion Nair (Church & Dwight Co, Ewing, NJ). After 10 minutes, an alcoholic swab was used to remove the hair. Next, imiquimod was applied topically to the shaven area daily for 5 days. Next, the mice were divided into the following groups: (1) Placebo (biopolymer suspended in vehicle 5% Tween-80 in PBS) and (2) 5 mpk BPD (5 mg/kg body weight of biopolymer-encapsulated D-PDMP). 100 µL of these solutions were fed daily by oral gavage for up to 5 days. On the other hand, wounds were made on the dorsal area of normal (C57BL-6) mice by using a razor blade. The mice were divided into 3 groups: (1) Placebo (biopolymer suspended in vehicle 5% Tween-80 in PBS), (2) 1 mpk BPD (1 mg/kg body weight of biopolymer-encapsulated D-PDMP), and (3) 5 mpk BPD (5 mg/kg body weight of biopolymer-encapsulated D-PDMP). Treatment with BPD lasted up to 15 days.

All mice were photographed at various time intervals and terminated. Blood was drawn, centrifuged at 3000 rpm and the supernatant was stored at –80° C. The skin area was dissected and stored at –80° C. for further use in various assays. All chemicals were from Sigma (Sigma Chemical Co. St Louis, MO) unless otherwise specified. Antibodies against MMP-9, 1, 2, TNF-$\alpha$, SRA-1, CD-36, and LOX-1 were purchased from Santa Cruz Biotechnology Dallas, TX.

Measurement of hair growth, scaling of the skin, and erythema. The total shaven area covered by the back of the mice was measured and given a value of 1.0. Using a free drawing pen and measure/analyze tool, the black area, representing hair, was measured for each mouse. The ratio of white area to the black area was then calculated, and the standard deviation for all the animals in each group was calculated and plotted. Likewise, to measure scaling of the skin and erythema, a free drawing pen and measure/analyze tool was used to measure the scaling or erythema area on day 4 of day 5 of imiquimod; this was given a value of 1.0. The ratio of the scaling or erythema area on day 5 of placebo or BPD treatment to the initial scaling or erythema area was then calculated and plotted.

Measurement of wounds and wound healing. The total area of the wounds in placebo-treated mice and BPD-treated mice was measured and given a value of 1.0. Using a free drawing pen and measure/analyze tool, the area of the wound was measured for each mouse. The ratio of the remaining wound area on day 9 to the original wound area made on day 1 was then calculated.

Measurement of oxidized LDL, cholesterol, and triglycerides. Mice serum level of Ox-LDL was measured using an ELISA assay and a monoclonal antibody against human Ox-LDL as per the supplier's instructions (Avanti Polar Lipids, Alabaster, AL). Serum levels of triglycerides, cholesterol, and HDL cholesterol were obtained from microtiter readings following Wako kit assays (Wako Diagnostics, Richmond, VA) (Chatterjee S et al. Inhibition of glycosphingolipid synthesis ameliorates atherosclerosis and arterial stiffness in apolipoprotein E–/– mice and rabbits fed a high fat and cholesterol diet. *Circulation* 129:2403-2413 (2014)).

Measurement of Glycosphingolipids. Serum and skin tissue were extracted in acetonitrile-methanol (9:1). The lipid extracts were separated by HPTLC using chloroform-methanol-water (100:42:6 v/v) as solvent. The chromatographic-plate was calibrated with standard solutions of ceramide, glucosylceramide and lactosylceramide. Following separation, the plate was exposed to iodine vapors and photographed. Glycosphingolipids were quantified by densitometric scanning of the bands and a Gel-quant computer program (Chatterjee S. B. et al., Accumulation of glycosphingolipids in human atherosclerotic plaque and unaffected aorta tissues. Glycobiology. 1997 February; 7 (1): 57-65).

Measurement of $\beta$-1,4GalT-V mass in serum and skin tissue. Serum and skin tissue level of $\beta$-1,4 GalT-V mass was measured using an ELISA assay as described in detail (Bedja, D., Yan, W., Lad, V., Iocco, D., Sivakumar, N., Bandaru, V. V., & Chatterjee, S. (2018). Inhibition of glycosphingolipid synthesis reverses skin inflammation and hair loss in ApoE$^{-/-}$ mice fed western diet. *Scientific Reports*, 8(1). doi:10.1038/s41598-018-28663-9). Briefly, a GalT-V peptide was used as a standard and mouse monoclonal antibody against it was used to capture the antigen. Horse-radish peroxidase-conjugated IgG served as the second antibody. A color reaction was developed using TMB and absorbance was measured at 450 nm in a spectrophotometer.

Western blot analysis. About 50 mg of skin tissue from each animal was homogenized in RIPA buffer containing protease inhibitor cocktail (Roche) and centrifuged. Following measurement of protein mass using the Bradford protein assay reagent (VWR; Solon, OH), an equal amount of supernatant proteins was resolved by SDS-PAGE. The gel was calibrated with standard proteins of known molecular weight (Biorad, Richmond, CA). Respective protein bands were detected by immunoblotting. Immunoreactive bands of known molecular weight were visualized using an ECL plus kit (GE Health Care Life Sciences) and quantified with the KODAK Molecular Imaging Software (Kodak, New Haven, CT). β-actin was used as a loading control. The data represents the mean±SD of 3 to 5 independent mice tissues in each group.

Statistical Analysis. All values are presented as dot plots or bar graphs alongside mean+/−SEM. Comparison between groups was performed with one-tailed or two-tailed unpaired t-test or an ordinary one-way ANOVA along with Dunnett's multiple comparisons test. *p<0.05, **p<0.005. Graph Pad PRISM and Excel statistical software were used.

Results

Figures 9A, 9B, 9C, 9D, 9E:
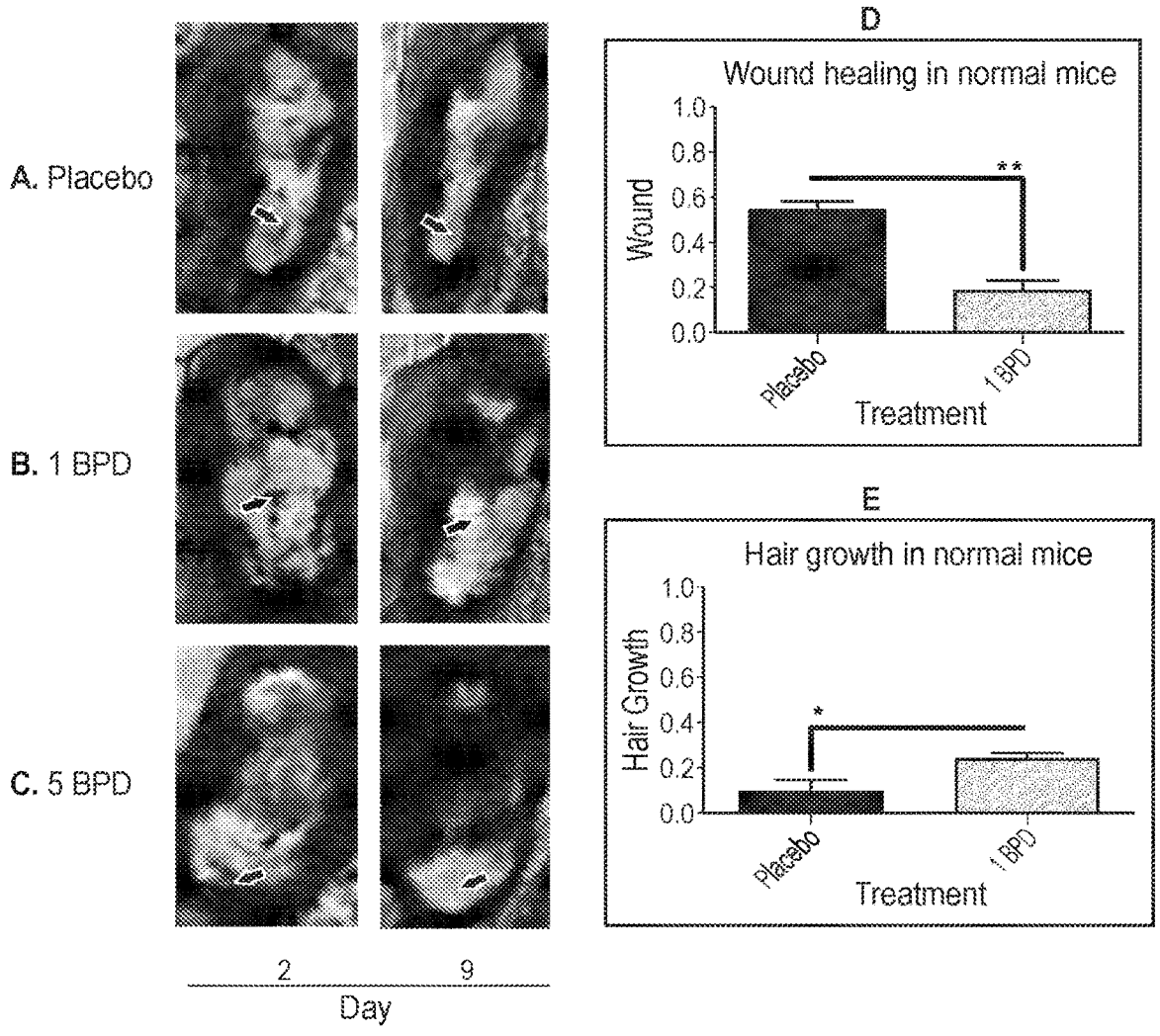
FIGS. 9A-9E are a series of photographs and graphs demonstrating that treatment with BPD improved wound healing and hair growth in normal mice. Normal (C57B1-6) mice fed regular mice chow were shaved with NAIR™ and multiple wounds were made on the shaven skin area on Day 1. From Day 2 to Day 15, the mice were fed daily by oral gavage either vehicle (biopolymer) (placebo group) (FIG. 9A) or 1 mg/kg body weight (mpk) of biopolymer-encapsulated D-PDMP (BPD).

Treatment with BPD accelerates wound healing and hair growth in normal (C57B16) mice. It was observed that compared to mice fed placebo (biopolymer suspended in vehicle: 5% Tween-80 in PBS) (FIG. 9A), mice fed a daily oral gavage of BPD displayed increased wound healing significantly in a time- and dose-dependent manner (FIGS. 9B-9C). The wound area decreased by ~3 times as much in mice treated with 1 mpk BPD as compared with mice fed placebo (FIG. 9D). Placebo-fed mice were not statistically compared with 5 mpk BPD-treated mice (n=1). Similarly, treatment with BPD increased hair growth in a time- and dose-dependent manner. Mice treated with 1 mpk BPD displayed more hair growth, by ~2.7 fold, than mice fed placebo (FIG. 9E).

Figures 10A, 10B, 10C:
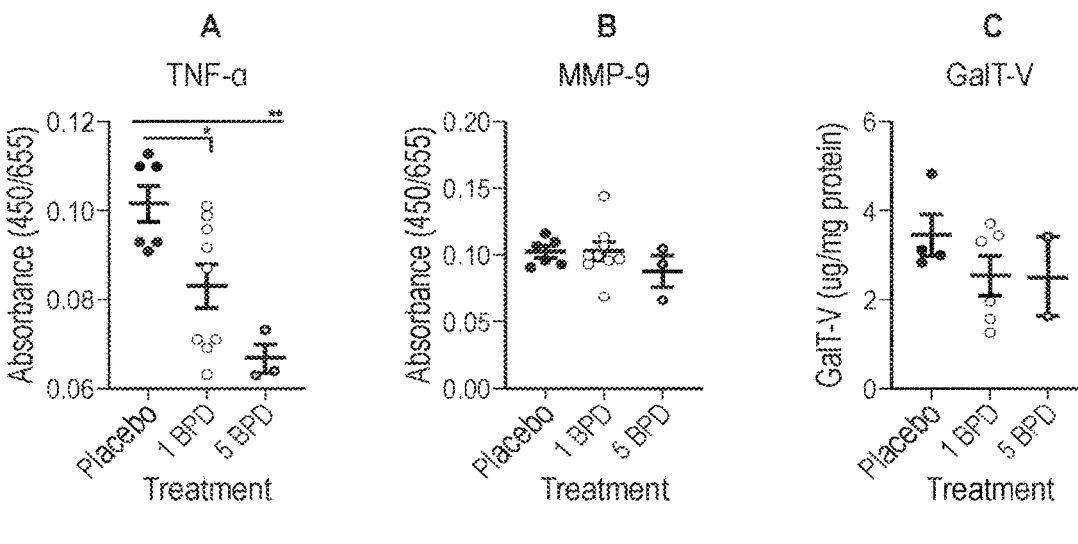
FIGS. 10A-10C are graphs identifying the molecular markers of wounding and GalT-V skin tissue level in wounded normal (C57B16) mice treated with BPD. Wounds were made on the dorsal skin of normal mice. Subsequently, the mice were either fed biopolymer vehicle (placebo), 1 mpk BPD, or 5 mpk BPD. The levels of TNF-α and MMP-9, both of which are biomarkers of wounding, and GalT-V in skin tissue were measured using an ELISA assay. A parametric two-tailed unpaired t test was performed for each. Only the level of TNF-α in skin tissue was statistically significant between the groups (*p<0.05 for placebo-fed mice versus 1 mpk BPD-treated mice; p<0.005 for placebo-fed mice versus 5 mpk BPD-treated mice) (FIG. 10A). Nevertheless, BPD-treated mice showed lower levels of MMP-9 (FIG. 10B), indicating wound healing, and lower levels of GalT-V (FIG. 10C**).

Treatment with BPD decreases the expression of bio-markers of wounding in normal (C57B16) mice. ELISA assays revealed that wounded skin tissue having treatment with BPD dose-dependently decreased the protein expres-sion of established biomarkers of wounding, TNF-α (FIG. 10A) significantly, and MMP-9 and GalT-V (FIG. 10C) only modestly (FIG. 10B).

Figures 11A, 11B, 11C, 11D, 11E:
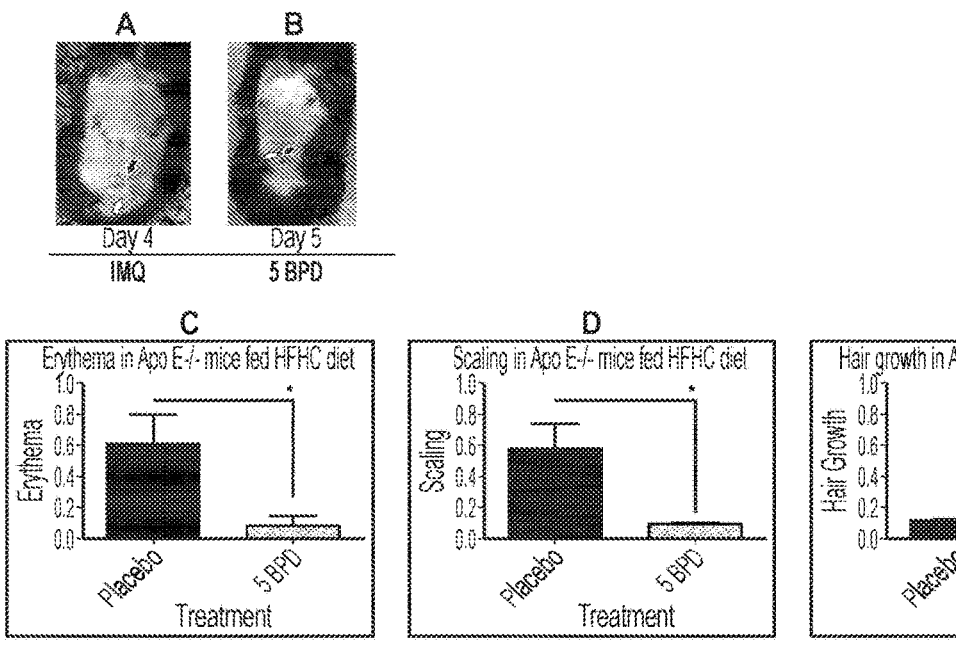
FIGS. 11A-11E are a series of photographs and graphs demonstrating that treatment with BPD increases hair growth and inhibited erythema and scaling/plaque in IMQ-treated ApoE$^{-/-}$ mice fed HFHC diet. ApoE-mice were fed with high fat high cholesterol diet. First, the dorsal area of mice was shaved with NAIR™. Next, imiquimod (IMQ) was applied topically on to the shaven area daily for 5 days and then treated with 5 mpk BPD daily for 5 days by oral gavage.

Topical application of IMQ causes skin erythema and scaling in ApoE$^{-/-}$ fed a HFHC diet, and these phenotypes are reversed by treatment with BPD. Daily topical applica-tion of IMQ for 4 consecutive days to shaven skin area in ApoE–/– mice resulted in marked erythema or reddening of the skin and scaling (FIG. 11A). However, treatment with 5 mg/kg (mpk) of BPD daily by oral gavage completely reversed erythema (*p<0.05) and scaling (*p<0.05) of the skin (FIG. 11B). BPD decreased erythema by ~7 times more (FIG. 11C) and scaling ~6 times more than in placebo-fed mice (FIG. 11D). BPD-treated mice also showed a greater extent of hair growth, but the difference between the two groups was not significant (FIG. 11E). This provides evi-dence that IMQ interferes with hair growth.

Figure 12:
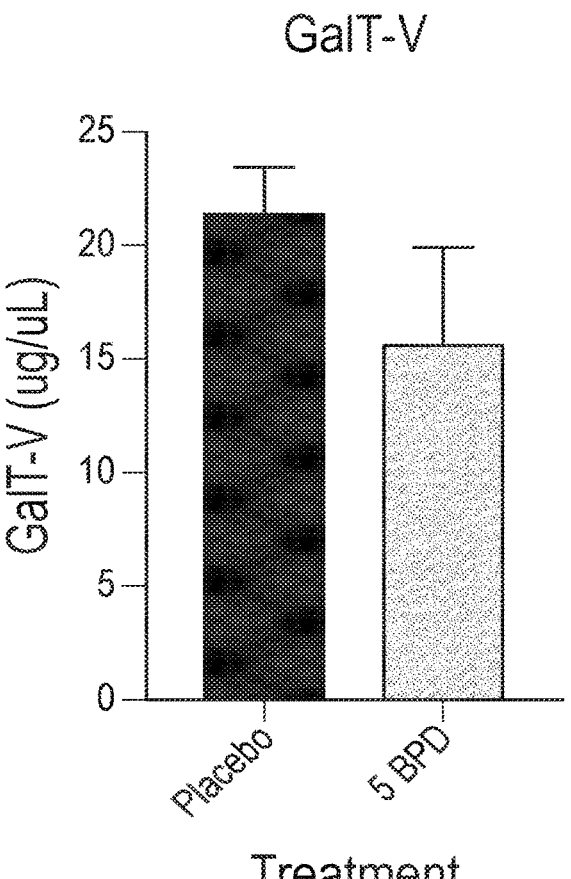
FIG. 12 is a graph demonstrating that treatment with BPD decreases the serum level of GalT-V in imiquimod-treated ApoE$^{-/-}$ mice fed a HFHC diet. ApoE$^{-/-}$ mice were treated with imiquimod (IMQ) for 5 days and then with either 5 mpk BPD or placebo for 5 days. BPD-treated mice displayed a lower serum level of GalT-V than placebo-treated mice (p<0.2162).

Treatment with BPD decreases the serum level of GalT-V in imiquimod-induced psoriasis in ApoE$^{-/-}$ mice fed a HFHC diet. The serum level of GalT-V in IMQ-treated ApoE–/– mice fed a HFHC diet was decreased upon treat-ment with 5 mpk BPD (FIG. 12).

Figures 13A, 13B, 13C:
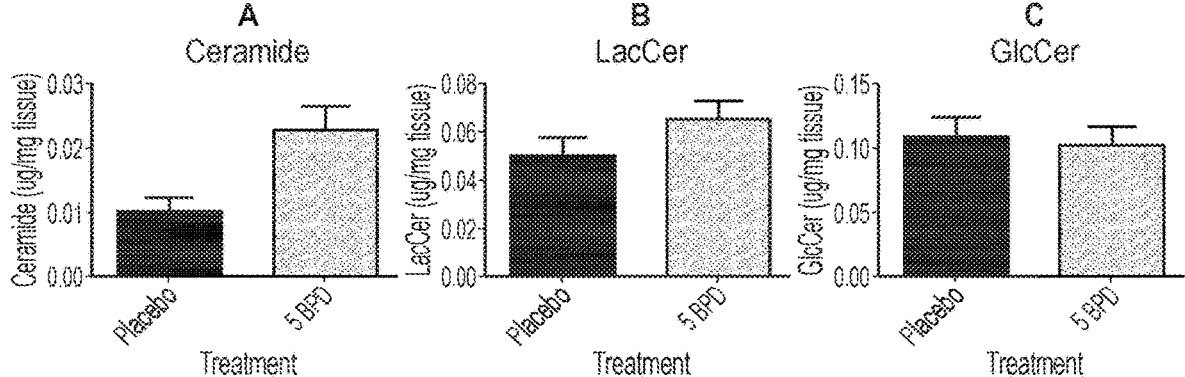
FIGS. 13A-13C are a series of graphs demonstrating that treatment with BPD restores the level of ceramide back to normal in ApoE$^{-/-}$ mice fed HFHC diet. Mice were treated with imiquimod (IMQ) topically onto the shaven area daily for 5 days and then treated with 5 mg/kg body weight of the biopolymer encapsulated drug (BPD) daily for 5 days by oral gavage. BPD increased the level of ceramide (FIG.

Treatment with BPD restores the level of skin ceramide, lactosylceramide and GalT-V to normal in imiquimod-treated ApoE$^{-/-}$ mice fed a HFHC diet. HPTLC and ELISA assays were used to measure the mass of ceramide and LC, and the mass of GalT-V, respectively in the skin tissue of ApoE–/– mice fed a HFHC diet. It was observed that treatment with 5 mpk BPD daily for 5 consecutive days reduced the level of LC and GalT-V but raised the level of ceramide in skin tissue (FIG. 13B).

A HFHC Diet Increases the Level of Ox-LDL Receptors in Imiquimod-Treated ApoE$^{-/-}$ Mice and this is Further Increased by Treatment with BPD.

Western immunoblot assays using antibodies specific to various ox-LDL receptors revealed that feeding a HFHC diet to ApoE–/– mice and topical application of IMQ increased the expression of scavenger receptor proteins compared to normal chow fed mice (FIG. 14). However, treatment with 5 mpk BPD increased the levels of these receptors to accelerate the removal of oxidized LDL from the circulation (FIG. 14).

LOX-1$^{-/-}$ mice are prone to imiquimod-induced psoria-sis-like skin symptoms, which can be ameliorated by treat-ment with BPD. LOX-1$^{-/-}$ male (FIG. 15A) and female mice (FIG. 15C) skin showed significant erythema and scaling induced by daily topical application of IMQ for 5 consecutive days. Conversely, treatment with 5 mpk BPD reversed erythema (FIG. 15E) and scaling (FIG. 15F). Mice treated with 5 mpk BPD showed ~3 times less erythema area and ~8.5 times less scaling area than mice fed placebo. In addition, treatment also increased hair growth; although statistically insignificant, this was evident by a marked increase in the bluish black area, denoting hair shafts and thickened black hairs (FIGS. 15B, 15 D, 15G). However, hair growth was more significant in male mice than in female mice.

The increased serum levels of Ox-LDL, and GalT-V in LOX-1$^{-/-}$ mice following topical application of imiquimod is ameliorated by treatment with BPD. The serum levels of Ox-LDL, and GalT-V in LOX-1$^{-/-}$ mice fed normal chow diet and subject to topical application of IMQ were decreased upon treatment with 5 mpk BPD (FIGS. 16A-16B).

Treatment with BPD did not significantly alter sphingo-lipids in LOX mice. It was observed that treatment with 5 mpk BPD daily for 5 days did not reduce the level of sphingolipids in LOX-1$^{-/-}$ mice skin tissue, except for a modest decrease in LC mass (FIGS. 17A-17C).

Treatment with BPD modestly increased SRA-1 protein expression in LOX-1$^{-/-}$ mice. Western blot assays showed that treatment with BPD modestly increased and decreased, respectively, the protein expression of SRA-1 in LOX-1–/– male and female mice skin tissue (FIG. 18).

Discussion

This study examined the effects of dyslipidemia on IMQ-induced psoriasis-like skin pathology as well as the effects of inhibiting GSL synthesis using BPD in ApoE$^{-/-}$ mice, a widely used mouse model of atherosclerosis, and in LOX-1$^{-/-}$, an ox-LDL receptor-deficient mice. The effects of BPD treatment on skin wound healing and hair growth in normal mice were also examined. Treatment with BPD affected the adverse consequences of psoriasis-like skin pathology, wounds and hair loss. The key findings emanating from this study were: (1) In normal mice, wound healing and hair growth was markedly enhanced by inhibiting GSL synthesis using BPD in a time- and dose-dependent manner. This was associated with a decrease in biomarkers of wounding and inflammation, namely, TNF-α and MMP-9; (2) ApoE$^{-/-}$ mice fed a HFHC diet responded strongly to topical appli-cation of IMQ, resulting in "psoriasis-like" symptoms of the skin involving erythema and scaling; (3) LOX-1$^{-/-}$ mice were also prone to IMQ-induced "psoriasis-like" skin symp-toms; (4) "Psoriasis-like" phenotypes in both types of these transgenic mice were reversed and hair growth was enhanced as a result of treatment with BPD; (5) the molecular and biochemical studies herein, showed that these phenotypic changes in skin tissue were associated with an increase in the number of Ox-LDL receptors. This was accompanied with a decreased skin level of ceramide in order to compensate for an increase in lactosylceramide level due to an increase in the activity or mass of β-1,4GalT-V; (6) Treatment with BPD reversed these phenotypes. The biochemical and molecular mechanisms by which inhibition of GSL synthesis offers a therapeutic target relevant to psoriasis, wound healing and hair growth gleaned from this study are summarized in FIG. 5.

The inventor has shown that feeding a high fat and high cholesterol diet to ApoE$^{-/-}$ mice for a period of 24 weeks (from the age of 12 weeks to 36 weeks) led to hair discoloration, extensive loss of hair (~80%), and the appearance of multiple skin wounds. However, this was reversed by treatment with BPD in a time- and dose-dependent manner. In this present study, experiments were expanded to normal (C57B1-6) mice by shaving the dorsal side of mice and inflicting wounds to the skin. Thereafter, the effects of feeding the mice BPD over a period of ten days were examined. It was observed that wound healing occurred in placebo mice as a natural course of events. However, feeding BPD dose- and time-dependently accelerated wound healing significantly (FIGS. 9A-9E). Also, hair growth was markedly increased in BPD-treated mice.

Previous studies have shown that neutrophil infiltration is a "hallmark" in skin wounding. Apparently, neutrophils constitute nearly 50% of all cell types populating a wound within the first 24 hours. This is due to the release of a number of chemokines such as CXC and CX3C, which bind to their receptors, thereby attracting and enabling neutrophil infiltration into the wound area (Kim, H et al. 2008 *J. Invest. Dermatol* 128:1812-1820 doi. 10.1038 isj.djid 5701223; Su Y Richmond (2015) *Adv. Wound. Care.* (new Rochelle) 4:631-640 doi. 10.1089/wound.2014.0559). By analogy, in the present study, skin wounding is expected to cause massive neutrophil infiltration. As neutrophils are highly enriched with lactosylceramide, they may be released and contribute to inflammation and neutrophil migration (FIG. 5). Wound healing was accelerated by treatment with BPD, which blocks β-1,4 GalT-V activity and decreases its mass. A high fat and cholesterol diet and aging contributed to increased infiltration of neutrophils into the dermis, inflammation, and wounding in ApoE$^{-/-}$ mice; these phenotypes were reversed upon treatment with BPD. These studies in normal mice demonstrated that treatment with BPD in HFHC fed ApoE$^{-/-}$ mice time- and dose-dependently increased hair growth (FIGS. 9A-9E).

Wound healing is a process involving growth factors like PDGF, chemokines, TNF-α, interleukins, matrix metalloproteases (MMPs), tissue inhibitors of metalloproteases (TIMPs), neutrophils, macrophages, platelets, and fibroblasts (Bhunia A. K, Han H, Snowden A, Chatterjee S.1997. *J.Biol. Chem.* 272:15642-15,649; Patel S, Maheshwari A, Chandra A. 2016. *J. Wound Care* 25:46-55.doi:10.12968/jowc.2016.25.1.4633, 34). However, a specific established biomarker of wound healing has not yet been reported. Nevertheless, decreased levels of MMP-9/MMP-1 and a low MMP/TIMP ratio have all been considered to be reliable predictors of wound healing. In the study herein, the mass of MMP-9 and TNF-α were measured and markedly increased levels of these biomarkers within 24 hours after wounding was observed. Conversely, as the wounds healed upon treatment with BPD, the levels of these biomarkers reduced in tandem. In addition, the increased level of β-1,4GalT-V in wounded skin also accompanied the increased level of TNF-α. This was reversed by treatment with BPD. Again, these studies are consistent with a previous report wherein TNF-α was shown to recruit/activate β-1,4GalT-V and to activate a "downstream" signaling cascade leading to increased adhesion of neutrophils to human endothelial cells. This phenotype was blocked by inhibiting LC synthesis using D-PDMP. In particular, of considerable interest is the aging population wherein wound healing is a serious health problem associated with increased systemic and tissue levels of lactosylceramide.

The inventor has previously shown the effects of a high fat and high cholesterol diet on skin inflammation and hair loss in ApoE$^{-/-}$ mice; the effects also included dyslipidemia and an increase in the blood level of Ox-LDL (Bedja, D, et al. (2018) *Scientific Reports,* 8 (1). doi:10.1038/s41598-018-28663-9). However, psoriasis-like skin pathology was not observed. This was accomplished in the present study by the topical application of IMQ, a nucleoside analog, to the dorsal skin of mice. A previous study showed that IMQ application induces inflammation by virtue of increasing the expression of pro-inflammatory cytokines IL-23 and IL-17 in normal mice (Van der Fits L, et al. *J. Immunol* 2009 182:5836-5845) as well as in ApoE$^{-/-}$ mice (Xie X, et al. (2017) *J. Dermatology. Sci.* 88:20-28). The ApoE gene encodes a protein called apolipoprotein E, which is found in interstitial fluid, lymph, and plasma. ApoE is a component of very low density lipoprotein (VLDL), intermediate density lipoproteins, chylomicron remnants, and some subclasses of high density lipoproteins (HDLs). There are three main isoforms of apoE in humans; ApoE3 is the most common while ApoE2 and ApoE4 are associated with type III hyperlipoproteinemia and Alzheimer's disease, respectively (Huang, Y., & Mahley, R. W. (2014). Apolipoprotein E: structure and function in lipid metabolism, neurobiology, and Alzheimer's diseases. *Neurobiology of Disease,* 72 Pt A, 3-12.). ApoE binds with high affinity to certain cell-surface receptors such as the family of low density lipoprotein (LDL) receptors, thereby leading to the uptake of lipoproteins and lipid complexes and the clearing of lipids by cells (Lo Sasso, et al. (2016). *Journal of Translational Medicine,* 14 (1), 146. doi:10.1186/s12967-016-0901-1). ApoE also plays a role in decreasing dietary cholesterol absorption and increasing biliary cholesterol excretion. Since the role of ApoE in lipid homeostasis and metabolism is impeded in ApoE–/– mice, these mice exhibit a buildup of cholesterol deposits in blood, which leads to atherosclerotic plaques. Specifically, cholesterol accumulation in the macrophages of ApoE–/– mice induces inflammation and extracellular matrix degradation. Thus, ApoE knockout mice, generated by inactivating the ApoE gene, is an effective mouse model for studying cardiovascular disease and atherosclerosis. In the present study, IMQ was applied topically daily onto the skin to HFHC-fed ApoE$^{-/-}$ mice and observed extensive scaling and erythema (FIGS. 10A-10C). These phenotypes were reversed in a time-dependent manner by daily oral feeding of BPD. Since the expression of several scavenger receptors known to bind and internalize Ox-LDL is increased in HFHC-fed ApoE$^{-/-}$ mice (FIGS. 16A, 16B), this enables increased uptake of Ox-LDL by cells. However, since BPD blocks Ox-LDL-mediated activation of β-1, 4GalT-V (FIG. 5), it decreased the level of LC and psoriasis-like skin pathology in these transgenic mice. Treatment also decreased the mass of Ox-LDL by preventing LDL oxidation by lowering superoxide generation due to LC mediated activation of NAD (P) H oxidase (FIG. 5). ApoE$^{-/-}$ mice fed a HFHC diet have a lower level of ceramide and higher levels of lactosylceramide and GalT-V mass compared to ApoE$^{-/-}$ mice fed normal chow. However, treatment with BPD reversed the ceramide to lactosylceramide levels and increased hair growth. The observations made in the present study are in agreement with previous findings. In particular the level of ceramide in the skin in placebo mice were significantly lower. And BPD treatment restored ceramide levels and this could explain the metabolic basis of reversal skin lesion s and erythema in ApoE$^{-/-}$ mice fed HFHC diet and topical application of IMQ.

Ox-LDL is taken up by a family of scavenger receptors. The major ones are SRA-1, CD-36 and LOX-1, which play critical roles in the pathogenesis of atherosclerosis. The lectin-like oxidized low-density lipoprotein (LDL) receptor-1, which is encoded by the LOX-1 gene, is the main scavenger receptor that regulates oxidized LDL levels. Although the LOX-1 receptor is located mainly on the membranes of endothelial cells, it is also found in macrophages, platelets, smooth muscle cells, and even in low levels in cardiac fibroblasts. The LOX-1 receptor is made up of four domains: a N-terminal cytoplasmic domain, a single transmembrane domain, a neck domain, and a C-type lectin-like domain at the extracellular C-terminus. This lectin-like domain is the functional part of the receptor that recognizes and binds to oxidized LDL, which is then taken into the cell and degraded (Chen, M., Masaki, T., & Sawamura, T. (2002). *Pharmacology & Therapeutics,* 95 (1), 89-100).

Oxidized LDL activates the LOX-1 receptor, triggering endothelial dysfunction and apoptosis. The basal expression of LOX-1 in endothelial cells is low, but it can be induced by multiple factors. In vitro, inflammatory stimuli, oxidative and mechanical stress, and cytokine e.g. TNF-$\alpha$ activate the LOX-1 receptor. In vivo, pro-atherogenic conditions such as hyperlipidemia, diabetes, and hypertension increase expression of LOX-1 (Mehta, J., Chen, J., Hermonat, P., Romeo, F., & Novelli, G. (2006). Lectin-like, oxidized low-density lipoprotein receptor-1 (LOX-1): A critical player in the development of atherosclerosis and related disorders. Cardiovascular Research, 69 (1), 36-45. doi:10.1016/j.cardiores.2005.09.006). Up-regulation of LOX-1 is associated with atherosclerosis (Goyal T et al. *Curr Atheroscler Rep* (2012) 14:150. https://doi.org/10.1007/s11883-012-0228-1). In a previous study, compared to wild-type mice, LOX-1 knockout mice showed a reduction in atherosclerosis (Mehta, J. L., et al. (2007). *Circulation Research,* 100 (11), 1634-1642). To examine the role played by LOX-1 receptor in IMQ-induced psoriasis-like pathology, in the present study, IMQ was applied onto LOX-1$^{-/-}$ mice fed normal chow and observed that irrespective of sex, LOX-1$^{-/-}$ mice were prone to IMQ-induced psoriasis-like symptoms/pathology (FIGS. 11A-11B). Herein, a time-dependent progressive increase in scaling and erythema were observed, although to a lesser extent observed in ApoE$^{-/-}$ mice fed a HFHC diet (compare FIGS. 10A-10C with FIGS. 11A-11E). Similarly, hair growth in response to treatment with BPD in LOX-1$^{-/-}$ mice was also less pronounced compared to ApoE-/- mice. Thus, the results herein provide evidence that since Ox-LDL uptake is governed by multiple scavenger receptors, gene ablation of the LOX-1 receptor may still allow Ox-LDL uptake via other receptors, rendering LOX-1$^{-/-}$ mice sensitive to IMQ-induced psoriasis-like pathology. However, the key regulatory step in inducing skin inflammation may be the synthesis of LC via the activation of GalT-V. Thus, inhibition of GSL synthesis through BPD is a bonafide and novel approach to mitigate psoriasis-like pathology in mice and in humans.

Ceramide represents nearly 50% of the skin sphingolipids. Decreased content of certain molecular species of ceramide (Cer 3(NP) and Cer 1(EOS) and phytosphingosine and Cer 6Ap with a substantial increase in other species has been shown (Motta S, et al. *Biochim. Biophys. Acta.* 1993; 1182:147-151 doi.10.1016/0925-44439(93)90135-N; Motta S, et al. *Arch Dermatol.* 194:130:452-456. Doi.10.1001/archderm.1994.01690040056007). Thus, the total ceramide mass in psoriatic epidermis is similar to normal epidermis. Increased $\beta$-glucosidase activity (11-fold higher than normal) in epidermal keratome from psoriasis patients compared to control patients has been reported. Conversely, decreased expression of glucosylceramidase mRNA expression was shown in psoriasis skin and this was confirmed with immunohistochemistry using lesional psoriatic epidermis (Alessandrini F et al. (2004) *J. Invest Dermatol.* 116: 1030-1036; Alessandrini F et al. (2001) *J Invest Dermatol.* 2001 March; 116(3):394-400). However non-lesional psoriasis skin also showed a similar distribution of glucosylceramidase. These observations correlate with a decreased level of pro-saposin mRNA and protein responsible for the activation of this enzyme.

The inventor's findings provide evidence that a HFHC diet and aging in ApoE$^{-/-}$ mice can markedly reduce skin ceramide level due to increased activity or mass of GalT-V, which utilizes ceramide to synthesize GC and subsequently LC. Accordingly, restoration of ceramide levels occurs upon blocking the synthesis of LC by using BPD. These observations offer a new paradigm relevant to metabolic basis of skin inflammation and psoriasis. Without wishing to be bound by theory, it was hypothesized that increased synthesis of LC due to Ox-LDL and TNF-$\alpha$-mediated activation of GalT-V accompanied with the delivery of LC to the dermis by infiltrating neutrophils is the key to activating the "inflammation cycle." When this cycle is broken with BPD, skin inflammation is alleviated. In the present study, topical application of IMQ to ApoE$^{-/-}$ mice increased scaling and erythema, accompanying decreased ceramide levels and this was subsequently reversed due to treatment with BPD.

Phospholipase A-2 (PLA-2) is a phospholipase that cleaves phospholipids at the sn-2 position, leading to the release of arachidonic acid, a fatty acid; PLA-2 also plays a role in the generation of lysophospholipids. The latter are strong lysogenic agents. On the other hand, arachidonic acid is a precursor to eicosanoid's, a family of compounds which contribute to inflammation (FIG. 5). Studies have shown an elevated level of arachidonic acid in psoriatic skin as compared to control skin. However, PLA-2 activity in skin lesions and non-lesional area were similar. LC can activate PLA-2 activity in human neutrophils, causing the release of arachidonic acid, and superoxide's, thus activating a signaling pathway involved in promoting the adhesion of neutrophils to the endothelium, one of the "hallmarks" in inflammation and atherosclerosis. Thus, this is a possible mechanistic explanation how LC contributes to inflammatory diseases like psoriasis and how BPD interferes with disease progression by blocking synthesis of GSLs.

This is the first report wherein it was demonstrated that wound healing and hair growth in normal mice can be expedited or enhanced by treatment with BPD in normal mice. Conversely, the skin levels of biomarkers of wounding and pro-inflammatory cytokines are decreased. Topical application of IMQ to ApoE$^{-/-}$ mice and LOX-1$^{-/-}$ markedly reduced scaling and erythema, characteristic of psoriasis-like pathology. Conversely blocking GSL synthesis by using BPD can prevent these phenotype's by restoring skin ceramide level.

In summary, it was demonstrated that blocking glycosphingolipid synthesis has numerous beneficial effects in reversing psoriasis and skin inflammation, and in enhancing hair growth and skin wound healing.

Example 3: Study on the Effects of Topical Application of BPD-Lotion and β-1,4GalT-V Antibody Lotion in Normal (C57Bl-6) Mice Having Psoriasis-Like Skin Symptoms Age onset feeding with a high fat and high cholesterol die to ApoE$^{-/-}$ mice and aging contributed to a hair discoloration, hair loss and wounding of the skin. This was accompanied with a decrease in the level of ceramide mass and increase in Lactosylceramide and the corresponding enzyme B-1, 4 GalT-V level in skin. β1,4-galactosyltransferase V (B-1,4GalT-V), which galactosylates the GlcNAcβ1-6 branch arm of the highly branched N-glycan. Conversely, treatment with BPD dose-dependently reversed these phenotypes. BPD was delivered to these mice orally daily by gavage. The effects of topical delivery of BPD on skin pathology and hair growth were investigated herein.

Materials and Methods

In this experiment it was examined whether topical application of BPD and/or an antibody against B-1,4GalT-V may affect psoriasis-like skin symptoms/pathology in normal mice (C57Bl-6). First, the dorsal area of mice were shaven off using NAIR™. Then IQM was topically applied daily for 5 days on to the shaven area to induce "psoriasis-like" symptoms. Finally, mice were treated with BPD lotion or β1,4-Galactosyltransferase V antibody (BGA) daily. The preparation of BGA was as follows. 90 µL of monoclonal antibody (mAB) against B-1,4GalT-V was mixed with 3 gm of lubricating jelly (McKESSON Medical-Surgical Inc, Richmond VA). One gm of BGA was applied daily on the skin daily. Similarly, 3 mg of BPD powder was mixed vigorously with the lubricating jelly and one gm was applied daily on the skin and photographed. The preparation and characterization of the mAB against human β1,4-Galactosyltransferase V (B-1,4GalT-V; BGA) peptide was described previously (Bedja et al. Sci Report 2018. 8:11463-11473).

Results

As expected application of IMQ daily for 4 days to mice skin caused the appearance of psoriasis-like symptoms/pathology shown in FIGS. 19A, 19C. Topical application of BGA or BPD lotion daily for 3 consecutive days markedly reduced (FIG. 19B) erythema (FIG. 19E) scaling (FIG. 19F) and increased hair growth (FIG. 19G).

Conclusion

Topical delivery of BPD and/or B-1,4GalT-V antibody markedly interferes with psoriasis-like symptoms as well increases hair growth in mice. Thus topical delivery of these therapeutic and immunotherapeutic agents provides an alternative to deliver anti-psoriatic compounds.

Example 4: Inhibition of Glycosphingolipid Synthesis Ameliorates Psoriasis and Increases Hair Growth in Human Skin Organ Cultures Here the effects of inhibiting glycosphingolipid synthesis using a biopolymer-encapsulated inhibitor; D-PDMP (BPD) were examined on psoriasis symptoms e.g. scaling, erythema in psoriatic skin organ cultures and hair growth in normal skin organ cultures. Serum levels of glycosphingolipids were also analyzed.

It was observed that treatment with BPD completely reversed the scaling and erythema in the lesional area of skin in psoriasis patients and increased hair growth in the non-lesional area of skin in a dose-dependent manner. Treatment also markedly increased hair growth in normal mouse and normal human skin organ cultures. The biochemical studies revealed that serum and skin organ cultures from psoriasis patients had significantly lower levels of ceramide. Treatment with BPD significantly increased ceramide levels and decreased the level of glucosylceramide.

In sum, psoriasis skin lesions have lower levels of ceramide contributing to symptoms e.g. scaling and erythema and loss of hair. This is restored upon treatment with BPD. Thus blocking glycosphingolipid synthesis is a novel therapeutic target to ameliorate psoriasis and probably other inflammatory skin diseases and to promote hair growth in man.

Methods

Mice Skin Organ cultures: Normal mice are C57 B1-6 fed normal chow. Mice were euthanized, shaved, and 3 mm biopsies were taken using disposable biopsy punches. Biopsies were cultured in sterile 24-well plastic wells with Keratinocyte basal growth medium (Lonza, Germany) in 10% dialyzed fetal calf serum growth medium supplemented with and without BPD or a biopolymer, suspended in 5% Tween-20 in phosphate buffer-saline (placebo) for 7 days. Medium was changed, treatment re-applied, and photos taken every other day. The biopsies were stored in 4% formalin and final images were taken through the JHMI pathology lab services (under the direction of Mr. Norman Davis). Fiber optic lighting and a Nikon multi-photo-macro systemNikoncameraD750 was used.

Collection of blood and preparation of Skin Organ cultures from Psoriasis patients and normal subjects: Johns Hopkins Institutional Committee on human subject's approval was sought prior to skin biopsy collections. Also informed consent was obtained from all subjects volunteering blood samples and skin biopsy in this study.

Non-fasting blood, 10 mL were drawn by venipuncture from the patient subjects in heparinized tubes and centrifuged for 30 min at 3,000 rpm. Serum was collected and small aliquots frozen away prior to experimentation.

Each psoriasis patient had two 4 mm biopsies taken, one from a lesional area and one from a non-lesional area. Normal participants also had two 4 mm biopsies taken from separate areas. Each biopsy was cut in half, with one half treated with 5 BPD and the other half treated with a placebo in growth medium. Medium was changed, treatment re-applied, and photos taken every other day for up to 9 days. The biopsies were stored in 4% formalin and final images were taken through the JHMI pathology lab services. There were 10 participants (5 clinically diagnosed psoriasis patients and 5 normal subjects) in total of varying ages, sexes, ethnicities, and races.

Hair measurements: Photos from the first and last days of culturing both human and mouse biopsies were taken using a dissecting microscope under 4x magnification using phase contrast. Individual hairs were measured manually using an image editing program, and the lengths, thickness, and number were recorded. The length of each hair from the first day was subtracted from its length at the final day, and the average change in length for each biopsy was calculated. The change in the total number of hairs for each biopsy was also recorded.

Hair growth in live mice: Normal mice (C57 B1-6) fed normal chow were treated daily with placebo or BPD using oral gavage for 9 days. Mice were shaved on day 0, photos were taken daily. Hair growth was measured as the area of hair grown in the shaved region over 9 days and presented as the proportion of the total shaved area. Hair area was measured using an image editing program.

Measurement of Glycosphingolipids. Mouse and human skin tissues were weighed and extracted in acetonitrile-methanol (9:1v/v) supplemented with internal standards. Glycosphingolipids were analyzed following separation on HPTLC plates using chloroform-methanol-water (100:42:6 v/v). The plate was calibrated with multiple standard solutions of ceramide, glucosylceramide, Lactosylceramide and D-PDMP run in triplicate. Following densitometric scanning of the plate the gel bands were quantified using an image J computer program.

Results

Treatment with BPD increases hair growth in mice: Biopsies of normal mice (C57 B1-6) were taken and hair growth measured over seven days in the presence of varying doses of BPD or a biopolymer (placebo). Visually, 2 mpk BPD treatment over seven days was sufficient to produce a noticeable change in the density and length of hair when compared to the placebo control (FIGS. 20A-20B). Biopsies treated with BPD showed a dose-dependent increase in the number of hairs grown over seven days, up to 2.5 mpk BPD (FIG. 20C). There was a significant change in the number of observable hairs in biopsies treated with 2.5 mpk BPD compared to placebo (FIG. 20C). Greater than 5 mpk BPD showed little additional change in hair growth, suggesting that we reached saturation of the drug effectiveness. The thickness and length of hairs was also recorded, but no significant differences were found. The discrepancy between the visually increased hair growths in FIGS. 20A-20B and the quantified hair growth is likely due to limitations in instrument sensitivity when measuring hair length using images of live tissues under a dissecting microscope versus the fixed tissue images in FIGS. 20A-20B. Live mice treated with BPD showed significant hair growth with just 1 mpk BPD treatment (FIG. 20D).

Treatment with BPD increases hair growth in human skin organ cultures and may reverse scaling and erythema in patients with psoriasis. In patients with psoriasis, there is a visually decreased level of scaling and erythema in the lesional biopsy treated with 5 mpk BPD when compared to the other half of the same biopsy treated with placebo (FIGS. 21A-21B).

Biopsies from normal participants and non-lesional areas of psoriasis patients showed significant increases in hair growth, as measured by the change in the number and length of hairs on each biopsy (FIGS. 21C, 21D). Hair thickness was also measured, although no significant changes were found.

GSL analysis revealed that serum from psoriasis patients had statistically significant lower level of ceramides (FIG. 22A). The level of glucosylceramide was also modestly lower (FIG. 22B). Both lesional and non-lesional areas of psoriasis skin were observed to have significantly lower levels of ceramides compared to normal human skin (FIG. 23A). Treatment with BPD restored ceramide levels in lesional skin biospies. Treatment decreased GlcCer level in these skin tissue samples (FIG. 23B). Treatment did not alter the level of Lactosylceramide significantly in lesional skin biopsies (FIG. 23C).

Discussion

The results demonstrated that BPD treatment can increase hair growth in mice and humans skin organ cultures and may reduce psoriasis lesioning. BPD can act directly on skin tissue, as shown through the effects on mouse and human skin biopsies. Experiments on live mice treated with BPD orally show increased drug effectiveness at lower concentrations, suggesting the drug may also affect hair growth through more distal mechanisms. In humans, changes in hair growth and psoriasis lesioning seem to be specific to individuals with some having experienced dramatic changes. Treating biopsies of individual patients may be a useful method to approximate how an individual will respond to treatment before pursuing further testing or recommending BPD therapy and effective dose.

BPD has previously been shown to inhibit the synthesis of GlcCer and LacCer in mice and rabbits fed a western diet (Chatterjee S, Bedja D, Mishra S, et al. Inhibition of Glycosphingolipid Synthesis Ameliorates Atherosclerosis and Arterial Stiffness in Apolipoprotein $E^{-/-}$ Mice and Rabbits Fed a High-Fat and -Cholesterol Diet. *Circulation.* 2014; 129(23):2403-2413. doi:10.1161/circulationaha.113.007559). LacCer was also previously reported to increase diapedesis of immune cells through regulating PECAM-1 expression, the cell adhesion molecule vital for adhesion and diapedesis of monocytes, lymphocytes, and neutrophils (Gong N, Wei H, Chowdhury S H, Chatterjee S. *Proceedings of the National Academy of Sciences.* 2004; 101(17):6490-6495. doi:10.1073/pnas.0308684101). The sped-up life cycle of skin cells typical of psoriasis is characterized by inflammation and rapid cell proliferation which give rise to erythema and scaling. Increased diapedesis of neutrophils which leads to inflammation, along with increased cell proliferation through C-fos in response to LacCer may explain how ceramides are connected to psoriasis lesioning (FIG. 24).

In this study, psoriasis patients present lower circulating levels of ceramide as well as decreased ceramide and LacCer in lesional skin tissue (FIG. 3A, FIGS. 23A-23C). These reduced levels of ceramide and LacCer were reversed in response to BPD treatment, resembling normal levels (FIGS. 23A-23C). These results suggest that BPD blocks GlcCer/LacCer synthesis, resulting in ceramide build up to normal levels. Reduced LacCer synthesis reduces the downstream effects on skin inflammation and cell proliferation, thus ameliorating psoriasis symptoms (FIG. 24).

Increased hair growth in normal mouse and human skin in response to BPD treatment can be explained through a similar mechanism. Increased LacCer in mice models of atherosclerosis (ApoE$^{-/-}$, western diet) results in hair loss (Bedja et al., 2018). Inhibition of glycosphingolipid synthesis in this model reversed this hair loss (Bedja et al., 2018). By reducing inflammation and the production of ROS through decreasing the synthesis of LacCer, hair loss is reduced, thus promoting overall hair growth. The fact that this occurs in normal mouse and human skin suggests that even low levels of LacCer in the skin can inhibit hair growth.

The results are limited by the short-term design of the study and limited biochemical analysis and psoriasis lesioning quantification. In the future it would be beneficial to observe the effects of BPD on other related biomarkers of psoriasis such as sphingosine-1-phosphate, a product of
ceramide which has been linked to increased immune cell
diapedesis and activation of inflammation, cell division
pathways (NF-κB, TNF-α, IL-8) (Moskot M, et al. *International Journal of Molecular Sciences.* 2018; 19(1): 247.
doi:10.3390/ijms19010247). In addition, the dramatic influence of BPD on skin biopsies provides evidence that BPD
may be effective when applied topically. Overall, these
results support an exciting and novel therapeutic use of
glycosphingolipid synthesis inhibitors as a treatment for
psoriasis and some forms of alopecia.

54

OTHER EMBODIMENTS

From the foregoing description, it will be apparent that
variations and modifications may be made to the invention
described herein to adopt it to various usages and conditions.
Such embodiments are also within the scope of the following claims.

All citations to sequences, patents and publications in this
specification are herein incorporated by reference to the
same extent as if each independent patent and publication
was specifically and individually indicated to be incorporated by reference.

What is claimed:

1. A method of treating hair loss or alopecia comprising:
   orally or topically administering to a subject in need thereof a composition comprising a therapeutically effective amount of an encapsulated inhibitor of glycosphingolipid synthesis inhibitor,
   wherein the glycosphingolipid synthesis inhibitor is D-threo-1-phenyl-2-decanoylamino-3-morpholino-1-propanol (D-PDMP);
   wherein the D-PDMP is encapsulated in a polyethylene glycol-sebacic acid polymer; and wherein the effective amount is a dose amount of 1 mg to 10 mg of D-PDMP per kg of subject body weight.

2. The method of claim 1, wherein the composition is administered topically in the form of a cream, gel, ointment, spray, balm, emulsion, liposome, liquid crystal preparation, lotion, or any combination thereof.

3. The method of claim 1, wherein the composition is administered topically, and the composition further comprises one or more lipids comprising fatty acids, free fatty acids, cholesterol, sterol esters, triglycerides, diglycerides, glycerides, wax esters, squalene, ceramides, phospholipids, glycolipids, linoleic acids or combinations thereof.

4. The method of claim 3, wherein the composition comprises ceramide to lipid ratios from about 1:1 to 10:1.

5. A method of treating hair discoloration comprising:

orally or topically administering to a subject in need thereof a composition comprising a therapeutically effective amount of an encapsulated inhibitor of glycosphingolipid synthesis inhibitor, wherein the glycosphingolipid synthesis inhibitor is D-threo-1-phenyl-2-decanoylamino-3-morpholino-1-propanol (D-PDMP);

wherein the D-PDMP is encapsulated in a polyethylene glycol-sebacic acid polymer; and wherein the effective amount is a dose amount of 1 mg to 10 mg of D-PDMP per kg of subject body weight.

6. The method of claim 5, wherein the composition is administered topically in the form of a cream, gel, ointment, spray, balm, emulsion, liposome, liquid crystal preparation, lotion, or any combination thereof.

7. The method of claim 5, wherein the composition is administered topically, and the composition further comprises one or more lipids comprising fatty acids, free fatty acids, cholesterol, sterol esters, triglycerides, diglycerides, glycerides, wax esters, squalene, ceramides, phospholipids, glycolipids, linoleic acids or combinations thereof.

8. The method of claim 7, wherein the composition comprises ceramide to lipid ratios from about 1:1 to at least 10:1.

\* \* \* \* \*

SEQUENCE LISTING

```
<160> NUMBER OF SEQ ID NOS: 9

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Gly Ala Gln Val Tyr Glu Gln Val Leu Arg Ser Ala Tyr Ala Lys
1               5                   10                  15

Arg Asn Ser Ser Val Asn Asp
            20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
catgaacacc tcccgatctt                                               20

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttcatggcct ctttgaaacc cct                                           23

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gccagctcct ttttctgatg                                               20

<210> SEQ ID NO 5
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cctgcaggct tcttccatag                                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtgtgtgac ggggatgtct                                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cttccgcaat gtactgagca                                                              20

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggatccacca cagtccatgc catcac                                                       26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aagctttcca ccaccctgtt gctgta                                                       26
```